(12) United States Patent
Liu et al.

(10) Patent No.: US 9,051,606 B2
(45) Date of Patent: Jun. 9, 2015

(54) METHODS AND COMPOSITIONS FOR NUCLEIC ACID DETECTION

(75) Inventors: Guozhen Liu, Indianapolis, IN (US); Quan Peng, Rockville, MD (US); Yexun Wang, Ellicott City, MD (US); Samuel J. Rulli, Frederick, MD (US); Jing-Yi Lo, North Potomac, MD (US); Rachel Gardner, Frederick, MD (US); Grace J. Kim, Frederick, MD (US)

(73) Assignee: QIAGEN GAITHERSBURG, INC., Frederick, MD (US)

( * ) Notice: Subject to any disclaimer, the term of this patent is extended or adjusted under 35 U.S.C. 154(b) by 282 days.

(21) Appl. No.: 13/230,340

(22) Filed: Sep. 12, 2011

(65) Prior Publication Data

US 2012/0178078 A1    Jul. 12, 2012

Related U.S. Application Data

(60) Provisional application No. 61/381,815, filed on Sep. 10, 2010.

(51) Int. Cl.
- *C12P 19/34* (2006.01)
- *C12Q 1/68* (2006.01)
- *C12Q 1/70* (2006.01)

(52) U.S. Cl.
CPC ............ *C12Q 1/6816* (2013.01); *C12Q 1/6886* (2013.01); *C12Q 1/703* (2013.01); *C12Q 1/706* (2013.01); *C12Q 1/707* (2013.01)

(58) Field of Classification Search
CPC .... C12Q 1/6816; C12Q 1/6886; C12Q 1/703; C12Q 1/706; C12Q 1/707; C12Q 2521/345
USPC ................................. 435/6.1, 91.2
See application file for complete search history.

(56) References Cited

U.S. PATENT DOCUMENTS

| | | | |
|---|---|---|---|
| 5,210,015 A | 5/1993 | Gelfand et al. | |
| 5,723,591 A | 3/1998 | Livak et al. | |
| 5,807,718 A | 9/1998 | Joyce et al. | |
| 5,866,336 A | 2/1999 | Nazarenko et al. | |
| 5,876,930 A | 3/1999 | Livak et al. | |
| 6,090,552 A | 7/2000 | Nazarenko et al. | |
| 6,150,097 A | 11/2000 | Tyagi et al. | |
| 6,174,670 B1 | 1/2001 | Wittwer et al. | |
| 6,183,959 B1 | 2/2001 | Thompson | |
| 6,201,113 B1 | 3/2001 | Todd et al. | |
| 6,326,174 B1 | 12/2001 | Joyce et al. | |
| 6,355,415 B1 | 3/2002 | Wagner | |
| 7,141,665 B1 | 11/2006 | Joyce et al. | |
| 7,355,035 B1 | 4/2008 | Atkins et al. | |
| 7,413,708 B2 | 8/2008 | Mayrand | |
| 2007/0231810 A1 | 10/2007 | Todd | |
| 2010/0035229 A1 | 2/2010 | Rimsky | |
| 2010/0136536 A1 | 6/2010 | Todd | |
| 2010/0221711 A1 | 9/2010 | Nauwelaers | |
| 2011/0143338 A1 | 6/2011 | Todd | |

FOREIGN PATENT DOCUMENTS

WO   WO 2007/041774   4/2007
WO   WO 2008/122084   10/2008

OTHER PUBLICATIONS

Markham et al., Bioinformatics, vol. II. Structure, Functions and Applications (KeithJM, ed), pp. 1-33. Human Press, Totowa, NJ, Sep. 2008.*
Zipper et al. (2004). "Investigations on DNA intercalation and surface binding by SYBR Green I, its structure determination and methodological implications". Nucleic acids research 32 (12): e103.
Schneeberger et al. (1995) Quantitative detection of reverse transcriptase—PCR products by means of a novel and sensitive DNA stain. PCR Methods Appl., 4,234-238.
Mokany, (2010), J. Am. Chem. Soc., 132:1051-1059.
Brown, (2003), Biochem., 42:7152-7161.
Santoro, (1997), PNAS, 94:4262-4266.
Furman, (2010), J. Am. Chem. Soc., 132:11692-11701.
Nauwelaers, (2009), J. Clin. Viro., 46:238-243.
Written Opinion of the International Searching Authority dated Apr. 13, 2012 for PCT/US2011/051248 filed on Sep. 9, 2011.
Gerasimova, Chem Biol. Feb. 26, 2010;17(2):104-6.
Teller, Curr Opin Biotechnol. Aug. 2010;21(4):376-91.

* cited by examiner

*Primary Examiner* — Cynthia B Wilder
(74) *Attorney, Agent, or Firm* — LeClairRyan, a professional corporation; Robin L. Teskin

(57) ABSTRACT

The present application relates to Multicomponent Nucleic Acid Enzymes (MNAzymes), which may be used for detecting, identifying and/or quantifying targets. More particularly, this application provides methods of designing and making more reliable MNAzymes, as well as compositions comprising MNAzyme components and methods of using MNAzymes.

20 Claims, 47 Drawing Sheets

FIG. 1

|  | Total Design | Success Design | Failed Design | | Success Rate |
|---|---|---|---|---|---|
|  |  |  | PCR Failure | Non-PCR Failure |  |
| GL1&2 | 178 | 110 | 29 | 39 | 62% |
| GL3-5 | 362 | 325 | 14 | 23 | 90% | dG = -1.58 dG = -13.80 dG = -5.45 GSTM3

FIG. 5

| | | Partzyme B Sensor First Base | | | | All | |
|---|---|---|---|---|---|---|---|
| | | A | C | G | T | | |
| Partzyme A Sensor Last Base | A | N/A (0) | 6.13 (2) | 3.21 (5) | 5.29 (1) | 4.20 (8) | |
| | C | 1.21$^x$ (4) | 2.68$^x$ (18) | 1.12 (1) | 2.16$^x$ (6) | 2.32$^x$ (29) | |
| | G | 2.43 (2) | 4.7 (17) | 5.13 (22) | 3.8 (2) | 4.77 (43) | |
| | T | N/A (0) | 1.74 (1) | 1.56$^x$ (3) | N/A (0) | 1.61$^x$ (4) | |
| | All | 1.62$^x$ (6) | 3.74 (38) | 4.35 (31) | 2.87 (9) | 3.72 (84) | |

FIG. 6

| | | Partzyme B Sensor First Base | | | | All | |
|---|---|---|---|---|---|---|---|
| | | A | C | G | T | | |
| Partzyme A Sensor Last Base | A | 4.4 (1) | 7.1 (3) | 4.7 (5) | N/A (0) | 5.48 (9) | |
| | C | 1.9$^x$ (2) | 4.6 (23) | 5.4 (4) | 2$^x$ (2) | 4.39$^x$ (31) | |
| | G | 3.5 (2) | 8 (14) | 6.5 (21) | 6.3 (5) | 6.92 (42) | |
| | T | N/A (0) | 2$^x$ (3) | 2.7$^x$ (9) | N/A (0) | 2.54$^x$ (12) | |
| | All | 3.06$^x$ (5) | 5.73 (43) | 5.30 (39) | 5.08 (7) | 5.36 (94) | |

FIG. 7

|                   | Junction(2+2) |       |
|-------------------|---------------|-------|
|                   | GG\|GA        | All*  |
| Count             | 10            | 96    |
| Average Isothermal| 7.61          | 9.93  |
| STDEV Isothermal  | 1.65          | 2.03  |
| T-test            | 0.00          |       |

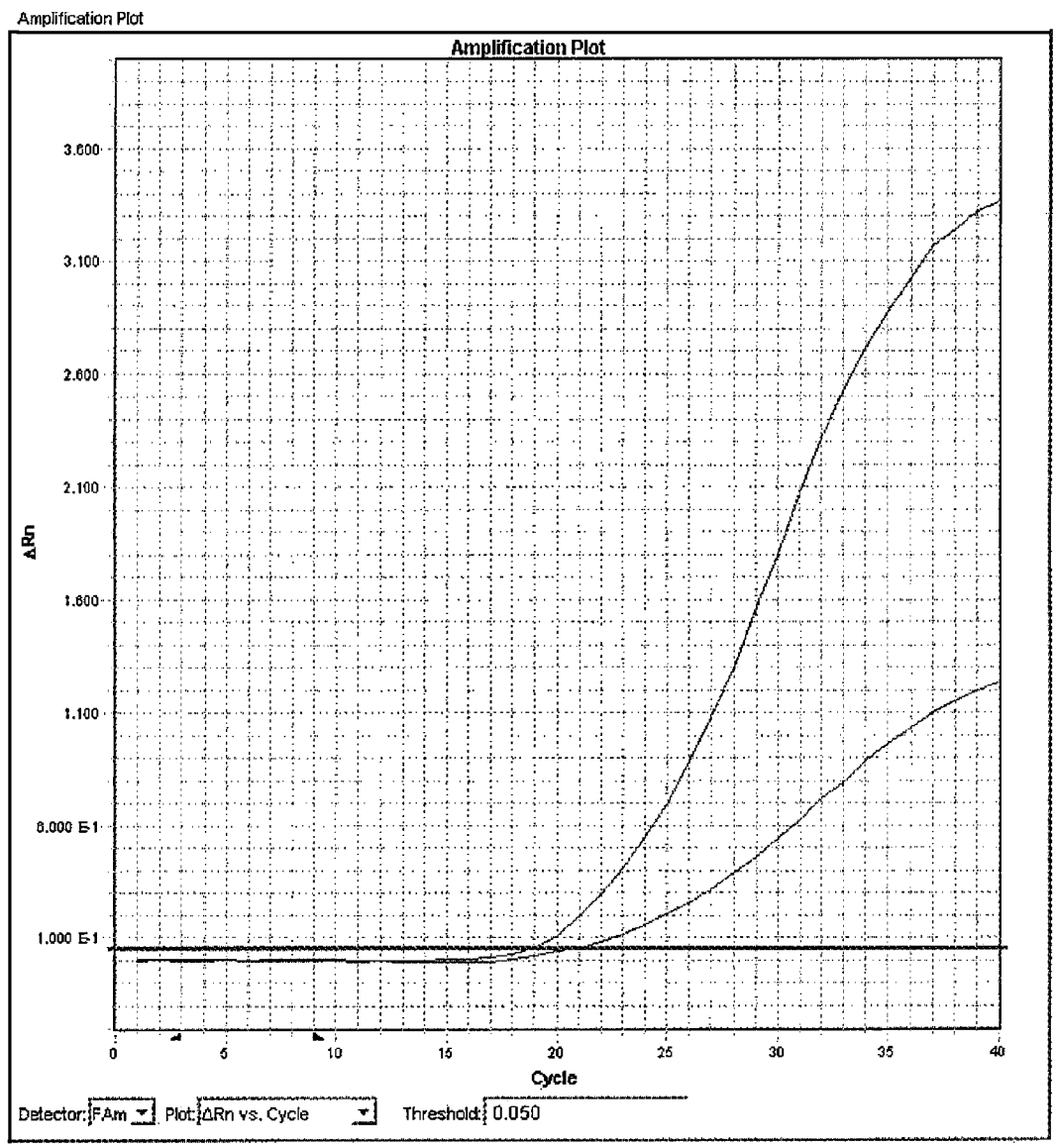

5U - BIRC4

SAB - BIRC4

2U - BAG1

5U - BAG1

SAB - BAG1

2U - BIRC3

5U - BIRC3

SAB - BIRC3

FIG. 9

Gene List 1, Singleplex:

|  | pH 7.4 | pH 7.9 | pH 8.2 | pH 8.4 |
|---|---|---|---|---|
| %Bad | 61% | 31% | 33% | 36% |
| %Marginal | 25% | 31% | 12% | 13% |
| %Good | 14% | 39% | 55% | 51% |

ADAMTS1

CCR2

COL4A2

FIG. 11

| GL1 | |
|---|---|
| Symbol | Ref Seq |
| BAG3 | NM_004281 |
| TNFRSF7 | NM_001242 |
| TNFRSF9 | NM_001561 |
| BAG4 | NM_004874 |
| BIK | NM_001197 |
| TNFRSF10A | NM_003844 |
| BRAF | NM_004333 |
| CIDEA | NM_001279 |
| RIPK2 | NM_003821 |
| LTBR | NM_002342 |
| BAK1 | NM_001188 |
| TNFRSF12 | NM_003790 |
| DFFA | NM_004401 |
| LTA | NM_000595 |
| TRAF2 | NM_021138 |
| TNFSF5 | NM_000074 |
| BID | NM_001196 |
| BIRC1 | NM_004536 |
| BIRC8 | NM_033341 |
| TP73 | NM_005427 |
| RPL13A | NM_012423 |
| NOD1 | NM_006092 |
| TNFSF7 | NM_001252 |
| CARD6 | NM_032587 |
| AKT1 | NM_005163 |
| CASP6 | NM_032992 |
| BNIP1 | NM_001205 |
| CASP5 | NM_004347 |
| CASP8 | NM_001228 |
| BIRC6 | NM_016252 |
| BAD | NM_004322 |
| CASP14 | NM_012114 |
| TNFSF6 | NM_000639 |
| TNF | NM_000594 |
| CIDEB | NM_014430 |
| TP53 | NM_000546 |
| ABL1 | NM_005157 |
| BCL2L1 | NM_138578 |
| GADD45A | NM_001924 |
| B2M | NM_004048 |
| APAF1 | NM_001160 |
| CASP7 | NM_001227 |
| BCLAF1 | NM_014739 |
| BFAR | NM_016561 |
| TNFSF8 | NM_001244 |
| BIRC3 | NM_001165 |
| CRADD | NM_003805 |
| NOL3 | NM_003946 |
| TNFSF10 | NM_003810 |

| GL2 | |
|---|---|
| Symbol | Ref Seq |
| ANXA5 | NM_001154 |
| ATM | NM_000051 |
| CAT | NM_001752 |
| CCL21 | NM_002989 |
| CCL3 | NM_002983 |
| CCL4 | NM_002984 |
| CCNC | NM_005190 |
| CCNG1 | NM_004060 |
| CDKN1A | NM_000389 |
| CHEK2 | NM_007194 |
| CRYAB | NM_001885 |
| CSF2 | NM_000758 |
| CXCL10 | NM_001565 |
| CYP1A1 | NM_000499 |
| CYP2E1 | NM_000773 |
| CYP7A1 | NM_000780 |
| DDB1 | NM_001923 |
| DDIT3 | NM_004083 |
| DNAJA1 | NM_001539 |
| DNAJB4 | NM_007034 |
| E2F1 | NM_005225 |
| EGR1 | NM_001964 |
| EPHX2 | NM_001979 |
| ERCC1 | NM_001983 |
| ERCC3 | NM_000122 |
| FMO1 | NM_002021 |
| FMO5 | NM_001461 |
| GDF15 | NM_004864 |
| GPX1 | NM_000581 |
| GSR | NM_000637 |
| GSTM3 | NM_000849 |
| HMOX1 | NM_002133 |
| HSF1 | NM_005526 |
| HSPA1L | NM_005527 |
| HSPA4 | NM_002154 |
| HSPA5 | NM_005347 |
| HSPA6 | NM_002155 |
| HSPA8 | NM_006597 |
| HSPB1 | NM_001540 |
| HSPD1 | NM_002156 |
| HSPE1 | NM_002157 |
| HSPH1 | NM_006644 |
| IGFBP6 | NM_002178 |
| IL18 | NM_001562 |
| IL1A | NM_000575 |
| IL1B | NM_000576 |
| IL6 | NM_000600 |
| ITGA2 | NM_002203 |
| ITGA3 | NM_002204 |

| GL3.2 | |
|---|---|
| Symbol | Ref Seq |
| ADAMTS1 | NM_006988 |
| ADAMTS13 | NM_139025 |
| ADAMTS8 | NM_007037 |
| CDH1 | NM_004360 |
| COL12A1 | NM_004370 |
| COL16A1 | NM_001856 |
| COL4A2 | NM_001846 |
| COL5A1 | NM_000093 |
| COL6A1 | NM_001848 |
| COL7A1 | NM_000094 |
| COL8A1 | NM_001850 |
| VCAN | NM_004385 |
| CTGF | NM_001901 |
| CTNNB1 | NM_001904 |
| CTNND1 | NM_001331 |
| CTNND2 | NM_001332 |
| FN1 | NM_002026 |
| HAS1 | NM_001523 |
| ITGA1 | NM_181501 |
| CCR5 | NM_000579 |
| CCR6 | NM_004367 |
| CCR7 | NM_001838 |
| ITGA5 | NM_002205 |
| ITGA6 | NM_000210 |
| ITGA7 | NM_002206 |
| ITGAL | NM_002209 |
| ITGAM | NM_000632 |
| CXCL11 | NM_005409 |
| ITGB2 | NM_000211 |
| CXCL2 | NM_002089 |
| KAL1 | NM_000216 |
| LAMA3 | NM_000227 |
| LAMB1 | NM_002291 |
| LAMB3 | NM_000228 |
| LAMC1 | NM_002293 |
| IL10RA | NM_001558 |
| MMP10 | NM_002425 |
| MMP11 | NM_005940 |
| MMP12 | NM_002426 |
| MMP14 | NM_004995 |
| MMP16 | NM_005941 |
| IL1F5 | NM_012275 |
| MMP3 | NM_002422 |
| MMP7 | NM_002423 |
| MMP8 | NM_002424 |
| IL1F9 | NM_019618 |
| NCAM1 | NM_000615 |
| SELE | NM_000450 |
| SELL | NM_000655 |

FIG. 11 (continued)

| GL1 | |
|---|---|
| Symbol | Ref Seq |
| CASP1 | NM_033292 |
| TNFRSF1A | NM_001065 |
| HPRT1 | NM_000194 |
| BIRC4 | NM_001167 |
| BCL10 | NM_003921 |
| TNFRSF6 | NM_000043 |
| DAPK1 | NM_004938 |
| TRADD | NM_003789 |
| TNFRSF5 | NM_001250 |
| CASP4 | NM_001225 |
| BCL2L2 | NM_004050 |
| MCL1 | NM_021960 |
| BNIP3 | NM_004052 |
| CASP9 | NM_001229 |
| BIRC2 | NM_001166 |
| BNIP3L | NM_004331 |
| TNFRSF10B | NM_003842 |
| BNIP2 | NM_004330 |
| IGF1R | NM_000875 |
| CARD8 | NM_014959 |
| FADD | NM_003824 |
| CASP3 | NM_004346 |
| ACTB | NM_001101 |
| TRAF3 | NM_003300 |
| TNFRSF21 | NM_014452 |
| TNFRSF11B | NM_002546 |
| TP53BP2 | NM_005426 |
| CASP10 | NM_001230 |
| BCL2L11 | NM_006538 |
| GAPD | NM_002046 |
| TRAF4 | NM_004295 |
| BAX | NM_004324 |
| CASP2 | NM_032982 |
| BCL2 | NM_000633 |
| BCL2A1 | NM_004049 |
| BAG1 | NM_004323 |

| GL2 | |
|---|---|
| Symbol | Ref Seq |
| ITGA4 | NM_000885 |
| ITGAV | NM_002210 |
| ITGB1 | NM_002211 |
| ITGB3 | NM_000212 |
| ITGB5 | NM_002213 |
| JUN | NM_002228 |
| MAP2K1 | NM_002755 |
| MCAM | NM_006500 |
| MDM2 | NM_002392 |
| MET | NM_000245 |
| MIF | NM_002415 |
| MMP1 | NM_002421 |
| MMP2 | NM_004530 |
| MMP9 | NM_004994 |
| MT2A | NM_005953 |
| MTA1 | NM_004689 |
| MTA2 | NM_004739 |
| MYC | NM_002467 |
| NFKB1 | NM_003998 |
| NME1 | NM_000269 |
| NME4 | NM_005009 |
| NOS2 | NM_000625 |
| PDGFA | NM_002607 |
| PDGFB | NM_002608 |
| PLAU | NM_002658 |
| PLAUR | NM_002659 |
| PNN | NM_002687 |
| POR | NM_000941 |
| PRDX1 | NM_002574 |
| PRDX2 | NM_005809 |
| PTGS1 | NM_000962 |
| RAD23A | NM_005053 |
| RAD50 | NM_005732 |
| RAF1 | NM_002880 |
| RB1 | NM_000321 |
| S100A4 | NM_002961 |
| SERPINB5 | NM_002639 |
| SERPINE1 | NM_000602 |
| SOD1 | NM_000454 |
| SOD2 | NM_000636 |
| UGT1A4 | NM_007120 |
| UNG | NM_003362 |
| XRCC1 | NM_006297 |
| XRCC2 | NM_005431 |

| GL3.2 | |
|---|---|
| Symbol | Ref Seq |
| SELP | NM_003005 |
| SPARC | NM_003118 |
| SPG7 | NM_003119 |
| SPP1 | NM_000582 |
| TGFBI | NM_000358 |
| THBS2 | NM_003247 |
| TIMP1 | NM_003254 |
| TIMP3 | NM_000362 |
| VCAM1 | NM_001078 |
| BCL6 | NM_001706 |
| C3 | NM_000064 |
| C5 | NM_001735 |
| CCL1 | NM_002981 |
| CCL11 | NM_002986 |
| CCL13 | NM_005408 |
| CCL15 | NM_032965 |
| CCL17 | NM_002987 |
| CCL18 | NM_002988 |
| CCL20 | NM_004591 |
| CCL23 | NM_005064 |
| IFNA2 | NM_000605 |
| IL10RB | NM_000628 |
| IL13RA1 | NM_001560 |
| IL1RN | NM_000577 |
| CARD18 | NM_021571 |
| CCL8 | NM_005623 |
| CCR1 | NM_001295 |
| CCR2 | NM_000648 |
| CCR3 | NM_001837 |
| CCR4 | NM_005508 |
| CCR8 | NM_005201 |
| CCR9 | NM_006641 |
| CRP | NM_000567 |
| CX3CR | NM_001337 |
| CXCL1 | NM_001511 |
| CXCL12 | NM_000609 |
| CXCL9 | NM_002416 |
| IL10 | NM_000572 |
| IL13 | NM_002188 |
| IL5 | NM_000879 |
| IL5RA | NM_000564 |
| IL8 | NM_000584 |
| IL8RA | NM_000634 |
| IL8RB | NM_001557 |
| CXCL6 | NM_002993 |
| ABCF1 | NM_001090 |
| IL9 | NM_000590 |

FIG. 11 (continued)

| GL4 | | GL5 | |
|---|---|---|---|
| Symbol | Ref Seq | Symbol | Ref Seq |
| COL1A1 | NM_000088 | TMEM2 | NM_013390 |
| B2M | NM_004048 | MYC | NM_002467 |
| PPIA | NM_021130 | FGFR3 | NM_022965 |
| HPRT1 | NM_000194 | PODXL | NM_001018111 |
| TFRC | NM_003234 | SMAD6 | NM_005585 |
| DPPA4 | NM_018189 | CALM1 | NM_006888 |
| AFP | NM_001134 | TMED1 | NM_006858 |
| DNMT3B | NM_006892 | ASB13 | NM_024701 |
| GDF3 | NM_020634 | LEF1 | NM_016269 |
| LEFTY1 | NM_020997 | FEZ2 | NM_005102 |
| OTX2 | NM_021728 | PGM1 | NM_002633 |
| PODXL | NM_005397 | MRPL54 | NM_172251 |
| TDGF1 | NM_003212 | DIMT1L | NM_014473 |
| AHNAK | NM_024060 | SMAD3 | NM_005902 |
| BMP1 | NM_006129 | MKX | NM_173576 |
| BMP7 | NM_001719 | SCD5 | NM_001037582 |
| CALD1 | NM_004342 | MTSS1 | NM_014751 |
| CAMK2N1 | NM_018584 | CA2 | NM_000067 |
| CAV2 | NM_001233 | CCND2 | NM_001759 |
| CDH2 | NM_001792 | LAPTM4B | NM_018407 |
| COL1A2 | NM_000089 | NAV2 | NM_145117 |
| COL3A1 | NM_000090 | HSPA12A | NM_025015 |
| COL5A2 | NM_000393 | SORBS2 | NM_003603 |
| DSC2 | NM_004949 | C3orf31 | NM_138807 |
| DSP | NM_004415 | MT1A | NM_005946 |
| EGFR | NM_005228 | C5orf13 | NM_004772 |
| ERBB3 | NM_001982 | AKT1 | NM_001014431 |
| ESR1 | NM_000125 | MKKS | NM_170784 |
| FGFBP1 | NM_005130 | MTP18 | NM_016498 |
| FZD7 | NM_003507 | DPM3 | NM_153741 |
| GNG11 | NM_004126 | ILK | NM_004517 |
| IGFBP4 | NM_001552 | WDR54 | NM_032118 |
| ILK | NM_004517 | PEMT | NM_148172 |
| JAG1 | NM_000214 | DPYSL2 | NM_001386 |
| MAP1B | NM_005909 | CNTNAP2 | NM_014141 |
| MITF | NM_000248 | CHSY1 | NM_014918 |
| MST1R | NM_002447 | ICK | NM_016513 |
| NODAL | NM_018055 | NEFL | NM_006158 |
| NOTCH1 | NM_017617 | RPRML | NM_203400 |
| NUDT13 | NM_015901 | PIGY | NM_001042616 |
| PDGFRB | NM_002609 | MRFAP1 | NM_033296 |
| PLEK2 | NM_016445 | FAM125B | NM_033446 |
| PTK2 | NM_005607 | NUAK1 | NM_014840 |
| PTP4A1 | NM_003463 | CYP4V2 | NM_207352 |
| RAC1 | NM_006908 | HES5 | NM_001010926 |
| RGS2 | NM_002923 | FTSJ1 | NM_012280 |
| SIP1 | NM_003616 | TMEM98 | NM_001033504 |
| SMAD2 | NM_005901 | GARNL4 | NM_015085 |
| SNAI1 | NM_005985 | CCND1 | NM_053056 |

FIG. 11 (continued)

| GL4 | |
|---|---|
| Symbol | Ref Seq |
| SNAI2 | NM_003068 |
| SNAI3 | NM_178310 |
| SOX10 | NM_006941 |
| STAT3 | NM_003150 |
| TCF3 | NM_003200 |
| TCF4 | NM_003199 |
| TGFB1 | NM_000660 |
| TGFB2 | NM_003238 |
| TGFB3 | NM_003239 |
| TMEFF1 | NM_003692 |
| TMEM132A | NM_178031 |
| TSPAN13 | NM_014399 |
| VPS13A | NM_033305 |
| WNT5A | NM_003392 |
| WNT5B | NM_032642 |
| ZEB1 | NM_030751 |
| ABL1 | NM_005157 |
| AKT1 | NM_005163 |
| BCL2L1 | NM_138578 |
| BIRC8 | NM_033341 |
| BNIP1 | NM_001205 |
| CASP14 | NM_012114 |
| CASP5 | NM_004347 |
| CASP6 | NM_032992 |
| CASP8 | NM_001228 |
| TNFSF5 | NM_000074 |
| CIDEA | NM_001279 |
| DFFA | NM_004401 |
| TNFSF6 | NM_000639 |
| LTBR | NM_002342 |
| RIPK2 | NM_003821 |
| TNFRSF10A | NM_003844 |
| TNFRSF9 | NM_001561 |
| TNFSF7 | NM_001242 |
| TNFSF8 | NM_001244 |
| TP53 | NM_000546 |
| CCL21 | NM_002989 |
| CHEK2 | NM_007194 |
| CSF2 | NM_000758 |
| CYP7A1 | NM_000780 |
| DDB1 | NM_001923 |
| E2F1 | NM_005225 |
| EPHX2 | NM_001979 |
| FMO1 | NM_002021 |
| GDF15 | NM_004864 |
| GSR | NM_000637 |

| GL5 | |
|---|---|
| Symbol | Ref Seq |
| LOC653506 | XM_927769 |
| HCFC1R1 | NM_001002018 |
| FAM44B | NM_138369 |
| CXADR | NM_001338 |
| IGFBP5 | NM_000599 |
| TARBP2 | NM_134323 |
| EYA2 | NM_172112 |
| CERK | NM_022766 |
| PRMT6 | NM_018137 |
| SH3D19 | NM_001009555 |
| PHB | NM_002634 |
| THOC7 | NM_025075 |
| REEP5 | NM_005669 |
| FAM134B | NM_001034850 |

Figure 12, HBV subtype alignment

```
HBV_design_seq_subtype_ayr   GAGGCATACTTCAAAGACTGTTTGTTTAAAGACTGGGAGGAGTTGGGGGA
HBV_ref_genotype_A           GAGGCCTACTTCAAAGACTGTGTGTTTAAGGACTGGGAGGAGCTGGGGGA
HBV_ref_genotype_B           GAGGCATACTTCAAAGACTGTGTGTTTAATGAGTGGGAGGAGTTGGGGGA
HBV_ref_genotype_C           GAGGCATACTTCAAAGACTGCTTGTTTAAAGACTGGGAGGAGTTGGGGGA
HBV_ref_genotype_D           GAGGCATACTTCAAAGACTGTTTGTTTAAAGACTGGGAGGAGTTGGGGGA
HBV_ref_genotype_E           GAGGCATACTTCAAAGACTGTTTGTTTAAAGACTGGGAGGAGTTGGGGGA
HBV_ref_genotype_F           -----ATACATCAAAGACTGTGTGTTTAAAGACTGGGAGGAGTTGGGGGA
HBV_ref_genotype_G           -----ATACTTCAAGGACTGTGTTTTTGCTGAGTGGGAAGAATTAGGCAA
HBV_ref_genotype_H           GAGGAATACATCAAAGACTGTGTATTTAAGGACTGGGAGGAGTCGGGGGA
                                  ***  **** *****  *  ***    ** *****  **   **   *

HBV_design_seq_subtype_ayr   GGAGATTAGGTTAAAGGTCTTTGTACTAGGAGGCTGTAGGCATAAATTGG
HBV_ref_genotype_A           GGAGATTAGGTTAAAGGTCTTTGTATTAGGAGGCTGTAGGCATAAATTGG
HBV_ref_genotype_B           GGAGATTAGGTTAAAGGTCTTTGTACTAGGAGGCTGTAGGCATAAATTGG
HBV_ref_genotype_C           GGAGATTAGGTTAAAGGTCTTTGTACTAGGAGGCTGTAGGCATAAATTGG
HBV_ref_genotype_D           GGAGATTAGATTAAAGGTCTTTGTACTAGGAGGCTGTAGGCATAAATTGG
HBV_ref_genotype_E           GGAGACTAGATTAATGATCTTTGTACTAGGAGGCTGTAGGCATAAATTGG
HBV_ref_genotype_F           GGAGACCAGGTTAATGATCTATGTACTAGGAGGCTGTAGGCATAAATTGG
HBV_ref_genotype_G           TGAGTCCAGGTTAATGACCTTTGTATTAGGAGGCTGTAGGCATAAATTGG
HBV_ref_genotype_H           GGAGTTGAGGTTAAAGGTCTTTGTATTAGGAGGCTGTAGGCATAAATTGG
                             ***   **  ****  *   ** **** ************************

HBV_design_seq_subtype_ayr   TCTGTTCACCAGCACCATGCAACTTTTTCCCCTCTGCCTAATCATCTCAT
HBV_ref_genotype_A           TCTGCGCACCAGCACCATGCAACTTTTTCACCTCTGCCTAATCATCTCTT
HBV_ref_genotype_B           TCTGTTCACCAGCACCATGCAACTTTTTCACCTCTGCCTAATCATCTCAT
HBV_ref_genotype_C           TCTGTTCACCAGCACCATGCAACTTTTTCACCTCTGCCTAATCATCTCAT
HBV_ref_genotype_D           TCTGCGCACCAGCACCATGCAACTTTTTCACCTCTGCCTAATCATCTCTT
HBV_ref_genotype_E           TCTGCGCACCAGCACCATGCAACTTTTTCACCTCTGCCTAATCATCTCTT
HBV_ref_genotype_F           TCTGTTCACCAGCACCATGCAACTTTTTCACCTCTGCCTAATCATCTTTT
HBV_ref_genotype_G           TCTGCGCACCAGCACCATGTAACTTTTTCACCTCTGCCTAATCATCTCTT
HBV_ref_genotype_H           TCTGTTCACCAGCACCATGCAACTTTTTCACCTCTGCCTAATCATCTTTT
                             ****  ************* ********  ******************  *

HBV_design_seq_subtype_ayr   GTTCATGTCCTACTGTTCAAGCCTCCAAGCTGTG
HBV_ref_genotype_A           GTACATGTCCCACTGTTCAAGCCTCCAAGCTGTG
HBV_ref_genotype_B           GTTCATGTCCTACTGTTCAAGCCTCCAAGCTGTG
HBV_ref_genotype_C           GTTCATGTCCTACTGTTCAAGCCTCCAAGCTGTG
HBV_ref_genotype_D           GTTCATGTCCTACTGTTCAAGCCTCCAAGCTGTG
HBV_ref_genotype_E           GTTCATGTCCTACTGTTCAAGCCTCCAAGCTGTG
HBV_ref_genotype_F           GTTCATGTCCTACTGTTCAAGCCTCCAAGCTGTG
HBV_ref_genotype_G           GTTCATGTCCTACTGTTCAAGCCTCCAAGCTGTG
HBV_ref_genotype_H           GTTCATGTCCCACTGTTCAAGCCTCCAAGCTGTG
                             **  ******  **********************
```

<u>Legend</u>

Limiting primer(forward primer) region (TTAAAGACTGGGAGGAGTTG, underlined)

Regular primer(reverse primer) region (CTCTGCCTAATCATCTCATGT , underlined)

Partzyme A detecting region (AGGTCTTTGTACTAGGAGG, bold)

Partzyme B detecting region (CTGTAGGCATAAATTGGTCT, bold italics)

Figure 13, HCV subtype alignment

```
HCV_design_seq_genotype_1   CGCAGAAAGCGTCTAGCCATGGCGTTAGTATGAGTGTCGTGCAGCCTCCA
HCV_CON_genotype_1a         CGCAGAAAGCGTCTAGCCATGGCGTTAGTATGAGTGTCGTGCAGCCTCCA
HCV_CON_genotype_1b         CGCAGAAAGCGTCTAGCCATGGCGTTAGTATGAGTGTCGTGCAGCCTCCA
HCV_CON_genotype_1c         CGCAGAAAGCGTCTAGCCATGGCGTTAGTATGAGTGTCGTGCAGCCTCCA
HCV_CON_genotype_2a         CGCAGAAAGCGTCTAGCCATGGCGTTAGTATGAGTGTCGTACAGCCTCCA
HCV_CON_genotype_2b         CGCAGAAAGCGTCTAGCCATGGCGTTAGTATGAGTGTCGTACAGCCTCCA
HCV_CON_genotype_3          CGCGGAAAGCGCCTAGCCATGGCGTTAGTACGAGTGTCGTGCAGCCTCCA
HCV_CON_genotype_4          CGCAGAAAGCGTCTAGCCATGGCGTTAGTATGAGTGTTGTACAGCCTCCA
HCV_Ref_genotype_5          CGCAGAAAGCGTCTAGCCATGGCGTTAGTATGAGTGTCGAACAGCCTCCA
HCV_CON_genotype_6          CGCAGAAAGCGTCTAGCCATGGCGTTAGTATGAGTGTCGTGCAGCCTCCA
                            *** ******* ****************** ****** *  *********

HCV_design_seq_genotype_1   GGACCCCCCCTCCCGGGAGAGCCATAGTGGTCTGCGGAACCGGTGAGTAC
HCV_CON_genotype_1a         GGACCCCCCCTCCCGGGAGAGCCATAGTGGTCTGCGGAACCGGTGAGTAC
HCV_CON_genotype_1b         GGACCCCCCCTCCCGGGAGAGCCATAGTGGTCTGCGGAACCGGTGAGTAC
HCV_CON_genotype_1c         GGACCCCCCCTCCCGGGAGAGCCATAGTGGTCTGCGGAACCGGTGAGTAC
HCV_CON_genotype_2a         GGCCCCCCCCTCCCGGGAGAGCCATAGTGGTCTGCGGAACCGGTGAGTAC
HCV_CON_genotype_2b         GGCCCCCCCCTCCCGGGAGAGCCATAGTGGTCTGCGGAACCGGTGAGTAC
HCV_CON_genotype_3          GGACCCCCCCTCCCGGGAGAGCCATAGTGGTCTGCGGAACCGGTGAGTAC
HCV_CON_genotype_4          GGACCCCCCCTCCCGGGAGAGCCATAGTGGTCTGCGGAACCGGTGAGTAC
HCV_Ref_genotype_5          GGACCCCCCCTCCCGGGAGAGCCATAGTGGTCTGCGGAACCGGTGAGTAC
HCV_CON_genotype_6          GGACCCCCCCTCCCGGGAGAGCCATAGTGGTCTGCGGAACCGGTGAGTAC
                            ** ***********************************************

HCV_design_seq_genotype_1   ACCGGAATTGCCAGGACGACCGGGTCCTTTCTTGGAT-AAACCCGCTCAA
HCV_CON_genotype_1a         ACCGGAATTGCCAGGACGACCGGGTCCTTTCTTGGAT-AAACCCGCTCAA
HCV_CON_genotype_1b         ACCGGAATTGCCAGGACGACCGGGTCCTTTCTTGGAT-CAACCCGCTCAA
HCV_CON_genotype_1c         ACCGGAATTGCCAGGACGACCGGGTCCTTTCTTGGAT-AAACCCGCTCAA
HCV_CON_genotype_2a         ACCGGAATTGCCGGGAAGACTGGGTCCTTTCTTGGAT-AAACCCACTCTA
HCV_CON_genotype_2b         ACCGGAATTACCGGAAAGACTGGGTCCTTTCTTGGAT-AAACCCACTCTA
HCV_CON_genotype_3          ACCGGAATCGCTGGGGTGACCGGGTCCTTTCTTGGAA-CAACCCGCTCAA
HCV_CON_genotype_4          ACCGGAATCGCCAGGACGACCGGGTCCTTTCTTGGATTAAACCCGCTCAA
HCV_Ref_genotype_5          ACCGGAATTGCCGGGATGACCGGGTCCTTTCTTGGATAAAACCCGCTCAA
HCV_CON_genotype_6          ACCGGAATTGCCAGGACGACCGGGTCCTTTCTTGGAT-CAACCCGCTCAA
                            ********  *  *   *** ****************   ***** *** *

HCV_design_seq_genotype_1   TGCCTGGAGATTTGGGCG
HCV_CON_genotype_1a         TGCCTGGAGATTTGGGCG
HCV_CON_genotype_1b         TGCCTGGAGATTTGGGCG
HCV_CON_genotype_1c         TGCCTGGAGATTTGGGCG
HCV_CON_genotype_2a         TGCCCGGCCATTTGGGCG
HCV_CON_genotype_2b         TGTCCGGTCATTTGGGCG
HCV_CON_genotype_3          TACCCAGAAATTTGGGCG
HCV_CON_genotype_4          TGCCTGGAAATTTGGGCG
HCV_Ref_genotype_5          TGCCCGGAGATTTGGGCG
HCV_CON_genotype_6          TGCCTGGAGATTTGGGCG
                            *  *  *  *********
```

Legend

Limiting primer(forward primer) region (GGCGTTAGTATGAGTGTCGTG, underlined)

Regular primer(reverse primer) region (CTTTCTTGGAT-AAACCCGCTC, underlined)

Partzyme A detecting region (ATAGTGGTCTGCGGAACCG, bold)

Partzyme B detecting region (GTGAGTACACCGGAATTGCC, bold italics)

Figure 14A, HIV-1 subtype alignment

```
HIV-1_design_seq_CON_B        GCAGGAACTACTAGTACCCTTCAGGAACAAATAGGATGGATGACAAA---
HIV-1_M_group_concensus       GCAGGAACTACTAGTACCCTTCAGGAACAAATAGGATGGATGACAAG---
HIV-1_M_group_CONSENSUS_A1    GCAGGAACTACTAGTACCCCTCAAGAACAAATAGGATGGATGACAGG---
HIV-1_M_group_CONSENSUS_A2    GCAGGAACTACTAGTACCCTTCAGGAACAAATAGGATGGATGACCAG---
HIV-1_M_group_CONSENSUS_B     GCAGGAACTACTAGTACCCTTCAGGAACAAATAGGATGGATGACAAA---
HIV-1_M_group_CONSENSUS_C     GCAGGAACTACTAGTACCCTTCAGGAACAAATAGCATGGATGACAAG---
HIV-1_M_group_CONSENSUS_D     GCAGGAACTACTAGTACCCTTCAGGAACAAATAGGATGGATGACAAG---
HIV-1_M_group_CONSENSUS_F1    ---GGAACTACTAGTACCCTTCAGGAACAAATACAATGGATGACAAG---
HIV-1_M_group_CONSENSUS_G     GCAGGAACTACTAGTACCCTGCAGGAACAAATAAGATGGATGACCAG---
HIV-1_M_group_CONSENSUS_H     GCAGGAACTACTAGTACCCTTCAGGAACAAATAGCATGGATGACAGG---
HIV-1_M_group_CONSENSUS_K     GCAGGAACTACCAGCACCCTTCAGGAACAAATAACATGGATGACAAG---
HIV-1_N_group_Ref             GCAGGGACAACTAGTACTCTGGCAGAACAGGTGGCATGGATGACTTC---
HIV-1_O_group_Ref             GCTGGGACAACTAGCACCCAGCAAGAGCAAATTCACTGGACTACCAGGCC
                               **  **  **  **  **   *       **  **   *     ****  **

HIV-1_design_seq_CON_B        TAATCCACCTATCCCAGTAGGAGAAATCTATAAAAGATGGATAATCCTGG
HIV-1_M_group_concensus       CAACCCACCTATCCCAGTGGGAGAAATCTATAAAAGATGGATAATCCTGG
HIV-1_M_group_CONSENSUS_A1    CAACCCACCTATCCCAGTGGGAGACATCTATAAAAGATGGATAATCCTGG
HIV-1_M_group_CONSENSUS_A2    CAACCCACCCATCCCAGTGGGAGAAATTTATAAAAGATGGATAATCCTGG
HIV-1_M_group_CONSENSUS_B     TAATCCACCTATCCCAGTAGGAGAAATCTATAAAAGATGGATAATCCTGG
HIV-1_M_group_CONSENSUS_C     TAACCCACCTATTCCAGTGGGAGACATCTATAAAAGATGGATAATTCTGG
HIV-1_M_group_CONSENSUS_D     CAATCCACCTATCCCAGTAGGAGAAATCTATAAAAGATGGATAATCCTGG
HIV-1_M_group_CONSENSUS_F1    CAACCCACCTGTCCCAGTGGGAGACATCTATAAAAGATGGATCATCCTAG
HIV-1_M_group_CONSENSUS_G     CAACCCACCTATCCCAGTGGGAGAAATTTATAAAAGATGGATAATCCTGG
HIV-1_M_group_CONSENSUS_H     CAATCCACCTATCCCAGTGGGAGACATCTATAAAAGATGGATAATCCTGG
HIV-1_M_group_CONSENSUS_K     CAACCCACCTGTCCCAGTGGGAGAAATCTATAAAAGATGGATAATCCTGG
HIV-1_N_group_Ref             TAATCCTCCTATTCCAGTAGGAGATATTTATAGAAGATGGATAGTTCTGG
HIV-1_O_group_Ref             CAACCAACCTATCCCAGTAGGAGACATCTATAGAAAATGGATAGTGTTAG
                               **  *  **   *  *****  *****  **  ****  **  ******      *   *  *

HIV-1_design_seq_CON_B        GATTAAATAAAATAGTAAGAATGTATAGCCCTACCAGCATTCTGGACATA
HIV-1_M_group_concensus       GATTAAATAAAATAGTAAGAATGTATAGCCCTGTCAGCATTTTGGACATA
HIV-1_M_group_CONSENSUS_A1    GATTAAATAAAATAGTAAGAATGTATAGCCCTGTTAGCATTTTGGATATA
HIV-1_M_group_CONSENSUS_A2    GATTAAATAAAATAGTAAGAATGTATAGCCCTGTCAGCATTTTGGACATA
HIV-1_M_group_CONSENSUS_B     GATTAAATAAAATAGTAAGAATGTATAGCCCTACCAGCATTCTGGACATA
HIV-1_M_group_CONSENSUS_C     GGTTAAATAAAATAGTAAGAATGTATAGCCCTGTCAGCATTTTGGACATA
HIV-1_M_group_CONSENSUS_D     GATTAAATAAAATAGTAAGAATGTATAGCCCTGTCAGCATTTTGGACATA
HIV-1_M_group_CONSENSUS_F1    GATTAAATAAAATAGTAAGAATGTATAGCCCTGTCAGCATTTTGGACATA
HIV-1_M_group_CONSENSUS_G     GATTAAATAAAATAGTAAGAATGTATAGCCCTGTCAGCATTTTGGACATA
HIV-1_M_group_CONSENSUS_H     GATTAAATAAGATAGTAAGAATGTATAGTCCTGTCAGCATTCTGGACATA
HIV-1_M_group_CONSENSUS_K     GTTTAAATAAAATAGTAAGAATGTATAGCCCTGTCAGCATTTTGGACATA
HIV-1_N_group_Ref             GGTTAAACAGAATTGTGAGAATGTATAGTCCTGTCAGCATTCTAGAGATC
HIV-1_O_group_Ref             GACTAAACAAAATGGTAAAAATGTACAGCCCAGTGAGCATCTTAGATATT
                               *  ****  *  **  **  *  ******  **  **     *****   *  **  **
```

Figure 14B, HIV-1 subtype alignment (continued)

```
HIV-1_design_seq_CON_B        AGACAAGGACCAAAGG
HIV-1_M_group_concensus       AGACAAGGGCCAA--A
HIV-1_M_group_CONSENSUS_A1    AAACAAGGGCCAA--A
HIV-1_M_group_CONSENSUS_A2    AGACAAGGGCCAA--A
HIV-1_M_group_CONSENSUS_B     AGACAAGGACCAAAGG
HIV-1_M_group_CONSENSUS_C     AAACAAGGGCCAAAGG
HIV-1_M_group_CONSENSUS_D     AGACAAGGACCAAAGG
HIV-1_M_group_CONSENSUS_F1    AGACAAGGGCCAA--A
HIV-1_M_group_CONSENSUS_G     AGACAAGGGCCAA--A
HIV-1_M_group_CONSENSUS_H     AAACAAGGGCCAA--A
HIV-1_M_group_CONSENSUS_K     AGACAAGGGCCAA--A
HIV-1_N_group_Ref             AAGCAAGGACCAA--A
HIV-1_O_group_Ref             AAGCAGGGACCAAAGG
                               *  ** **  ****
```

Legend

Limiting primer(forward primer) region (CAGGAACAAATAGGATGGATG, underlined)

Regular primer(reverse primer) region (GTATAGCCCTACCAGCATTCT, underlined)

Partzyme A detecting region (ACAAATAATCCACCTATCC, bold)

Partzyme B detecting region (*CAGTAGGAGAAATCTATAAAAGA*, bold italics)

FIG. 15A

| Gene Symbol | Entrez Gene ID | Limiting Primer | SEQ ID NO: | Regular Primer | SEQ ID NO: |
|---|---|---|---|---|---|
| BCL2L1 | 598 | TCCCTTTCCTTCCATCCCTAC | 41 | CCTGGTCCTTGCATCTTTATC | 42 |
| BIRC2 | 329 | AGATAGGGTAGCCTGCTTTGC | 45 | GCTGAACTGGAACACTAGATG | 46 |
| CCND1 | 595 | AACAAGCTCAAGTGGAACCTG | 49 | ACAGAGGGCAACGAAGGTC | 50 |
| PRDM1 | 639 | TCACTGTTGGTGGCATACTTG | 53 | GAGGCTGAGTTTGAAGAGAAG | 54 |
| CCNE1 | 898 | AGTACCCACAATGAGTCAAAG | 57 | TGATGGAATTAACACAGAAGC | 58 |
| CDK4 | 1019 | TCTCTGAGGCTATGGAGGGTC | 61 | TATAAAGGTAGGGAAAGGGAC | 62 |
| EGFR | 1956 | AGGAGGTGGCTGGTTATGTC | 65 | TGCATCATAGTTAGATAAGACTGC | 66 |
| EMSY / C11orf30 | 56946 | GTAGAACTGCTGCTGCCACTG | 69 | ATTCTCTCCAAATCCCATAAC | 70 |
| ERBB2 | 2064 | TGAAGTACCACCTCCCGAG | 73 | CATAAGCCAAATTCTGTGC | 74 |
| FGFR1 | 2260 | CTGTACCTGGAGATCATCATC | 77 | ATCGGCTGTGGAAGTCACTC | 78 |
| HMGA2 | 8091 | ACTCACTCTAGGCACATGCAG | 81 | TGAAATCAAACCACACCATAG | 82 |
| MET | 4233 | AGACAAATAGGAGCCAGCCTG | 85 | CTTGTTGAAGAAGTCGTTGAC | 86 |
| MYC | 4609 | ATACATCCTGTCCGTCCAAGC | 89 | ACAAGAGTTCCGTAGCTGTTC | 90 |
| PIK3CA | 5290 | TTCTTCCCTTTCTGCTTCTTG | 93 | ACTTTAGAATGCCTCCGTGAG | 94 |
| VEGFA | 7422 | CACTCACACACACACAACCAG | 97 | CACATTGTTGGAAGAAGCAGC | 98 |
| YWHAZ | 7534 | AACATTGTCCCTGCTCTTGAG | 101 | TCCTCTTTCTTCCTCCTCTATTC | 102 |
| ZNF217 | 7764 | CCAATGAGTGTTACAGAGAGC | 105 | TCCAGCATAATACAAATCGAC | 106 |
| REL | 5966 | CTGTTACGGGTTCTGTGATAG | 109 | TTGTGTTGAACGATTGGGAAG | 110 |
| CDKN2A | 1029 | CATTCATGTGGGCATTTCTTG | 113 | TTATTTGAGCTTTGGTTCTGC | 114 |
| CSMD1 | 64478 | CAGAGTTGTGTCAAACCTCAC | 117 | TTCAATACAATGGCTATGCTG | 118 |
| FHIT | 2272 | CCTGTCTGAGCCGTTTAGGTC | 121 | CAGTTTCTTCATCTCACCATC | 122 |
| PTEN | 5728 | ATGTGGAGGCTATCAACAAAG | 125 | CCACAGCAGGTATTATGATTG | 126 |
| PTPRD | 5789 | AGCATCGGGAGGGTTACAG | 129 | AGAGAAGTGAGACAATTCCAG | 130 |
| RB1 | 5925 | CCTTCTGTCTGAGCACCCAG | 133 | GTCCAAATGCCTGTCTCTC | 134 |
| RPP40 (reference gene) | 10799 | ATTGCTGTCCTGAGCCAAG | 137 | CAGAGATGTTCCAATAGGAGAC | 138 |

| Probe | Sequence | |
|---|---|---|
| Sub2-FAM | /56-FAM/AAGGTTTCCTCrGrUCCCTGGGCA/3BHQ_1/ | 141 |
| Sub6-HEX | /5HEX/ATCACGCCTCrGrUTCCTCCCAG/3BHQ_1/ | 142 |

FIG. 15B

| Gene Symbol | Partzyme A | SEQ ID NO: |
|---|---|---|
| BCL2L1 | CCTAAGAGCCATTTAGGGGACAACGAGAGGAAACCTT | 43 |
| BIRC2 | AGCATGCAGACACATGCAGACAACGAGAGGAAACCTT | 47 |
| CCND1 | CTCTCCAAAATGCCAGAGGACAACGAGAGGAAACCTT | 51 |
| PRDM1 | ATCAGCACCAGAATCCCAGACAACGAGAGGAAACCTT | 55 |
| CCNE1 | ATCCATTTATTTAATGGTGGACAACGAGAGGAAACCTT | 59 |
| CDK4 | TCCCACCTCTCCTTTTGAGACAACGAGAGGAAACCTT | 63 |
| EGFR | CATTGCCCTCAACACAGTGACAACGAGAGGAAACCTT | 67 |
| EMSY / C11orf30 | TAACAACTGGTGGCTTCTGACAACGAGAGGAAACCTT | 71 |
| ERBB2 | GAGGTAGAGTGGTGAACAGACAACGAGAGGAAACCTT | 75 |
| FGFR1 | CTCATCTCCTGCATGGTGGACAACGAGAGGAAACCTT | 79 |
| HMGA2 | TTAGAGAGTAGAGGGTGGGACAACGAGAGGAAACCTT | 83 |
| MET | ATTCTTTTCGGGGTGTTCGACAACGAGAGGAAACCTT | 87 |
| MYC | CTGAAGAGGACTTGTTGCGACAACGAGAGGAAACCTT | 91 |
| PIK3CA | TGAAGAAGTTGATGGAGGGACAACGAGAGGAAACCTT | 95 |
| VEGFA | GTGGTTTCAATGGTGTGAGACAACGAGAGGAAACCTT | 99 |
| YWHAZ | TGAGCTTTGGGTATAACTTAGACAACGAGAGGAAACCTT | 103 |
| ZNF217 | GGGTATGTGATAATAGAGGGACAACGAGAGGAAACCTT | 107 |
| REL | AAACAATGGCTACTTGACGACAACGAGAGGAAACCTT | 111 |
| CDKN2A | AACTAGGGAAGCTCAGGGGACAACGAGAGGAAACCTT | 115 |
| CSMD1 | AAGTTTGTATCATACATGGGACAACGAGAGGAAACCTT | 119 |
| FHIT | AGTTGGAGTGACCGAGGTGACAACGAGAGGAAACCTT | 123 |
| PTEN | ATCTCCTGTGTAATCAAGGACAACGAGAGGAAACCTT | 127 |
| PTPRD | GAAAGCTAGAAAAGGTGTAGGACAACGAGAGGAAACCTT | 131 |
| RB1 | CATCTGGACCCTTTTCCAGACAACGAGAGGAAACCTT | 135 |
| RPP40 (reference gene) | CTTATTTGTGTACAATCACTGACAACGAGAGGCGTGAT | 139 |

FIG. 15C

| Gene Symbol | Partzyme B | SEQ ID NO: |
|---|---|---|
| BCL2L1 | TGCCCAGGGAGGCTAGCTCCACTTTTGACTAGGGATTC/3Phos/ | 44 |
| BIRC2 | TGCCCAGGGAGGCTAGCTCTCGAATGAGAACATTTATGTACTG/3Phos/ | 48 |
| CCND1 | TGCCCAGGGAGGCTAGCTCGGAGGAGAACAAACAGATC/3Phos/ | 52 |
| PRDM1 | TGCCCAGGGAGGCTAGCTGGGTGGTCGTTCACAATGTA/3Phos/ | 56 |
| CCNE1 | TGCCCAGGGAGGCTAGCTGTGGGAGTTGTGTTCTTTT/3Phos/ | 60 |
| CDK4 | TGCCCAGGGAGGCTAGCTGCTTCTCCTTCTCCTTCCCA/3Phos/ | 64 |
| EGFR | TGCCCAGGGAGGCTAGCTGAGCGAATTCCTTTGGAAAA/3Phos/ | 68 |
| EMSY / C11orf30 | TGCCCAGGGAGGCTAGCTGGTTGTAGAAGCAATGACTG/3Phos/ | 72 |
| ERBB2 | TGCCCAGGGAGGCTAGCTGACAGCAAAGGTTCTACCC/3Phos/ | 76 |
| FGFR1 | TGCCCAGGGAGGCTAGCTGGTCGGTCATCGTCTACAAG/3Phos/ | 80 |
| HMGA2 | TGCCCAGGGAGGCTAGCTCTGAACTCCAGTTACTCTCG/3Phos/ | 84 |
| MET | TGCCCAGGGAGGCTAGCTCACAAAGCAAGCCAGATTCT/3Phos/ | 88 |
| MYC | TGCCCAGGGAGGCTAGCTGAAACGACGAGAACAGTTGA/3Phos/ | 92 |
| PIK3CA | TGCCCAGGGAGGCTAGCTGGTATTTTCTTGCTTCTTTAAA/3Phos/ | 96 |
| VEGFA | TGCCCAGGGAGGCTAGCTGACATAGGTCCTTTTAGGCT/3Phos/ | 100 |
| YWHAZ | TGCCCAGGGAGGCTAGCTCCCCATCATTATTTAGAGA/3Phos/ | 104 |
| ZNF217 | TGCCCAGGGAGGCTAGCTCTGGAATTTAAACCTGTATT/3Phos/ | 108 |
| REL | TGCCCAGGGAGGCTAGCTGTGTACATCAGCTTGTGAAA/3Phos/ | 112 |
| CDKN2A | TGCCCAGGGAGGCTAGCTGGTTACTGGCTTCTCTTGAG/3Phos/ | 116 |
| CSMD1 | TGCCCAGGGAGGCTAGCTGTTTTCAAACGATGCTTGT/3Phos/ | 120 |
| FHIT | TGCCCAGGGAGGCTAGCTGGGGATCACTGGTTGAAGAA/3Phos/ | 124 |
| PTEN | TGCCCAGGGAGGCTAGCTCCAGTGCTAAAATTCAGATG/3Phos/ | 128 |
| PTPRD | TGCCCAGGGAGGCTAGCTGTGTTCTGGAACACCATGAT/3Phos/ | 132 |
| RB1 | TGCCCAGGGAGGCTAGCTCACACCCTGCAGAATGAGTA/3Phos/ | 136 |
| RPP40 (reference gene) | CTGGGAGGAAGGCTAGCTGCTTCATACTTCCAGAGAAG/3Phos/ | 140 |

FIG. 16.
A)
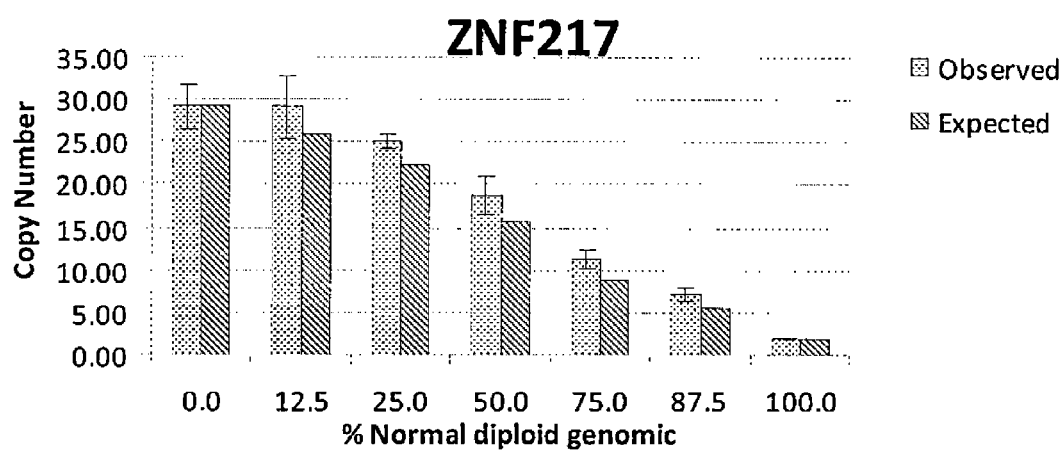
B)
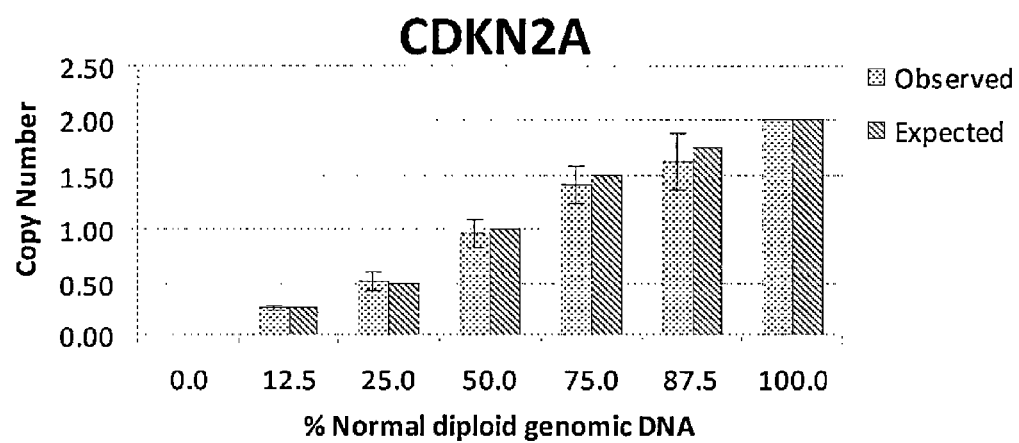

METHODS AND COMPOSITIONS FOR NUCLEIC ACID DETECTION

RELATED APPLICATION DISCLOSURE

This application claims the benefit of U.S. Provisional Application Ser. No. 61/381,815, filed Sep. 10, 2010, entitled "Methods and Compositions for Nucleic Acid Detection," which is incorporated by reference herein in its entirety.

This application includes as part of its disclosure a biological sequence listing in a file named "43277o1002v4.txt" and having a size of 30,895 bytes, which was created Mar. 9, 2015, which is hereby incorporated by reference in its entirety.

FIELD

The present application relates to Multicomponent Nucleic Acid Enzymes (MNAzymes), which may be used for detecting, identifying and/or quantifying targets. More particularly, this application provides methods of designing and making more reliable MNAzymes, as well as compositions comprising MNAzyme components and methods of using MNAzymes.

BACKGROUND

Multicomponent Nucleic Acid Enzymes (MNAzymes) are made of enzymatically inactive subunits that assemble to form an active enzyme in the presence of an assembly facilitator (see US 2011/0143338; US 2007/0231810; WO/2008/122084; WO/2007/041774; and Mokany et al., J Am Chem. Soc. 2010 Jan. 27; 132(3): 1051-1059, each of which is incorporated by reference in its entirety). Because the inactive subunits form the active enzyme in the presence of the assembly facilitator, but remain separate and inactive in its absence, enzyme activity is specifically activated by the presence of the assembly facilitator. The active enzyme can generate a detectable signal that indicates the presence of the assembly facilitator, or catalyze another desired reaction. In general, the inactive subunits, or partzymes, each include a sensor arm, which interacts with the assembly facilitator, and may also include a substrate recognition arm which interacts with the enzyme's substrate.

In one particularly useful configuration, the assembly facilitator is a nucleic acid, and the partzymes each include a sensor arm containing part of a complementary nucleic acid, such that base pairing brings the inactive subunits together to form the active enzyme. The active enzyme may cleave a substrate that contains a fluorophore and a matched quencher, resulting in increased fluorescence and permitting qualitative or quantitative detection of the assembly facilitator. For example, the MNAzyme may be utilized for quantitative detection of a nucleic acid produced during a real-time PCR reaction. The substrate may also be a nucleic acid, and the active enzyme may include substrate recognition arms containing complementary nucleic acids which facilitate cleavage of the substrate.

In addition to recognizing the assembly facilitator and substrate through nucleic acids, the active enzyme may itself be made up of catalytically active nucleic acid molecules (and thus, some MNAzymes may be made entirely of nucleic acids). As is well known in the art, nucleic acid molecules can adopt secondary structural configurations which can confer enzymatic or catalytic activity. In vitro evolution technology has facilitated the discovery and development of such catalytic nucleic acids, often referred to as "DNAzymes" or "ribozymes," that are capable of catalyzing a broad range of reactions including cleavage of nucleic acids (Carmi et al, 1996; Raillard and Joyce, 1996; Breaker, 1997; Santoro and Joyce, 1998), ligation of nucleic acids (Cuenoud and Szostak, 1995), porphyrin metallation (Li and Sen, 1996), and the formation of carbon-carbon bonds (Tarasow et al, 1997), ester bonds (Illangasekare et al, 1995) or amide bonds (Lohse and Szostak, 1996).

In particular, DNAzymes and ribozymes have been characterized which specifically cleave distinct nucleic acid sequences after hybridizing via Watson Crick base pairing. DNAzymes are capable of cleaving either RNA (Breaker and Joyce, 1994; Santoro and Joyce, 1997) or DNA (Carmi et al, 1996) molecules. Catalytic RNA molecules (ribozymes) are also able to cleave both RNA (Haseloff and Gerlach, 1988) and DNA (Raillard and Joyce, 1996) sequences. The rate of catalytic cleavage of most nucleic acid enzymes is dependent on the presence and concentration of divalent metal ions such as $Ba^{2+}$, $Sr^{2+}$, $Ca^{2+}$, $Ni^{2+}$, $Co^{2+}$, $Mn^{2+}$, $Zn^{2+}$, and $Pb^{2+}$ (Santoro and Joyce, 1998; Brown et al, 2003).

Catalytic nucleic acids, such as the hammerhead ribozyme and the 10:23 and 8:17 DNAzymes, have multiple domains. They have a conserved catalytic domain (catalytic core) flanked by two non-conserved substrate binding domains ("hybridizing arms"), which are regions of sequence that specifically bind to the substrate. Haseloff and Gerlach engineered the hammerhead ribozyme, which was so named for the stem-loop structure that brings the two conserved domains together forming the catalytic core (Haseloff and Gerlach, 1988). The "10:23" and "8:17" DNAzymes are capable of cleaving nucleic acid substrates at specific RNA phosphodiester bonds (Santoro and Joyce, 1997). The 10:23 DNAzyme has a catalytic domain of 15 deoxynucleotides flanked by two substrate-recognition arms. The 8:17 DNAzyme has a catalytic domain of 14 deoxynucleotides that is also flanked by two substrate-recognition arms.

A catalytic nucleic acid can cleave a nucleic acid substrate with a target sequence that meets minimum requirements. The substrate sequence should be substantially complementary to the hybridizing arms of the catalytic nucleic acid, and the substrate should contain a specific sequence at the site of cleavage. Specific sequence requirements at the cleavage site include, for example, a purine:pyrimidine ribonucleotide sequence for cleavage by the 10:23 DNAzyme (Santoro and Joyce, 1997), and the sequence uridine:X for the hammerhead ribozymes (Perriman et al., 1992), wherein X can equal A, C, or U, but not G.

Catalytic nucleic acids have been shown to tolerate only certain modifications in the area that forms the catalytic core (Perreault et al., 1990; Perreault et al., 1991; Zaborowska et al., 2002; Cruz et al., 2004; Silverman, 2004)). Examples of sequences responsible for catalytic activity of DNAzymes are listed in Table 1.

TABLE 1

Exemplary sequences for some active DNAzymes and their substrates

| DNAzyme type | DNAzyme sequence | Substrate sequence |
|---|---|---|
| 8:17 | $(N)_x$TNNNAGCNNNWCGK$(N)_x$ (SEQ ID NO: 152 and SEQ ID NO: 154) | $(N')_x$ $(rN)_x$ G $(N')_x$ |
| 10:23 | $(N)_x$GGMTMGHNDNNNMGD$(N)_x$ (SEQ ID NO: 153) | $(N')_x$ rR rY $(N')_x$ |

N = A, C, T, G or any analogue; N' = any nucleotide complementary to N; $(N)_x$ or $(N')_x$ = any number of nucleotides; W = A or T; K = A, G or AA; rN = any ribonucleotide base; $(rN)_x$ = any number of ribonucleotides; rR = A or G; rY = C or U; M = A or C; H = A, C or T; D = G, A or T The substitution of certain deoxyribonucleotides for certain ribonucleotides in known ribozymes has been attempted under certain conditions (McCall et al., 1992). Ribozymes that have been fully converted into DNA have had no activity, apparently due to the conformational differences of RNA and DNA (Perreault et al., 1990). These studies demonstrate that RNA enzymes cannot be modified into working DNA enzymes by merely replacing ribonucleotides with deoxyribonucleotides.

There have been some studies which attempted to develop certain homodimeric or heterodimeric ribozymes for therapeutic applications (Kuwabara et al., 1999; Kuwabara et al., 2000; Oshima et al., 2003). In those studies, the catalytic core of the ribozyme comprised solely of ribonucleotides. Moreover, the capacity for DNAzymes to function in dimeric or multimeric formats has not been considered, nor has any information been provided as to how to extrapolate from a dimeric ribozyme to a dimeric DNAzyme in terms of a possible structure of a dimeric DNAzyme and resulting activity.

Catalytic nucleic acids have been used in combination with in vitro amplification protocols as a means of generating a detectable signal, thus allowing real time monitoring of amplified nucleic acid target sequences (Todd et al., 2000) (U.S. Pat. No. 6,140,055; U.S. Pat. No. 6,201,113; WO 99/45146; PCT/IB99/00848; WO 99/50452). Zymogene detection (U.S. Pat. No. 6,140,055; U.S. Pat. No. 6,201,113; WO 99/45146; PCT/IB99/00848; WO 99/50452), also known in the art as DzyNA detection (Todd et al., 2000), results in concurrent target and signal amplification. This occurs because the catalytic DNAzymes or ribozymes co-amplify along with target sequences to produce amplicons that function as true enzymes capable of multiple turnovers. As such, each catalytic nucleic acid amplicon cleaves multiple reporter substrates. The DNAzymes and ribozymes are introduced into the amplicons by using primers with 5' tags that are inactive, anti-sense sequences of catalytic nucleic acids. When these sequences are copied during in vitro amplification the catalytically active sense sequences are co-amplified along with target sequence. The zymogene/DzyNA approach is very flexible since catalytic signal amplification can be linked to target amplification methods including PCR (polymerase chain reaction), strand displacement amplification ("SDA"), or rolling circle amplification ("RCA"), producing DNAzyme amplicons; and nucleic acid sequence-based amplification ("NASBA"), self-sustained sequence replication ("3SR"), or transcription-mediated amplification ("TMA") amplification methods producing ribozyme amplicons. Further, since numerous catalytic nucleic acid molecules with a broad range of catalytic activities have been discovered or evolved, the zymogene approach can use a reporter substrate other than a nucleic acid where the readout of the assay is dependent on a chemical modification other than cleavage of a nucleic acid substrate. The zymogene/DzyNA (Todd et al., 2000) or NASBA/ribozyme (WO 00/58505) approach may be considered sensitive and useful, but there is potential for noise due to amplification of primer sequences.

NASBA has been used to produce RNA amplicons containing target nucleic acid and one section of the catalytic core of the hammerhead ribozyme (GAArA), introduced as antisense sequence tagged to a primer and then copied (WO 00/58505). The additional sequence required for catalytic activity (CUrGANrGrA) was introduced as sense sequence on a second molecule, which was labeled with a fluorophore and quencher, and which also served as the reporter substrate. Certain of the ribonucleotide bases (rN above) must remain as ribonucleotides, or catalytic ribozyme activity is lost. Two molecules consisting entirely of DNA were considered unable to form catalytically active heterodimer enzymes (WO 00/58505).

Catalytic nucleic acids have also been used for detection of single nucleotide polymorphisms ("SNPs"). The strict requirement for Watson Crick base pairing between the catalytic nucleic acid binding arms and the substrate has allowed the development of methods that allow discrimination of closely related short sequences. DNAzymes and ribozymes have been shown to discriminate between two sequences differing by as little as a single base (Cairns et al., 2000) (WO 99/50452).

DNAzymes have properties which provide advantages over ribozymes for certain in vitro applications. DNA is inherently more stable than RNA and hence is more robust with a longer shelf life. DNA can be stored for long periods at room temperature either in solution or in a lyophilized form. DNAzymes also are preferable over the majority of protein enzymes in certain applications because, for example, they are not irreversibly denatured by exposure to high temperatures during amplification.

MNAzymes can be used for nucleic acid quantification in conjunction with real-time polymerase chain reaction (PCR). Real time PCR, also abbreviated as Q-PCR, qPCR, QRT-PCR, or RT-qPCR, is a laboratory technique based on the PCR (polymerase chain reaction), to amplify and simultaneously quantify targeted DNA molecules. It enables both detection and quantification (as absolute copy numbers or relative amount of reference genes) of one or more specific sequences in a DNA sample. The procedure follows the general principle of polymerase chain reaction. The amplified DNA is detected as the reaction progresses in real time. Two other common methods for detection of products in real-time PCR are: (1) sequence-specific DNA probes consisting of oligonucleotides that are labeled with a fluorescent reporter which permits detection only after hybridization of the probe with its complementary DNA target, and (2) non-specific fluorescent dyes that intercalate with any double-stranded DNA. The commonly used reagent for method (1) is TaqMan probes and for method (2) is the SYBR Green I dye. Frequently, real-time PCR is combined with reverse transcription to quantify RNA (including messenger RNA and Non-coding RNA).

TaqMan probes are hydrolysis probes that are designed to increase the specificity of real-time PCR assays (Holland, P M; Abramson, R D; Watson, R; Gelfand, D H (1991). "Detection of specific polymerase chain reaction product by utilizing the 5'----3' exonuclease activity of *Thermus aquaticus* DNA polymerase". Proceedings of the National Academy of Sciences of the United States of America 88 (16): 7276-80. PMID 1871133; Gelfand, et al., U.S. Pat. No. 5,210,015; Mayrand; Paul E.: U.S. Pat. No. 7,413,708). TaqMan utilizes a dual-labeled probe (containing a fluorophore and matched fluorescence quencher) and fluorophore-based detection. During hybridization to the complementary target sequence, the 5'-3' nuclease activity of Taq DNA polymerase releases the fluorophore from proximity to the quencher, generating fluorescence intensity proportionate to the amount of complementary target sequence in the reaction. As in other real-time PCR methods, the resulting fluorescence signal permits quantitative measurements of the accumulation of the product during the exponential stages of the PCR; however, the TaqMan probe significantly increases the specificity of the detection.

TaqMan probes consist of a fluorophore covalently attached to the 5'-end of the oligonucleotide probe and a quencher at the 3'-end. Several different fluorophores (e.g. 6-carboxyfluorescein, acronym: FAM, or tetrachlorofluorescin, acronym: TET) and quenchers (e.g. tetramethylrhodamine, acronym: TAMRA, or dihydrocyclopyrroloindole tripeptide minor groove binder, acronym: MGB) are available. The quencher molecule quenches the fluorescence emitted by the fluorophore when excited by the cycler's light source via FRET (Fluorescence Resonance Energy Transfer). As long as the fluorophore and the quencher are in proximity, quenching inhibits any fluorescence signals.

TaqMan probes are designed such that they anneal within a DNA region amplified by a specific set of primers. As the Taq DNA polymerase extends the primer and synthesizes the nascent strand, the 5' to 3' exonuclease activity of the polymerase degrades the probe that has annealed to the template. Degradation of the probe releases the fluorophore from it and breaks the close proximity to the quencher, thus relieving the quenching effect and allowing fluorescence of the fluorophore. Hence, fluorescence detected in the real-time PCR thermal cycler is directly proportional to the fluorophore released and the amount of DNA template present in the PCR.

Another commonly used reagent for detection of products in real-time PCR is SYBR Green I (SG), an asymmetrical cyanine dye that is also used as a nucleic acid stain in molecular biology. SYBR Green I binds to double-stranded DNA. The resulting DNA-dye-complex absorbs blue light ($\lambda$max=488 nm) and emits green light ($\lambda$max=522 nm). SYBR Green I can be used for real-time PCR detection because there is a linear relation between the double-stranded DNA synthesized and the amount of green light emitted.

TaqMan requires producing double-labeled probes specific for each product, which can increase the cost of TaqMan-based real-time PCR system. However, unlike SYBR Green I, TaqMan can readily be utilized for multiplex PCR since a reaction can contain multiple TaqMan probes, each specific for a particular amplicon and each utilizing a distinguishable fluorophore.

As mentioned above, the MNAzyme system can also be utilized for product detection in real-time PCR. The inactive subunits can each contain a sensor arm complementary to a portion of the PCR product, together with a substrate-recognition arm complementary to a portion of a double-labeled probe (containing a fluorophore and matched quencher). Multiplex PCR can be achieved by utilizing multiple MNAzymes that differ in their sensor arm (conferring recognition of different PCR products) and also differ in their substrate recognition arms (conferring cleavage of different probes containing distinguishable fluorophores), such that accumulation of each PCR product leads to release of a particular fluorophore. However, MNAzymes have the potential advantage that double-labeled probes containing amplicon-specific sequences are not required; rather, because probe cleavage is mediated by the MNAzyme through its substrate recognition arm, "universal" probes can be utilized. By avoiding the need to synthesize double-labeled probes specific for each amplicon, MNAzyme has the potential to be more economical than TaqMan.

Additional background information concerning MNAzymes and other pertinent information may be found in the following documents, each of which is incorporated by reference in its entirety US 20100221711; US 20100136536; US 20100035229; US 20070231810; Nauwelaers D, Vijgen L, Atkinson C, Todd A, Geretti A M, Van Ranst M, Stuyver L. Development of a real-time multiplex RSV detection assay for difficult respiratory samples, using ultrasone waves and MNAzyme technology. J Clin Virol. 2009 November; 46(3): 238-43. Epub 2009 Sep. 15; Gerasimova Y V, Kolpashchikov D M. Nucleic acid detection using MNAzymes. Chem. Biol. 2010 Feb. 26; 17(2):104-6; Teller C, Willner I. Functional nucleic acid nanostructures and DNA machines. Curr Opin Biotechnol. 2010 Aug. 18. [Epub ahead of print]; WO/2007/041774; and Mokany E, Bone S M, Young P E, Doan T B, Todd A V. MNAzymes, a versatile new class of nucleic acid enzymes that can function as biosensors and molecular switches. J Am Chem. Soc. 2010 Jan. 27; 132(3):1051-9.

SUMMARY

This disclosure provides methods for making and using MNAzymes having improved reliability. In one aspect, the disclosure provides computational methods for designing MNAzymes, and demonstrates that MNAzymes designed using these methods have greater success rates than conventional MNAzymes. Applicants demonstrate that potential stem-loop structure within the sensor arm need not be avoided, which eases a constraint on target selection and can improve overall success rates. For example, in the context of real-time PCR, the expansion of target options eases a constraint on amplicon selection, and allows selection of more optimal PCR targets. Overall success rates are thus improved because PCR success is the pre-requirement for MNAzyme activity.

In another aspect, the present disclosure provides an improved method for selecting MNAzyme sensor junctions. Particularly, it is demonstrated that the junction sequences G|C/G or A|C improve MNAzyme activity, while among these junction sequences GG|GA is less preferred as can confer lower activity.

In another aspect, the present disclosure demonstrates that competition between one catalytic core and the other sensor leads to impaired MNAzyme activity, and methods are provided for designing MNAzymes that avoid this un-wanted competition and produce more active MNAzymes.

Applicants further demonstrate that MNAzymes designed using the foregoing methods have success rates of up to 90%, compared to success rates of 62% for MNAzymes designed using conventional methods.

These methods of designing MNAzymes may be implemented using high-throughput computational design, and optionally verified using high-throughput methods.

According to a further aspect of the present disclosure, there is provided a composition comprising at least two or more oligonucleotide components wherein at least a first oligonucleotide component and a second oligonucleotide component self-assemble in the presence of an MNAzyme assembly facilitator to form a catalytically active multi-component nucleic acid enzyme (MNAzyme), wherein each of said at least first and said second oligonucleotide components comprise a substrate arm portion, a catalytic core portion, and a sensor arm portion;

wherein upon self-assembly, the sensor arm portion of said first and second oligonucleotide components act as sensor arms of the MNAzyme, the substrate arm portion of the first and second oligonucleotide components act as substrate arms of the MNAzyme, and the catalytic core portion of the first and second oligonucleotide components act as a catalytic core of the MNAzyme;

and wherein the sensor arms of the MNAzyme interact with said MNAzyme assembly facilitator so as to maintain the first and second oligonucleotide components in proximity for association of their respective catalytic core portions to form the catalytic core of the MNAzyme, said catalytic core capable of modifying at least one substrate, and wherein said substrate arms of said MNAzyme engage a substrate so that said catalytic core of said MNAzyme can modify said substrate.

At least one of said oligonucleotide components, assembly facilitator or substrate may comprise DNA or an analogue thereof.

The assembly facilitator may be a target to be identified, detected or quantitated. The target may comprise a nucleic acid. The nucleic acid may be selected from the group comprising DNA, methylated DNA, alkylated DNA, RNA, methylated RNA, microRNA, siRNA, shRNA, tRNA, mRNA, snoRNA, stRNA, smRNA, pre- and pri-microRNA, other non-coding RNAs, ribosomal RNA, derivatives thereof, amplicons, or any combination thereof. The ribosomal RNA may be 16S ribosomal RNA.

The source of the nucleic acid may be selected from the group comprising synthetic, mammalian, human, animal, plant, fungal, bacterial, viral, archael or any combination thereof.

The nucleic acid may be amplified. The amplification may comprise one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR).

The composition may further comprise at least a third oligonucleotide component which acts to stabilize at least one of said substrate arm portions or sensor arm portions.

At least one of said assembly facilitator, said oligonucleotide components or substrate or a combination thereof may be comprised of more than one molecule.

The catalytic core portions of the first oligonucleotide component may be selected from the group comprising SEQ ID NOs 1-10, and the catalytic core portions of the second oligonucleotide component may be selected from the group comprising SEQ ID NOs 11-16.

The composition may further comprise at least one inhibitor of said self assembly of said MNAzyme.

At least one of said oligonucleotide components or assembly facilitator or substrate or a combination thereof may further comprise at least one aptamer or portion thereof. The aptamer or portion thereof may be comprised of at least one of nucleic acid, peptide, polypeptide or protein or a derivative or combination thereof.

The composition may further comprise at least one inhibitor of said self assembly of said MNAzyme.

At least one of said first or said second oligonucleotide components or said assembly facilitator or said substrate may further comprise at least one portion of self complementary sequence capable of forming a hairpin structure. The hairpin structure may inhibit self assembly of said MNAzyme. The inhibition of self assembly may be removed upon contact of an aptamer with a target. The aptamer, or portion thereof, may bind a target selected from the group comprising nucleic acids, proteins, glycoproteins, lipids, lipoproteins, cells, viruses, bacteria, archaea, fungi, antibodies, metabolites, pathogens, toxins, contaminants, poisons, small molecules, polymers, metal ions, metal salts, prions or any derivatives, portions or combinations thereof.

The substrate may comprise a nucleic acid or a protein. The nucleic acid may comprise at least one of a labeled nucleic acid, RNA, DNA, nucleic acid analogue, peptide nucleic acid, locked nucleic acid, peptide-nucleic acid chimera, or any combination thereof. The protein may comprise at least one of an antibody, polypeptide, glycoprotein, lipoprotein, or any combination thereof. The substrate may further comprise at least one nanoparticle or microparticle, or combination thereof. The substrate may be attached to an insoluble support or be free in solution. The substrate may comprise a detectable portion and a quencher portion, wherein upon modification of said substrate by said MNAzyme, a detectable effect provided by said detectable portion is increased or decreased.

The substrate arms may engage said substrate through complementary base pairing.

The modification of said substrate by said MNAzyme may provide a detectable effect. The modification of said substrate may be selected from the group comprising cleavage, ligation, porphyrin metallation, formation of carbon-carbon bonds, ester bonds or amide bonds, or any combination thereof. The detectable effect may be detected by fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof. The detectable effect may be measured, wherein the magnitude of said measurement is indicative of the quantity of a target.

At least one of said oligonucleotide components, said assembly facilitator or said substrate may be selected from the group comprising DNA, RNA, nucleic acid analogues, peptide nucleic acids, locked nucleic acids, peptide-nucleic acid chimeras, or a combination thereof. The assembly facilitator and said substrate may comprise nucleic acids that are completely or partially complementary to at least part of said first or second oligonucleotide components. At least one of said oligonucleotide components, said assembly facilitator or said substrate may comprise at least one nucleotide substitution or addition selected from the group comprising 4-acetylcytidine, 5-(carboxyhydroxylmethyl)uridine, 2'-O-methylcytidine, 5-carboxymethylaminomethyl thiouridine, dihydrouridine, 2'-O-methylpseudouridine, beta D-galactosylqueosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, beta D-mannosylmethyluridine, 5-methoxycarbonylmethyluridine, 5-methoxyuridine, 2-methylthio-N-6-isopentenyladenosine, N-((9-beta-ribofuranosyl-2-methylthiopurine-6-yl)carbamoyl)threonine, N-((9-beta-ribofuranosylpurine-6-yl)N-methyl-carbamoyl)threonine, uridine-5-oxyacetic acid methylester, uridine-5-oxyacetic acid (v), wybutoxosine, pseudouridine, queosine, 2-thiocytidine, 5-methyl-2-thiouridine, 2-thiouridine, 4-thiouridine, 5-methyluridine, N-((9-beta-D-ribofuranosylpurine-6-yl)carbamoyl)threonine, 2'-O-methyl-5-methyluridine, 2'-O-methyluridine, wybutosine, 3-(3-amino-3-carboxypropyl)uridine, beta D-arabinosyl uridine, beta D-arabinosyl thymidine.

The composition may further comprise at least a third oligonucleotide component and a fourth oligonucleotide component that self-assemble in the presence of at least one additional assembly facilitator to form at least one additional catalytically active MNAzyme, wherein each of said at least third and fourth oligonucleotide components comprise a substrate arm portion, a catalytic core portion, and a sensor arm portion;

wherein upon self-assembly of said at least a third oligonucleotide component and a fourth oligonucleotide component, the sensor arm portion of said at least third and said at least fourth oligonucleotide components form sensor arms of said at least one additional catalytically active MNAzyme, the substrate arm portion of said at least third and said at least fourth oligonucleotide components form substrate arms of said at least one additional catalytically active MNAzyme, and the catalytic core portion of said at least third and said at least fourth oligonucleotide components form a catalytic core of said at least one additional catalytically active MNAzyme;

and wherein the sensor arms of said at least one additional MNAzyme interact with said at least one additional assembly facilitator so as to maintain said at least third and said at least fourth oligonucleotide components in proximity for association of their respective catalytic core portions to form the catalytic core of said at least one additional MNAzyme, said catalytic core capable of acting on at least one additional substrate, and wherein the substrate arms of said at least one additional MNAzyme engage at least one additional substrate so that the catalytic core of said at least one additional MNAzyme can act on said at least one additional substrate.

Each of the additional substrates may be the same, different or a combination thereof.

According to another aspect of the present disclosure, there is provided a method for detecting the presence of at least one assembly facilitator comprising (a) providing two or more oligonucleotide components, wherein at least a first oligonucleotide component and a second oligonucleotide component self-assemble in the presence of an assembly facilitator to form at least one catalytically active multi-component nucleic acid enzyme (MNAzyme);

(b) contacting the two or more oligonucleotide components with a sample putatively containing the assembly facilitator under conditions permitting: (1) the self-assembly of said at least one catalytically active MNAzyme, and (2) the catalytic activity of said MNAzyme; and (c) determining the presence of the catalytic activity of said at least one MNAzyme, wherein the presence of the catalytic activity is indicative of the presence of said at least one assembly facilitator.

At least one of said oligonucleotide components or assembly facilitator may be comprised of DNA or an analogue thereof.

The assembly facilitator may be a target to be identified, detected or quantified. The target may comprise a nucleic acid. The nucleic acid may be selected from the group comprising DNA, methylated DNA, alkylated DNA, RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof. The ribosomal RNA may be 16S ribosomal RNA.

The source of the nucleic acid may be selected from the group comprising synthetic, mammalian, human, animal, plant, fungal, bacterial, viral, archael or any combination thereof.

The method may further comprise a step of amplifying the assembly facilitator. The step of amplifying may comprise one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR).

At least one of said assembly facilitator, said oligonucleotide components or substrate or a combination thereof may be comprised of more than one molecule.

The method may further comprise determination of the presence of said catalytic activity during or after said amplification.

The self assembly of the MNAzyme may require contact of the assembly facilitator with one or both of said first and second oligonucleotide components.

The method may further comprise providing at least a third oligonucleotide component that contacts at least a portion of either or both of the first and second oligonucleotide components to self-assemble the MNAzyme. The third oligonucleotide component may be comprised of more than molecule.

According to a further aspect of the present disclosure, there is provided a method for detecting the presence of at least one assembly facilitator comprising (a) providing two or more oligonucleotide components, wherein at least a first oligonucleotide component and a second oligonucleotide component self-assemble in the presence of at least a first assembly facilitator to form at least a first catalytically active multi-component nucleic acid enzyme (MNAzyme);

(b) providing at least a first substrate, said first substrate capable of being modified by said first MNAzyme, wherein said modification of said substrate by said MNAzyme provides a detectable effect;

(c) contacting said two or more oligonucleotide components with a sample putatively containing said at least first assembly facilitator under conditions permitting: (1) the self-assembly of said at least first MNAzyme, and (2) the catalytic activity of said at least first MNAzyme; and (d) detecting said detectable effect.

At least one of said oligonucleotide components, assembly facilitator or substrate may be comprised of DNA or an analogue thereof.

The assembly facilitator may be a target to be identified, detected or quantified. The target may comprise a nucleic acid. The nucleic acid may be selected from the group comprising DNA, methylated DNA, alkylated DNA, RNA, methylated RNA, microRNA, siRNA, shRNA, tRNA, mRNA, snoRNA, stRNA, smRNA, pre- and pri-microRNA, other non-coding RNAs, ribosomal RNA, derivatives thereof, amplicons, or any combination thereof. The ribosomal RNA may be 16S ribosomal RNA.

The source of the nucleic acid may be selected from the group comprising synthetic, mammalian, human, animal, plant, fungal, bacterial, viral, archael or any combination thereof.

The method may further comprise the step of amplifying the nucleic acid. The step of amplifying may comprise one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR).

At least one of said assembly facilitator, said oligonucleotide components or substrate or combination thereof may be comprised of more than one molecule.

The method may further comprise detecting said detectable effect during or after said amplification. The detectable effect may be indicative of the presence of said assembly facilitator. The detectable effect may be quantitatively or qualitatively measured.

The substrate may be a nucleic acid or a protein. The nucleic acid may comprise at least one of a labeled nucleic acid, RNA, DNA, nucleic acid analogue, peptide nucleic acid, locked nucleic acid, peptide-nucleic acid chimera, or any combination thereof. The protein comprises at least one of an antibody, polypeptide, glycoprotein, lipoprotein, or any combination thereof. The substrate may further comprise at least one of a nanoparticle or microparticle or combination thereof. The substrate may be attached to an insoluble support or be free in solution.

The substrate may comprise a nucleic acid and said substrate arms may engage said substrate through complementary base pairing.

The substrate may comprise a detectable portion and a quencher portion, wherein upon modification of the substrate by the MNAzyme, a detectable effect provided by the detectable portion is increased or decreased. The detectable effect may be detected by fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, V, visible light or infra red spectroscopy, enzymatic methods or any combination thereof.

The method may further comprise amplifying the detectable effect by use of a detectable effect amplification cascade. The detectable effect amplification cascade may comprise one or more of a ribozyme/ligase cascade, a circular nucleic acid enzyme cascade, a protein enzyme cascade, or one or more enzymes attached to a support, or any combination thereof.

The modification of said substrate may be selected from the group comprising cleavage, ligation, porphyrin metallation, formation of carbon-carbon bonds, ester bonds or amide bonds.

The method may further comprise providing at least a third and fourth oligonucleotide component, said at least third and at least fourth oligonucleotide component are capable of self assembling in the presence of at least one additional assembly facilitator to form at least one additional catalytically active MNAzyme, and wherein at least one additional substrate is present in the sample, said additional substrate is capable of being modified by the additional MNAzyme, wherein said modification provides said additional detectable effect.

The at least one additional detectable effect may be independently detectable.

At least one of each additional substrate may be attached to an insoluble support so that only one of a detectable portion and a quencher portion of the additional substrate remain attached to the support when said additional substrate is modified by said additional MNAzyme.

One additional substrate may be attached to at least one insoluble support so that a detectable effect is produced when that substrate is modified by its respective MNAzyme.

According to another aspect of the present disclosure, there is provided a method for detecting the presence of at least one target comprising (a) providing two or more oligonucleotide components wherein at least a first oligonucleotide component and at least a second oligonucleotide component are capable of self-assembly in the presence of said target to form a catalytically active multi-component nucleic acid enzyme (MNAzyme); and wherein at least one of said first and said second oligonucleotide components further comprises at least one aptamer portion;

(b) contacting said oligonucleotide components with a sample putatively containing said at least one target under conditions permitting: (1) binding of said target to said aptamer portions and (2) catalytic activity of the MNAzyme; and (c) determining the presence of the catalytic activity of the MNAzyme, wherein the presence of the catalytic activity is indicative of the presence of said target.

At least one of said oligonucleotide components may be attached to a solid support.

At least one of said oligonucleotide components may be comprised of DNA or an analogue thereof.

The target may be identified, detected or quantified.

The method may further comprise providing at least a third and fourth oligonucleotide component, said at least third and at least fourth oligonucleotide component are capable of self assembling in the presence of at least one additional target to form at least one additional catalytically active MNAzyme and wherein at least one of said third or fourth oligonucleotide components comprises at least one additional aptamer portion which binds said at least one additional target.

According to a further aspect of the present disclosure, there is provided a method for detecting the presence of at least one target comprising (a) providing two or more oligonucleotide components wherein at least a first oligonucleotide component and a second oligonucleotide component are capable of self-assembly in the presence of at least one assembly facilitator and said at least one target to form at least one catalytically active multi-component nucleic acid enzyme (MNAzyme); and wherein at least one of said first or said second oligonucleotide components or said at least one assembly facilitator further comprises at least one aptamer or portion thereof and wherein said target is capable of binding said at least one aptamer or portion thereof.

(b) providing at least one inhibitor of said self assembly of said MNAzyme (c) contacting said oligonucleotide components, assembly facilitator and said inhibitor with a sample putatively containing said at least one target under conditions permitting: (1) binding of said target to said at least one aptamer or portion thereof and (2) catalytic activity of said at least one MNAzyme; and (3) removal of said inhibition of said self assembly of said catalytically active MNAzyme; and (d) determining the presence of the catalytic activity of said MNAzyme, wherein the presence of said catalytic activity is indicative of the presence of said target.

The at least one target may be selected from the group comprising proteins, glycoproteins, lipids, lipoproteins, cells, viruses, bacteria, archaea, fungi, antibodies, metabolites, pathogens, toxins, contaminants, poisons, small molecules, polymers, metal ions, metal salts, prions, nucleic acids or any derivatives, portions or combinations thereof.

At least one of said oligonucleotide components, assembly facilitator or inhibitor may be attached to an insoluble support.

At least one of said oligonucleotide components, assembly facilitator, aptamer or aptamer portion may further comprise said inhibitor.

At least one of said first or said second oligonucleotide components or assembly facilitator may further comprise a portion of self complementary sequence capable of forming a hairpin structure. The hairpin structure may inhibit self assembly of said catalytically active MNAzyme.

The aptamer or portion thereof may be comprised of at least one of nucleic acid, peptide, polypeptide or protein or a derivative or combination thereof.

The inhibition of self assembly of said catalytically active MNAzyme may be removed upon contact of said aptamer or aptamer portion with the target.

The inhibitor may be capable of binding at least one of the group comprising said aptamer or portion thereof.

The inhibitor may be selected from the group comprising RNA, DNA, nucleic acid analogues, peptide nucleic acids, locked nucleic acids, peptide-nucleic acid chimeras, or a combination thereof.

The method may further comprise providing a substrate that can be modified by said MNAzyme to provide a detectable effect. The modification may be selected from the group comprising cleavage, ligation, porphyrin metallation, formation of carbon-carbon bonds, ester bonds or amide bonds. The substrate may be not modified by said first or second oligonucleotide components individually or by both said first and second oligonucleotide components in the absence of said assembly facilitator and said target.

The substrate may comprise a nucleic acid or a protein. The nucleic acid comprises at least one of a labeled nucleic acid, RNA, DNA, nucleic acid analogue, peptide nucleic acid, locked nucleic acid, peptide-nucleic acid chimera, or any combination thereof. The protein may comprise at least one of an antibody, polypeptide, glycoprotein, lipoprotein, or any combination thereof.

The substrate may further comprise at least one nanoparticle or microparticle or combination thereof.

Detection of the detectable effect may be indicative of said catalytic activity of said catalytically active MNAzyme and wherein said catalytic activity is indicative of said target. The detectable effect may be quantitatively or qualitatively measured. The detectable effect may be detected by fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof.

The substrate may comprise a detectable portion and a quencher portion, wherein upon modification of said substrate by said MNAzyme, a detectable effect provided by said detectable portion is increased or decreased.

According to another aspect of the present disclosure, there is provided a method for detecting the presence of at least one target comprising (a) providing two or more oligonucleotide components wherein at least a first oligonucleotide component and a second oligonucleotide component are capable of self-assembly in the presence of at least a first assembly facilitator and said at least a first target to form at least a first catalytically active multi-component nucleic acid enzyme (MNAzyme);

(b) providing at least a first substrate, said first substrate capable of being modified by said at least first MNAzyme, wherein said modification of said substrate by said MNAzyme provides a detectable effect;

(c) wherein at least one of said first or said second oligonucleotide components or said at least a first assembly facilitator or said at least a first substrate further comprises an aptamer and wherein said target is capable of binding at least a portion of said aptamer, providing at least a first inhibitor which is capable of inhibiting said self-assembly of said catalytically active MNAzyme in the absence of said target;

(d) contacting said oligonucleotide components, said assembly facilitator, said substrate, and said inhibitor with a sample putatively containing said target under conditions permitting: (1) binding of said target to said aptamer and (2) removal of said inhibition of said self assembly of said catalytically active MNAzyme (3) catalytic activity of the MNAzyme; and (e) determining the presence of said detectable effect thereby detecting the presence of said target.

At least one of said oligonucleotide components or assembly facilitator may be comprised of DNA or an analogue thereof.

The aptamer, or portion thereof, may bind a target selected from the group comprising nucleic acids, proteins, glycoproteins, lipids, lipoproteins, cells, viruses, bacteria, archaea, fungi, antibodies, metabolites, pathogens, toxins, contaminants, poisons, small molecules, polymers, metal ions, metal salts, prions or any derivatives, portions or combinations thereof.

At least one of said oligonucleotide components, assembly facilitator, substrate, or inhibitor may be attached to an insoluble support.

At least one of said oligonucleotide components, assembly facilitator, aptamer or aptamer portion may further comprise said inhibitor.

The aptamer or portion thereof may be comprised of at least one of nucleic acid, peptide, polypeptide or protein or a derivative or combination thereof.

At least one of said first or said second oligonucleotide components, assembly facilitator or substrate may further comprise a portion of self complementary sequence capable of forming a hairpin structure. The hairpin structure may inhibit self assembly of said catalytically active MNAzyme. The inhibition of self assembly of said catalytically active MNAzyme may be removed upon contact of said aptamer or aptamer portion with the target.

The inhibitor may be capable of binding at least one of the group comprising said aptamer or portion thereof. The inhibitor may be selected from the group comprising RNA, DNA, nucleic acid analogues, peptide nucleic acids, locked nucleic acids, peptide-nucleic acid chimeras, or a combination thereof.

The substrate may comprise a nucleic acid or a protein. The nucleic acid may comprise at least one of a labeled nucleic acid, RNA, DNA, nucleic acid analogue, peptide nucleic acid, locked nucleic acid, peptide-nucleic acid chimera, or any combination thereof. The protein may comprise at least one of an antibody, polypeptide, glycoprotein, lipoprotein, or any combination thereof.

The substrate may further comprise at least one nanoparticle or microparticle or combination thereof.

Detection of said detectable effect may detect the presence of said target. The detectable effect may be quantitatively or qualitatively measured. The detectable effect may be detected by fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof.

The substrate may comprise a detectable portion and a quencher portion, wherein upon modification of said substrate by said MNAzyme, a detectable effect provided by said detectable portion is increased or decreased. The modification may be selected from the group comprising cleavage, ligation, porphyrin metallation, formation of carbon-carbon bonds, ester bonds or amide bonds.

The method may further comprise providing at least a third and fourth oligonucleotide component, wherein said at least third and at least fourth oligonucleotide component are capable of self assembling in the presence of at least one additional assembly facilitator and at least one additional target to form at least one additional catalytically active MNAzyme, and wherein at least one additional substrate is present in the sample, said additional substrate is capable of being modified by the additional MNAzyme, wherein said modification provides an additional detectable effect;

and wherein at least one of said third or fourth oligonucleotide component or said additional assembly facilitator or said additional substrate further comprises at least one additional aptamer which binds said at least one additional target;

wherein at least one additional inhibitor molecule contacts a portion of said additional aptamer, thereby inhibiting said self-assembly of said catalytically active additional MNAzyme in the absence of said additional target; and wherein said at least one additional assembly facilitator contacts at least a portion of said additional oligonucleotide components.

The at least one additional detectable effect may be independently detectable.

Each of the additional substrates may be the same, different or a combination thereof.

At least one of each additional substrate may be attached to an insoluble support so that only one of a detectable portion and a quencher portion of the additional substrate remain attached to the support when said additional substrate is modified by said additional MNAzyme.

According to a further aspect of the present disclosure, there is provided a method for detecting the presence of at least one nucleic acid sequence variant comprising (a) providing two or more oligonucleotide components, wherein at least a first oligonucleotide component and a second oligonucleotide component self-assemble in the presence of a sequence variant of a nucleic acid to form a catalytically active multi-component nucleic acid enzyme (MNAzyme);

(b) providing at least one substrate, said substrate capable of being modified by said first MNAzyme, wherein said modification of said substrate by said MNAzyme provides a detectable effect;

(c) contacting the two or more oligonucleotide components with a sample putatively containing said sequence variant under conditions permitting: (1) the self-assembly of said catalytically active MNAzyme, and (2) the catalytic activity of said MNAzyme; and (d) determining the presence of said detectable effect thereby detecting the presence of said at least one sequence variant.

The sequence variant may be selected from the group comprising single nucleotide polymorphisms, multiple nucleotide polymorphisms, insertions, deletions, duplications, translocations, frameshift sequence variants, nonsense sequence variants, or any combination thereof. The sequence variant may be present in DNA or RNA.

Either or both of said first oligonucleotide component and said second oligonucleotide components may be comprised of more than one molecule.

The sample containing said sequence variant may be selected from the group comprising bisulfite modified methylated or non-methylated DNA, bisulfite modified methylated or non-methylated RNA, at least one amplicon of bisulfite modified methylated or non-methylated DNA, at least one amplicon of bisulfite modified methylated or non-methylated RNA or a combination thereof.

The self assembly of the multi-component nucleic acid enzyme may require contact of at least a portion of either or both of the first and second oligonucleotide components with the nucleic acid which comprises said sequence variant.

The method may further comprise a step of amplifying the nucleic acid containing said sequence variant. The step of amplifying may comprise one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR).

The method may further comprise determination of the presence of said nucleic acid sequence variant during or after said amplification.

The detectable effect may be detected by fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof.

The substrate may comprise a detectable portion and a quencher portion, wherein upon modification of said substrate by said MNAzyme, a detectable effect provided by said detectable portion is increased or decreased.

The substrate may be attached to an insoluble support or free in solution.

The modification may be selected from the group comprising cleavage, ligation, porphyrin metallation, formation of carbon-carbon bonds, ester bonds or amide bonds.

The method may further comprise (a) providing at least a third oligonucleotide component and at least a fourth oligonucleotide component that self assemble in the presence of at least one additional nucleic acid sequence variant to form at least one additional catalytically active multi-component nucleic acid enzyme (MNAzyme);

(b) contacting said at least third and at least fourth oligonucleotide components with a sample putatively containing at least one additional nucleic acid sequence variant in the presence of at least one additional substrate capable of being modified by said at least one additional MNAzyme, wherein said modification of said at least one additional substrate provides at least one additional detectable effect under conditions permitting: (1) the self-assembly of at least one MNAzyme, and (2) the catalytic activity of at least one MNAzyme; and (c) detecting said at least one additional detectable effect, thereby detecting the presence of said at least one additional sequence variant.

The at least one additional detectable effect may be independently detectable.

Each of the additional substrates may be the same, different or a combination thereof.

The method may further comprise providing an insoluble support having said substrate attached thereto.

At least one of each additional substrate may be attached to an insoluble support so that only one of a detectable portion and a quencher portion of the additional substrate remain attached to the support when said additional substrate is modified by said additional MNAzyme.

According to another aspect of the present disclosure, there is provided a method for detecting the presence of a sequence variant of a nucleic acid comprising (a) providing two or more oligonucleotide components comprising at least a first oligonucleotide component and a second oligonucleotide component capable of self assembly in the presence of a nucleic acid to form at least a first catalytically active multi-component nucleic acid enzyme (MNAzyme);

(b) contacting the two or more oligonucleotide components with a sample putatively containing the nucleic acid, in the presence of at least a first substrate modifiable by said at least a first MNAzyme, wherein the substrate comprises a detectable portion capable of providing at least a first detectable effect upon modification of the substrate by said at least a first MNAzyme under conditions permitting: (1) the self-assembly of the MNAzyme, and (2) the catalytic activity of the MNAzyme; and (c) wherein the absence of the catalytic activity is indicative of the presence of a sequence variant in said nucleic acid.

According to a further aspect of the present disclosure, there is provided a method for detecting the presence of at least one methylated nucleic acid comprising (a) providing two or more oligonucleotide components, wherein at least a first oligonucleotide component and a second oligonucleotide component self-assemble in the presence of methylated nucleic acid to form at least one catalytically active multi-component nucleic acid enzyme (MNAzyme);

(b) providing at least a first substrate, said first substrate capable of being modified by said first MNAzyme, wherein said modification of said substrate by said MNAzyme provides at least a first detectable effect;

(c) contacting the two or more oligonucleotide components with a sample putatively containing the methylated nucleic acid under conditions permitting: (1) the self-assembly of the catalytically active MNAzyme, and (2) the catalytic activity of the MNAzyme; and (d) determining the presence of said at least one detectable effect thereby detecting the presence of said at least one methylated nucleic acid.

The conditions may further comprise a temperature that facilitates hybridization of said MNAzyme with said methylated nucleic acid but not with unmethylated nucleic acid.

The method may further comprise amplifying the detectable effect by use of a detectable effect amplification cascade. The detectable effect amplification cascade may comprise one or more of a ribozyme/ligase cascade, a circular nucleic acid enzyme cascade, a protein enzyme cascade, or one or more enzymes attached to a support. or any combination thereof.

The source of said methylated nucleic acid may be selected from the group comprising synthetic, mammalian, human, animal acid, plant, fungal, bacterial, viral, archael or any combination thereof.

The methylated nucleic acid may be selected from the group comprising methylated RNA or methylated DNA.

The self assembly of the multi-component nucleic acid enzyme may require contact of the methylated nucleic acid with one or both of the first and second oligonucleotide components.

The method may further comprise providing an insoluble support having at least one of said substrate or said first or second oligonucleotide components, or a combination thereof attached thereto.

The detectable effect may be detected by fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof.

The substrate may comprise a detectable portion and a quencher portion, wherein upon modification of said substrate by said MNAzyme, a detectable effect provided by said detectable portion is increased or decreased.

The modification may be selected from the group comprising cleavage, ligation, porphyrin metallation, formation of carbon-carbon bonds, ester bonds or amide bonds.

The method may further comprise providing at least a third and fourth oligonucleotide component, wherein said at least third and at least fourth oligonucleotide component are capable of self assembling in the presence of at least one additional methylated nucleic acid to form at least one additional catalytically active MNAzyme, and wherein at least one additional substrate is present in the sample, said additional substrate is capable of being modified by said additional MNAzyme, wherein said modification provides said additional detectable effect.

The at least one additional detectable effect may be independently detectable.

Each of the additional substrates may be the same, different or a combination thereof.

At least one of said additional substrate may be attached to an insoluble support so that only one of an additional detectable portion and an additional quencher portion of the additional substrate remain attached to the support when said additional substrate is modified by said additional MNAzyme.

According to another aspect of the present disclosure, there is provided a method for detecting at least one assembly facilitator using an amplification cascade comprising (a) providing two or more oligonucleotide components comprising at least a first oligonucleotide component and at least a second oligonucleotide component that self assemble in the presence of at least a first assembly facilitator to form at least a first catalytically active multi-component nucleic acid enzyme (MNAzyme);

(b) providing an insoluble support having at least a first substrate attached thereto, said first substrate is capable of being modified by said MNAzyme, wherein said first substrate comprises at least a third molecule comprising at least a first catalytically active enzyme that is released upon modification of said first substrate by said first MNAzyme;

(c) contacting said two or more oligonucleotide components with a sample putatively containing said assembly facilitator, in the presence of said insoluble support having said first substrate attached thereto under conditions permitting: (1) the self-assembly of said MNAzyme, and (2) the catalytic activity of said MNAzyme; and (d) providing an insoluble support having at least a second substrate attached thereto, said second substrate cleavable by said first catalytically active enzyme wherein said second substrate comprises at least a fourth molecule comprising at least a detectable moiety which is released upon modification of said second substrate by said first enzyme; and (e) wherein said first catalytically active enzyme modifies a plurality of said second substrate thereby releasing a plurality of detectable moieties (f) wherein said detectable moieties are detectable after modification of said second substrate by said first catalytically active enzyme, and;

(g) wherein detection of said detectable moieties is indicative of the presence of said assembly facilitator.

The detectable moieties may further comprise an additional second catalytically active enzyme capable of modifying said first substrate thereby releasing additional catalytically active enzyme. At least one of said first or said second catalytically active enzyme may be selected from the group comprising MNAzymes, DNAzymes, ribozymes, hydrolytic enzymes, restriction endonucleases, exonucleases, proteases, proteinases, hydrolases, lyticases, peptidases, dipeptidases, esterases, caspases, cathepsins, desulfhydrases, amidases, glycosidases.

The assembly facilitator may comprise a target to be identified, detected or quantified. The target may be selected from the group comprising nucleic acids, proteins, glycoproteins, lipids, lipoproteins, cells, viruses, bacteria, archaea, fungi, antibodies, metabolites, pathogens, toxins, contaminants, poisons, small molecules, polymers, metal ions, metal salts, prions, nucleic acids or any derivatives, portions or combinations thereof. The nucleic acid may be selected from the group comprising DNA, methylated DNA, alkylated DNA, RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof.

According to a further aspect of the present disclosure, there is provided a method for detecting a target using an MNAzyme mediated signal amplification cascade comprising (a) providing a first oligonucleotide component and a second oligonucleotide component that self assemble in the presence of said target to form a first catalytically active multi-component nucleic acid enzyme (MNAzyme);

(b) providing an insoluble support having a first and a second substrate attached thereto, said first and second substrates are capable of being modified by said first MNAzyme, wherein said first and second substrates comprise at least a third and a fourth oligonucleotide component respectively, capable of forming a second catalytically active MNAzyme, wherein said third and fourth oligonucleotide components are released upon modification of said first and second substrates by said first MNAzyme;

(c) providing said insoluble support having a third and a fourth substrate attached thereto, said third and fourth substrates are capable of being modified by said second MNAzyme, wherein said third and fourth substrates comprise at least a fifth and a sixth oligonucleotide component respectively, capable of forming a third catalytically active MNAzyme, wherein said fifth and said sixth oligonucleotide components are released upon modification of said third and fourth substrates by said second MNAzyme, and;

(d) providing an assembly facilitator capable of facilitating the assembly of said second and said third MNAzyme, and;

(e) providing a fifth substrate which is capable of being modified by said second MNAzyme to provide a detectable effect;

(f) contacting said first and second oligonucleotide components with a sample putatively containing said target, in the presence of said assembly facilitator, and in the presence of said insoluble support having said first, second, third and fourth substrates attached thereto under conditions permitting: (1) self-assembly of said first, second and third, MNAzymes, and (2) catalytic activity of said first, second and third, MNAzymes; and (g) wherein said third MNAzyme modifies said first and second substrates thereby further providing said second MNAzyme wherein said second MNAzyme further modifies at least one of said third, fourth and fifth substrates thereby further providing said third MNAzyme thereby further providing said detectable effect, and;

(h) wherein detection of said detectable effect is indicative of the presence of said target.

The target may be identified, detected or quantified. The target may be selected from the group comprising nucleic acids, proteins, glycoproteins, lipids, lipoproteins, cells, viruses, bacteria, archaea, fungi, antibodies, metabolites, pathogens, toxins, contaminants, poisons, small molecules, polymers, metal ions, metal salts, prions, nucleic acids or any derivatives, portions or combinations thereof. The nucleic acid may be selected from the group comprising DNA, methylated DNA, alkylated DNA, RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof.

The fifth substrate may be the same as or different to any one of said first, second, third or fourth substrates.

Each of said first, second, third or fourth substrates may be present on the same solid support or different solid supports or any combination thereof.

The modification of at least one of said first, second, third or fourth substrates may further provide a detectable effect.

According to another aspect of the present disclosure, there is provided a method for making a plurality of multi-component nucleic acid enzymes (MNAzymes) that each recognize at least one assembly facilitator and modify a substrate, the method comprising:

(a) providing a plurality of assembly facilitators to be identified, detected or quantified, (b) designing two or more oligonucleotide components wherein at least a first oligonucleotide component and a second oligonucleotide component self-assemble in the presence of an assembly facilitator to form a catalytically active multi-component nucleic acid enzyme (MNAzyme), wherein each of the at least first and second oligonucleotide components comprise a substrate arm portion, a catalytic core portion, and a sensor arm portion, wherein upon self-assembly, the sensor arm portion of the first and second oligonucleotide components form sensor arms of the MNAzyme, the substrate arm portion of the first and second oligonucleotide components form substrate arms of the MNAzyme, and the catalytic core portion of the first and second oligonucleotide components form a catalytic core of the MNAzyme;

and wherein the sensor arms of the MNAzyme interact with an assembly facilitator so as to maintain the first and second oligonucleotide components in proximity for association of their respective catalytic core portions to form the catalytic core of the MNAzyme, said catalytic core capable of acting on at least one substrate, and wherein the substrate arms of the MNAzyme engage a substrate so that the catalytic core of the MNAzyme can modify said substrate;

(c) altering said two or more oligonucleotide components such that the substrate arm portion and the catalytic core portion of the first and second oligonucleotide components is constant, and the sensor arm portion of at least one of the first and second oligonucleotide components is adapted to recognize another of the plurality of assembly facilitators, and (d) repeating the altering step for each of the plurality of assembly facilitators.

According to a further aspect of the present disclosure, there is provided a kit for detecting the presence of a plurality of targets comprising a plurality of oligonucleotide components designed to assemble a plurality of MNAzymes each corresponding to at least one of a plurality of targets, and at least one substrate.

According to another aspect of the present disclosure, there is provided a kit for assembling a plurality of MNAzymes comprising a plurality of assembly facilitators, a plurality of oligonucleotide components designed to assemble a plurality of MNAzymes each one corresponding to each of the plurality of assembly facilitators, and at least one substrate.

According to a further aspect of the present disclosure, there is provided a kit for detecting a target comprising a plurality of oligonucleotide components designed to assemble an MNAzyme corresponding to the target, and a substrate.

The terms "polynucleotide", "nucleic acid" and "oligonucleotide" may be used interchangeably and refer to a single- or double-stranded polymer of deoxyribonucleotide or ribonucleotide bases, or analogues, derivatives, variants, fragments or combinations thereof, including but not limited to DNA, methylated DNA, alkylated DNA, RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof. By way of non-limiting example, the source of a nucleic acid may be selected from the group comprising synthetic, mammalian, human, animal, plant, fungal, bacterial, viral, archael or any combination thereof.

The terms "oligonucleotide" and "primer" typically denote a segment of DNA or a DNA-containing nucleic acid molecule, or RNA or RNA-containing molecule, or a combination thereof. Examples of oligonucleotides include nucleic acid targets; substrates, for example, those which can be modified by an MNAzyme; primers such as those used for in vitro target amplification by methods such as PCR; and components of MNAzymes. MNAzyme assembly facilitators, in certain embodiments, may comprise oligonucleotides as defined herein. Partzymes as used herein may also comprise oligonucleotides.

The terms "polynucleotide", "nucleic acid" and "oligonucleotide" include reference to any specified sequence as well as to the sequence complementary thereto, unless otherwise indicated. Oligonucleotides may comprise at least one addition or substitution, including but not limited to the group comprising 4-acetylcytidine, 5-(carboxyhydroxylmethyl) uridine, 2'-O-methylcytidine, 5-carboxymethylaminomethyl thiouridine, dihydrouridine, 2'-O-methylpseudouridine, beta D-galactosylqueosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, beta D-mannosylmethyluridine, 5-methoxycarbonylmethyluridine, 5-methoxyuridine, 2-methylthio-N6-isopentenyladenosine, N-((9-beta-ribofuranosyl-2-methylthiopurine-6-yl)carbamoyl)threonine, N-((9-beta-ribofuranosylpurine-6-yl)N-methyl-carbamoyl) threonine, uridine-5-oxyacetic acid methylester, uridine-5-oxyacetic acid (v), wybutoxosine, pseudouridine, queosine, 2-thiocytidine, 5-methyl-2-thiouridine, 2-thiouridine, 4-thiouridine, 5-methyluridine, N-((9-beta-D-ribofuranosylpurine-6-yl)carbamoyl)threonine, 2'-O-methyl-5-methyluridine, 2'-O-methyluridine, wybutosine, 3-(3-amino-3-carboxypropyl)uridine, beta D-arabinosyl uridine, beta D-arabinosyl thymidine.

The terms "catalytic nucleic acid molecule", "catalytic nucleic acid", "nucleic acid enzyme" and "catalytic nucleic acid sequence" are used herein interchangeably and shall mean a DNA molecule or DNA-containing molecule (also known in the art as a "DNA enzyme", "deoxyribozyme" or "DNAzyme") or an RNA or RNA-containing molecule (also known in the art as a "RNA enzyme" or "ribozyme") or a combination thereof, being a DNA-RNA hybrid molecule, which may recognize a substrate and catalyze a modification of the substrate. The nucleotide residues in the catalytic nucleic acids may include the bases A, C, G, T, and U, as well as derivatives and analogues thereof.

The term "derivative" when used in relation to a nucleic acid or nucleotide of the present disclosure includes any functionally-equivalent nucleic acids or nucleotides, including any fusion molecules produced integrally (e.g., by recombinant means) or added post-synthesis (e.g., by chemical means). Such fusions may comprise oligonucleotides of the disclosure with RNA or DNA added thereto or conjugated to a polypeptide (e.g., puromycin or other polypeptide), a small molecule (e.g., psoralen) or an antibody.

The term "analogue" when used in relation to a nucleic acid or nucleotide includes a compound having a physical structure that is related to a DNA or RNA molecule or residue, and may be capable of forming a hydrogen bond with a DNA or RNA residue or an analogue thereof (i.e., it is able to anneal with a DNA or RNA residue or an analogue thereof to form a base-pair), but such bonding is not so required for said compound to be encompassed within the term "analogue". Such analogues may possess different chemical and biological properties to the ribonucleotide or deoxyribonucleotide residue to which they are structurally related. Methylated, iodinated, brominated or biotinylated residues are examples of analogues. Active DNAzymes have been described which contain nucleotide analogues, including deoxyinosine, C-5-immidazole deoxyuridine, 3-(aminopropynyl)-7-deaza-dATP, 2'-O-methyl RNA, 2' O-methyl cap (Warashina et al., 1999; Cairns et al., 2003; Schubert et al., 2004; Sidorov et al., 2004). Other analogues are compatible with catalytic activity of DNAzymes. Alteration of a catalytic nucleic acid sequence, for example by substitution of one base for another, by substitution of an analogue for a base, or alteration of the sugar component or phosphodiester backbone, can be straight forward for the skilled artisan. For example, alterations can be made during synthesis, or by modification of specific bases after synthesis. Empirical testing of catalytic nucleic acids incorporating alterations such as base changes or base analogues allows for assessment of the impact of the altered sequences, or specific analogues, on catalytic activity. Analogues of the bases A, C, G, T and U are known in the art, and a subset is listed in Table 2.

TABLE 2

Examples of nucleotide analogues useful herein

| Abbreviation | Name |
| --- | --- |
| ac4c | 4-acetylcytidine |
| chm5u | 5-(carboxyhydroxylmethyl)uridine |
| Cm | 2'-O-methylcytidine |
| Cmnm5s2u | 5-carboxymethylaminomethyl thiouridine |
| D | Dihydrouridine |
| Fm | 2'-O-methylpseudouridine |
| Galq | beta, D-galactosylqueosine |
| Gm | 2'-O-methylguanosine |
| 1 | Inosine |
| i6a | N6-isopentyladenosine |
| m1a | 1-methyladenosine |
| m1f | 1-methylpseudouridine |
| m1g | 1-methylguanosine |
| Ml1 | 1-methylinosine |
| m22g | 2,2-dimethylguanosine |
| m2a | 2-methyladenosine |
| m2g | 2-methylguanosine |
| m3c | 3-methylcytidine |
| m5c | 5-methylcytidine |
| m6a | N6-methyladenosine |
| m7g | 7-methylguanosine |
| mam5u | 5-methylaminomethyluridine |
| mam5s2u | 5-methoxyaminomethyl-2-thiouridine |
| Manq | beta, D-mannosylmethyluridine |
| mcm5s2u | 5-methoxycarbonylmethyluridine |
| Mo5u | 5-methoxyuridine |
| Ms2i6a | 2-methylthio-N6-isopentyladenosine |
| Ms2t6a | N-((9-beta-ribofuranosyl-2-methylthiopurine-6-yl)carbamoyl)threonine |
| Mt6a | N-((9-beta-ribofuranosylpurine-6-yl)N-methyl-carbamoyl)threonine |
| Mv | Uridine-5-oxyacetic acid methylester |
| o5u | Uridine-5-oxyacetic acid (v) |
| Osyw | Wybutoxosine |
| P | Pseudouridine |

TABLE 2-continued

Examples of nucleotide analogues useful herein

| Abbreviation | Name |
| --- | --- |
| Q | Queosine |
| s2c | 2-thiocytidine |
| s2t | 5-methyl-2-thiouridine |
| s2u | 2-thiouridine |
| s4u | 4-thiouridine |
| T | 5-methyluridine |
| t6a | N-((9-beta-D-ribofuranosylpurine-6-yl)carbamoyl)threonine |
| Tm | 2'-O-methyl-5-methyluridine |
| Um | 2'-O-methyluridine |
| Yw | Wybutosine |
| X | 3-(3-amino-3-carboxypropyl)uridine, (acp3)u |
| AraU | beta D-arabinosyluridine |
| AraT | beta D-arabinosylthymidine |

The term "fragment" when used in relation to a nucleic acid refers to a constituent of that nucleic acid. Typically the fragment possesses qualitative biological activity in common with the nucleic acid, although this does not necessarily have to be the case. Fragments of a nucleic acid do not necessarily need to encode polypeptides which retain biological activity. Rather, a nucleic acid fragment may, for example, be useful as a hybridization probe or PCR oligonucleotide. The fragment may be derived from a nucleic acid of the disclosure or alternatively may be synthesized by some other means, for example chemical synthesis.

The term "variant" as used herein refers to substantially similar nucleic acid or polypeptide sequences. Generally, sequence variants possess qualitative biological activity in common. Further, such sequence variants may share at least 50%, 55%, 60%, 65%, 70%, 75%, 80%, 85%, 90%, 95%, 96%, 97%, 98% or 99% sequence identity. Also included within the meaning of the term "variant" are homologues, which are typically a polypeptide or nucleic acid from a different species but sharing substantially the same biological function or activity as the corresponding polypeptide or nucleic acid disclosed herein.

The term "high stringency" as used herein refers to the conditions under which two nucleic acids may be hybridized, and may include, for example, the concentration of salts and/or detergents in a solution, the temperature of a solution that is used during the hybridization of the two nucleic acids and time period of the hybridization. Accordingly, the term "high stringency" as used herein refers to conditions in a solution that are conducive to hybridization of two nucleic acids only where such nucleic acids share a high degree of complementarity. The degree of complementarity may include, but not be limited to, a range of from about 50% to 99%. Thus, "high stringency" conditions may involve, but are not limited to, the use of a varying temperature and a buffer comprising various concentrations of detergents, salts, and divalent cations.

The terms "assembly facilitator molecule", "assembly facilitator", "MNAzyme assembly facilitator molecule", "facilitator" and "MNAzyme assembly facilitator" as used herein refer to entities that can facilitate the self-assembly of component partzymes to form a catalytically active MNAzyme. In preferred embodiments an assembly facilitator is required for the self assembly of an MNAzyme. An assembly facilitator in some embodiments comprises a target such as a nucleic acid or non-nucleic acid analyte. Assembly facilitator molecules may comprise one or more regions or molecules that may pair with, or bind to, one or more oligonucleotide "partzymes," which constitute components or portions of an "MNAzyme". It is not required that the assembly facilitator interact with, pair with, or bind to each component partzyme or oligonucleotide provided that it interacts with, pairs with, or binds to, at least one of the component partzymes of an MNAzyme. As used herein, MNAzyme assembly facilitator molecules are intended to encompass the broadest range of constituents which can facilitate self-assembly of an MNAzyme. In some embodiments, an assembly facilitator may comprise a nucleic acid. In other embodiments, an assembly facilitator may comprise any cell or any portion thereof, for example, any eukaryotic or prokaryotic cell, a virus, prion, yeast or fungus, or any other molecule, for example, including but not limited to a protein, polypeptide, peptide or nucleic acid. In other embodiments, an assembly facilitator may comprise a virus, prion, yeast or fungus, or any other molecule, for example, including but not limited to glycoproteins, lipids, lipoproteins, entire organisms, cells, viruses, bacteria, archaea, fungi, antibodies, metabolites, pathogens, toxins, contaminants, poisons, small molecules, polymers, metal ions, metal salts, prions or any derivatives, portions or combinations thereof.

The term "target" as used herein includes any natural or synthetic entity, constituent or analyte which is sought to be detected, identified or quantified by a particular MNAzyme(s). Targets therefore encompass the broadest range of detectable entities, constituents or analytes for which methods of sensitive detection, identification and/or quantification are desirable. In some embodiments, a target comprises an assembly facilitator. Some exemplary targets include, but are not limited to, protein, polypeptide, peptide or nucleic acid, glycoproteins, lipids, lipoproteins, entire organisms, cells, viruses, bacteria, archaea, yeast, fungi, antibodies, metabolites, pathogens, toxins, contaminants, poisons, small molecules, polymers, metal ions, metal salts, prions or any derivatives, portions or combinations thereof. Other targets are also contemplated for use herein.

The terms "substrate", "substrate molecule" and "chemical substrate" as used herein include any molecule which is capable of being recognized, and acted upon or chemically modified by a catalytic molecule. In particular embodiments, a substrate may be recognized and modified by an enzyme. In other embodiments, a substrate may be recognized and modified by a catalytic nucleic acid molecule. The chemical modification of a substrate can be measured by the appearance of, or increase in, a product of the modification reaction, or by the disappearance of, or decrease in, a substrate of the modification reaction(s). A particular catalytic molecule may recognize one or more different substrate molecules provided each substrate molecule has at least a minimum structure which is recognizable for catalytic activity by the catalytic molecule.

A "reporter substrate", "reporter probe" or "reporter probe substrate" as used herein is a substrate that is particularly adapted to facilitate measurement of either the disappearance of a substrate or the appearance of a product in connection with a catalyzed reaction. Reporter substrates can be free in solution or bound (or "tethered"), for example, to a surface, or to another molecule. A reporter substrate can be labeled by any of a large variety of means including, for example, fluorophores (with or without one or more additional components, such as quenchers), radioactive labels, labeling with biotin (e.g. biotinylation) or chemiluminescent labels. Reporter substrates for catalytic nucleic acids may also include protein or nucleic acid enzymes, for example, covalently attached to their termini.

As used herein, "generic" or "universal" substrates are substrates, for example reporter substrates, that are recognized by and acted on catalytically by a plurality of MNAzymes, each of which can recognize a different target. The use of such substrates facilitates development of separate assays for detection, identification or quantification of a wide variety of targets using structurally-related MNAzymes all of which recognize a universal substrate. These universal substrates can each be independently labeled with one or more labels. In preferred embodiments, independently detectable labels are used to label one or more generic substrates to allow the creation of a convenient system for independently or simultaneously detecting a variety of targets using MNAzymes.

As used herein, the terms "partzyme", "component partzyme" and "component oligonucleotide" refer to a DNA-containing or RNA-containing or DNA-RNA-containing oligonucleotide, two or more of which, only in the presence of a MNAzyme assembly facilitator molecule, can together form an "MNAzyme." In certain preferred embodiments, one or more component partzymes, and preferably at least two, may comprise three regions or domains: a "catalytic" domain, which forms part of the MNAzyme's catalytic core that catalyzes a chemical modification; a "sensor arm" domain, which may associate with and/or bind to an assembly facilitator (e.g. a target); and a "substrate arm" domain, which may associate with and/or bind to a substrate. A partzyme may comprise one or more molecules. Partzymes may comprise at least one additional component including but not limited to an aptamer, referred to herein as an "apta-partzyme." A partzyme may also include a substrate.

The term "MNAzyme" as used herein, refers to two or more oligonucleotide sequences (e.g. partzymes) which, only in the presence of MNAzyme assembly facilitator molecule (for example, a target), form an active nucleic acid enzyme that is capable of catalytically modifying a substrate. An exemplary MNAzyme may comprise partzyme A and partzyme B. DNA partzymes A and B may each bind to a target (e.g., through Watson-Crick base pairing with a nucleic acid target). The MNAzyme only forms when the sensor arms of partzymes A and B hybridize adjacent to each other on the target. The substrate arms of the MNAzyme engage the reporter substrate, the cleavage of which is catalyzed by the catalytic core of the MNAzyme, formed by the interaction of the catalytic domains of partzymes A and B. The MNAzyme cleaves the substrate between a fluorophore and a quencher dye pair, thus generating signal. Cleavage of a DNA/RNA chimera (reporter substrate) is exemplified in the drawing. The terms "multi-component nucleic acid enzyme" and "MNAzyme" are used herein interchangeably and comprise bipartite structures, composed of two molecules, or tripartite structures, composed of three nucleic acid molecules, or other multipartite structures, for example those formed by four or more nucleic acid molecules. An MNAzyme may also comprise a stabilizing oligonucleotide which provides stability of the MNAzyme by interacting with an assembly facilitator or substrate. It is apparent that formation of an MNAzyme requires the assembly of at least the partzyme components with the assembly facilitator, as well as the binding of a substrate, for catalytic activity to be detectable, and that the absence of any of these components will result in a lack of catalytic activity.

As used herein an "aptamer" may comprise a structure that has the ability to recognize one or more ligands. For example, the recognition may have a high degree of specificity due to higher level structure of the aptamer, such as, a 3-dimensional binding domain or pocket. Aptamers may therefore bind protein, polypeptide, peptide or nucleic acid, glycoproteins, lipids, lipoproteins, cells, viruses, bacteria, archaea, fungi, antibodies, metabolites, pathogens, toxins, contaminants, poisons, entire organisms, small molecules, polymers, metal ions, metal salts, prions or any derivative, portion or combination thereof, or any other entity. Preferred aptamers herein may comprise short single-stranded DNA or RNA oligomers that can be isolated from complex libraries of synthetic nucleic acid by an iterative process of adsorption, recovery, and reamplification. Aptamers may therefore be generated against almost any target, ranging from small molecules such as amino acids, or antibiotics to protein and nucleic acid structures.

As used herein, the term "cascade" refers to any succession of processes or operations that occur in successive stages, wherein the occurrence of each stage is typically dependent on the occurrence of a preceding stage. A cascade may therefore include, but is not limited to, an enzymatic cascade or any other signal transduction cascade. In some embodiments, a cascade may comprise amplification of a signal resulting from catalytic activity of an MNAzyme. In preferred embodiments, such an amplification cascade may involve repeated and therefore cyclic amplification of a signal, wherein catalytic activity of a first MNAzyme makes available a required molecule for catalytic activity of a second MNAzyme, which in turn makes available a required molecule for catalytic activity of the first MNAzyme. In some embodiments, the required molecule may comprise a partzyme, an enzyme, an assembly facilitator, a substrate, a target, a portion or fragment thereof or a combination thereof. In some embodiments, a cascade may therefore involve production of a cumulative effect, and thus detect a target of low abundance by generating a signal to a level at which it may be detected. In other embodiments, more than two catalytic stages may be employed. The cascade may be linear. In a preferred embodiment, the cascade may be exponential.

As used herein, the terms "inhibitor" or "assembly inhibitor" include, but are not limited to, any protein, polypeptide, peptide or nucleic acid, RNA, DNA, nucleic acid analogues, peptide nucleic acids, locked nucleic acids, peptide-nucleic acid chimeras, glycoproteins, lipids, lipoproteins, cells, viruses, bacteria, archaea, fungi, antibodies, metabolites, pathogens, toxins, contaminants, poisons, entire organisms, small molecules, polymers, metal ions, metal salts, prions or any derivative, portion or combination thereof, or any other entity or molecule that interacts with one or more components of an MNAzyme as defined herein, or that interacts with a substrate or assembly facilitator, so as to prevent assembly of an MNAzyme. An "inhibitor" or "assembly inhibitor" need not be in physical proximity to an MNAzyme, but, by way of non-limiting example, may competitively bind a component part of an MNAzyme, substrate or assembly facilitator, thereby preventing such component part from being available for MNAzyme assembly. Such binding may include, for example, an inhibitory nucleic acid that is complementary to an oligonucleotide comprising a component part of an MNAzyme.

BRIEF DESCRIPTION OF THE DRAWINGS

FIG. 1. Summary of the large-scale MNAzyme design and experimental verification results. Total design: total number of genes that have been designed for MNAzyme detection of real-time PCR amplification. The genes used in gene list 1 (GL1), gene list 2 (GL2), gene list 3.2 (GL3), gene list 4 (GL4), gene list 5 (GL5) are listed in FIG. 11. Success design: number of genes whose amplification was successfully detected. PCR failure: number of genes for which PCR amplification did not produce the expected amplicon. Non-PCR failure: number of genes for which PCR amplification produced the expected amplicon but detection of the PCR product by the MNAzyme reaction failed. Success rate: overall success rate, i.e., ratio of "Success Design" to "Total Design".

FIG. 5 and FIG. 6: Partzyme end point (nucleic acid at the junction) and the MNAzyme activity in two independent experimental assays. These two experiments confirm that G|C/G is the most desirable combination for MNAzyme activity. In addition, A|C is also a good combination for partzyme end points. GL1 stands for gene list 1 and GL2 stands for gene list 2. Number in parentheses is the sample size; Superscript "x" indicates activity is significantly less than the average (P<0.05, one tail t test); circled values indicate activity is significantly greater than the average (P<0.05, one tail t test)

FIG. 7. GG|GA at the partzyme sensor junction reduces the MNAzyme activities. *"ALL" mean all the 4 base combination at the junction tested.

FIG. 9. Relationship between pH and MNAzyme success rates. Results are classified as "Bad" (inadequate signal), "Good" (adequate signal) and "Marginal" (between "Good" and "Bad"). pH 8.2 resulted in the highest success rate among the four conditions we tested.

FIG. 11 shows the lists of genes assayed in the examples described herein. The genes used in gene list 1 (GL1), gene list 2 (GL2), gene list 3.2 (GL3), gene list 4 (GL4), and gene list 5 (GL5).

FIG. 12 shows an HBV subtype alignment and locations of primers and partzyme detecting regions used in the examples. Subsequences are labeled as follows: Limiting primer (forward primer) region (TTAAAGACTGGGAGGAGTTG (SEQ ID NO:23), underlined). Regular primer (reverse primer) region (CTCTGCCTAATCATCTCATGT (SEQ ID NO:143), underlined). Partzyme A detecting region (AGTCTTTGTACTAGGAGG (SEQ ID NO:144), bold). Partzyme B detecting region (CTGTAGGCATAAATTGGTCT (SEQ ID NO:145), bold italics). Asterisks beneath the alignment indicate a position that is identical in every sequence in the alignment.

FIG. 13 shows an HCV subtype alignment. Subsequences are labeled as follows: Limiting primer (forward primer) region (GGCGTTAGTATGAGTGTCGTG (SEQ ID NO:29), underlined); Regular primer (reverse primer) region (CTTTCTTGGATAAACCCGCTC (SEQ ID NO:146), underlined); Partzyme A detecting region (ATAGTGGTCT-GCGGAACCG (SEQ ID NO:147), bold); Partzyme B detecting region (GTGAGTACACCGGAATTGCC (SEQ ID NO:148), bold italics). Asterisks beneath the alignment indicate a position that is identical in every sequence in the alignment.

FIG. 14A-B shows an HIV-1 subtype alignment. Limiting primer (forward primer) region (CAGGAACAAATAGGATGGATG (SEQ ID NO:18), underlined). Subsequences are labeled as follows: Regular primer (reverse primer) region (GTATAGCCCTACCAGCATTCT (SEQ ID NO:149), underlined); Partzyme A detecting region (ACAAATAATCCACCTATCC (SEQ ID NO:150), bold); Partzyme B detecting region (CAGTAGGAGAAATCTATAAAAGA (SEQ ID NO:151), bold italics). Asterisks beneath the alignment indicate a position that is identical in every sequence in the alignment.

FIG. 15A-C shows primer, probe, and MNAzyme sequences that were used to detect changes in copy number of each of the identified genes. The abbreviations used with the probe sequences are as in Table 4, below. Each partzyme A included the catalytic core sequence ACAACGA (SEQ ID NO: 3) and each partzyme B included the catalytic core sequence GGCTAGCT (SEQ ID NO: 12).

FIG. 16A-B shows the results of an MCF7 DNA titration assay. MCF7 DNA was titrated with normal diploid DNA in different concentration. Copy number of the target gene was determined by MNAzyme duplex PCR assay ("Observed," leftmost left bar in each group). Expected copy number (computed based on the mixing ratio of the cell line DNA and normal diploid DNA) is also shown ("Expected," rightmost bar in each group). Typical results of two genes were shown here: A) ZNF217, B) CDKN2A.

DETAILED DESCRIPTION

Figure 2A:
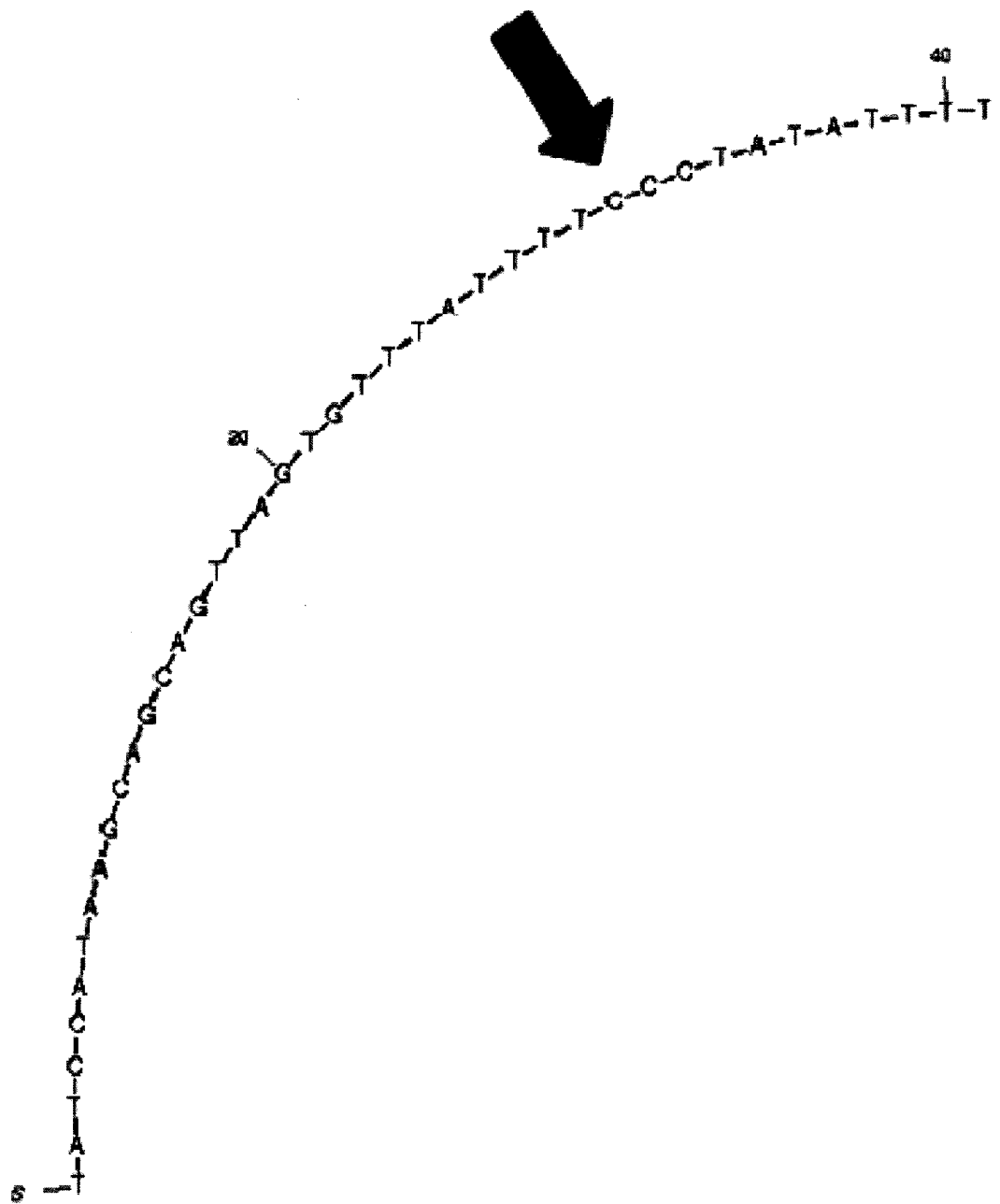
FIG. 2. Predicted secondary structure of the DNAJB4 amplicon. Arrows point to the start and end points of the MNAzyme sensor arms. The only stem-loop between the red arrows is located right in the middle of the partzyme junction.
Figure 2B:
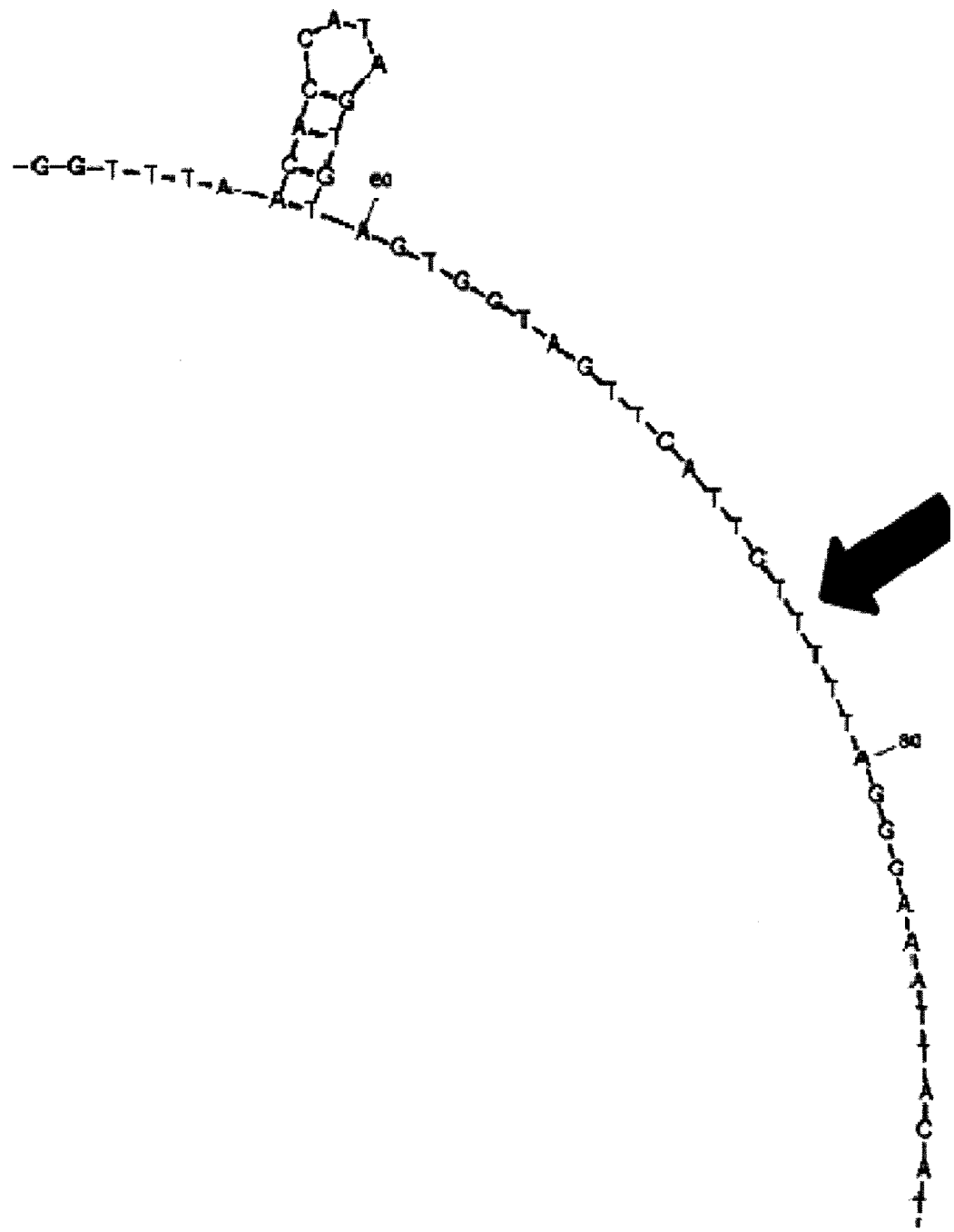
Figure 2C:
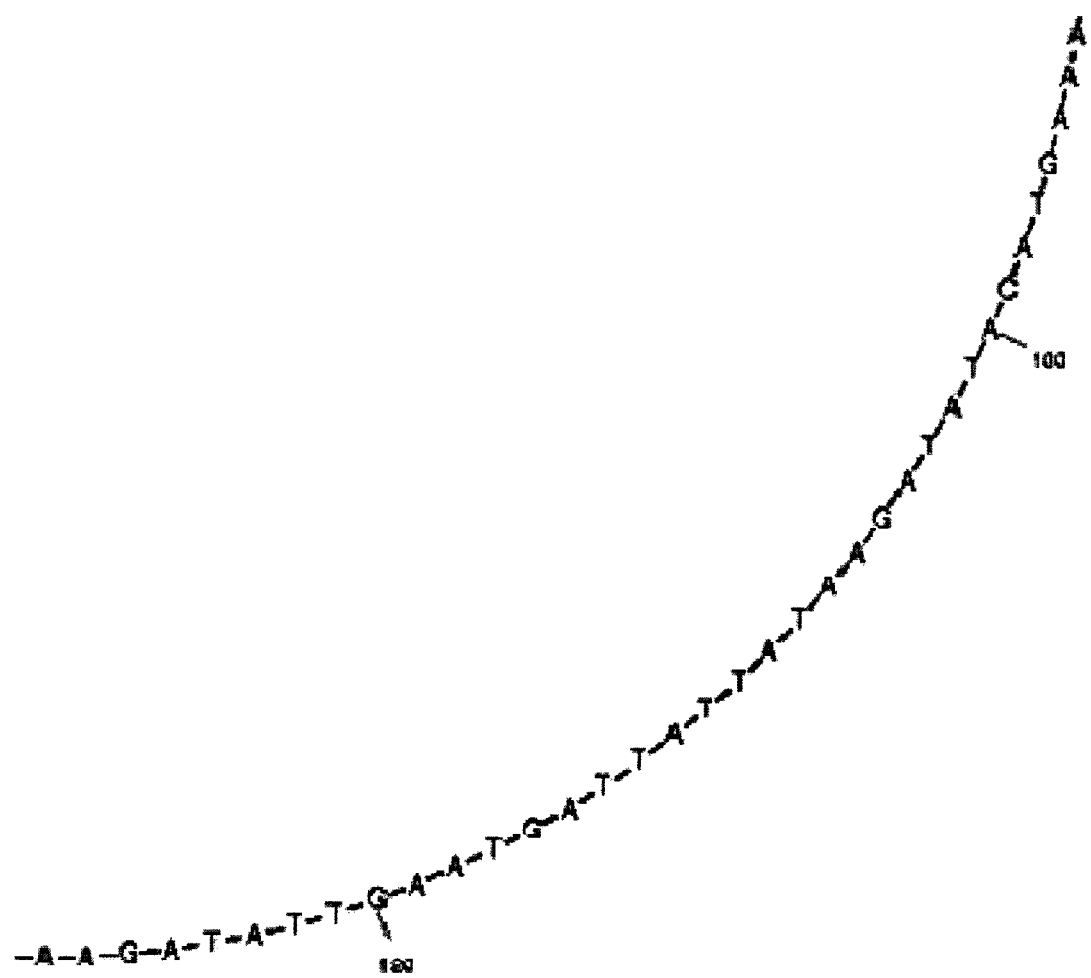
Figure 2D:
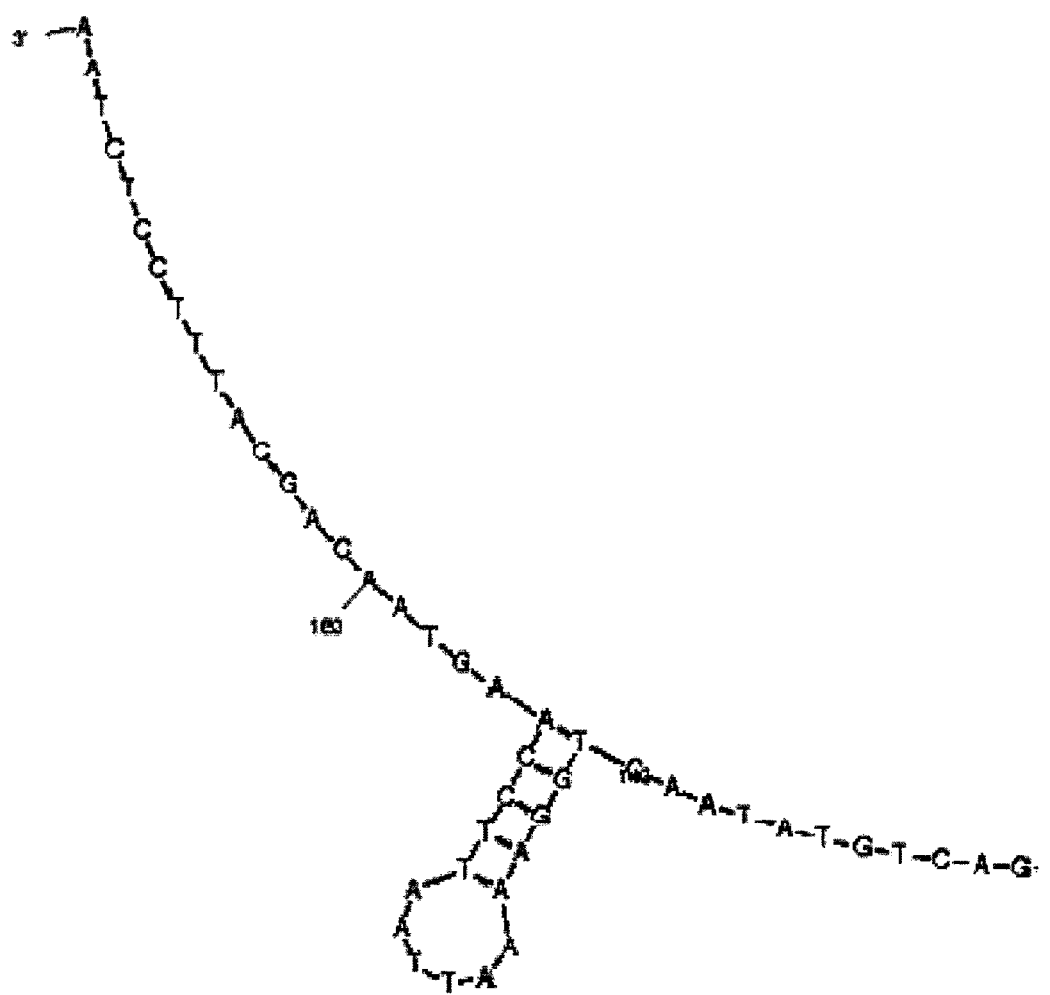

It is to be understood at the outset, that the figures and examples provided herein are to exemplify, and not to limit the invention and its various embodiments.

In accordance with the present disclosure, compositions, methods and kits are provided for the detection, identification and/or quantification of a target. The methods generally comprise the use of compositions comprising multi-component or multipartite nucleic acid enzymes which are preferably formed by multiple nucleic acid components that self assemble to form an active nucleic acid enzyme in the presence of an assembly facilitator. In preferred embodiments, the assembly facilitator is the target and therefore the multi-component nucleic acid enzymes form only in the presence of the target.

1. Compositions—MNAzymes

The Multi-component Nucleic Acid enzymes (also referred to herein equally as multipartite nucleic acid enzymes or "MNAzymes") are capable of self-assembling from two or more oligonucleotide components, also referred to herein as partzymes. The partzyme oligonucleotides self-assemble in the presence of an MNAzyme self assembly facilitator to form an MNAzyme. MNAzymes are therefore catalytically active nucleic acid enzymes. In some embodiments, the presence of an MNAzyme can be detected, and is indicative of the presence of a target, because the MNAzyme forms only in the presence of the target, wherein the target comprises the assembly facilitator. A wide variety of assays based on the basic principles outlined above are provided herein. Compositions comprising oligonucleotides capable of forming MNAzymes, and MNAzymes of various sequences are also provided herein. In some embodiments at least one of the oligonucleotide components, assembly facilitator or substrate may also include/comprise an aptamer which is capable of binding to a target.

In preferred embodiments, the MNAzyme structures are based on one or more DNAzymes and/or ribozymes. More preferred are those MNAzyme structures which are based on a particular DNAzyme structure. Presently preferred structures are based on DNAzymes including the 10:23 and 8:17 DNAzymes. In various embodiments the MNAzymes comprise either or both ribonucleotide bases and deoxyribonucleotide bases. In more preferred embodiments, an MNAzyme structure is based at least in part on the structure of a DNAzyme. In other preferred embodiments, MNAzymes comprise at least some deoxyribonucleotide bases or analogues thereof. In more preferred embodiments, the catalytic core of an MNAzyme comprises one or more deoxyribonucleotide bases or analogues thereof. In still more preferred embodiments, one or more deoxyribonucleotide bases or analogues thereof are involved in the catalysis of a substrate. In other embodiments, at least one deoxyribonucleotide base, or its analogue, in the catalytic core improves catalytic activity. In yet other embodiments, there is a strict requirement for at least one deoxyribonucleotide base, or its analogue, in the catalytic core of the MNAzyme for catalysis to occur at a measurable rate, relative to that of a comparable MNAzyme without the deoxyribonucleotide base present.

As provided herein, MNAzymes may contain one or more substitutions such as analogues, derivatives, modified or altered bases, ribonucleotides, alterations of the sugar or phosphate backbone, various deletions, insertions, substitutions, duplications or other modifications, or any combination of these, well known to those skilled in the art. Such modifications, substitutions, deletions, insertions, etc may be made in the sensor and/or substrate arms and/or in the catalytic core portions, as demonstrated herein, such that the molecule retains catalytic activity. Substitutions and modifications to arms that bind the substrate or assembly facilitator may be well tolerated and in fact are the basis of allowing tailoring of the molecules to different substrates/assembly facilitators. For example, modification of the sensor arms will allow tailoring to different assembly facilitators, while modification of the substrate arms will allow tailoring to different substrates.

Therefore, in certain preferred embodiments, the disclosure envisages MNAzymes with catalytic activity that are comprised of deoxyribonucleotides or which are derived from such molecules by certain modifications/substitutions etc. As a general rule, replacement of the whole molecule with, for example, ribonucleotides, will render the molecule inactive because it relies for its activity on certain key deoxyribonucleotides. In a corresponding fashion, some ribonucleotides in a ribozyme may be substituted with deoxyribonucleotides but replacement of the whole molecule with, for example, deoxyribonucleotides, will render the molecule inactive.

The skilled artisan will appreciate that MNAzymes comprise either deoxyribonucleotides or ribonucleotides, or even both. Those MNAzymes comprising at least one and more preferably, all, deoxyribonucleotide component oligonucleotides are presently preferred. Also preferred are those MNAzymes comprising at least one deoxyribonucleotide base, or its analogue, within the catalytic core of the MNAzyme. Even more preferred are those embodiments where such a base is required for catalytic activity.

The skilled artisan will also appreciate that multipartite DNAzymes have advantages over multipartite ribozymes, for example with respect to stability and ease of use. Thus, the multi-component MNAzymes provided herein can provide a presently preferred alternative to multi-component ribozymes, which are also provided in accordance with various embodiments. It is also to be appreciated that in certain embodiments, MNAzymes offer advantages over uni-molecular nucleic acid enzymes, for example DNAzymes, which can only recognize one substrate, whereas a single MNAzyme can recognize two molecules, namely an assembly facilitator (e.g. a target) and a substrate. For example, these properties of MNAzymes make them adaptable for example, for detection of targets, including in situ, in vivo or in vitro detection.

Exemplary partzyme catalytic core components are provided in Table 3 below. The partzyme A catalytic core may comprise, consist of, or consist essentially of the polynucleotides of any of SEQ ID NOs: 1-10, and the partzyme B catalytic core may comprise, consist of, or consist essentially of the polynucleotides of any of SEQ ID NOs: 11-16, or nucleotides having one, two, or three substitutions relative thereto (including substitution with a modified nucleic acid or substitution of RNA for DNA or DNA for RNA). Particularly preferred are a partzyme A catalytic core comprising, consisting of, or consisting essentially of SEQ ID NO: 3, and a partzyme B catalytic core comprising, consisting of, or consisting essentially of SEQ ID NO: 12.

TABLE 3

Exemplary MNAzyme catalytic core sequences.

| SEQ ID | Sequence (DNA except where noted) |
|--------|-----------------------------------|
| 1 | tacaacga (position 2 is RNA) |
| 2 | cggtcgaa |
| 3 | acaacga |
| 4 | tacaacga |
| 5 | tacaacga (position 7 is RNA) |
| 6 | tacaacaa |
| 7 | ttcaacga |
| 8 | tacatcga |
| 9 | tactacga |
| 10 | caacga |
| 11 | ccgagc |
| 12 | ggctagct |
| 13 | ggctagc |
| 14 | ggctaga |
| 15 | ggccagc |
| 16 | ggctagcta |

2. Methods Using MNAzymes for Detecting, Identifying or Quantifying Targets

The present disclosure provides various methods employing the use of one or more MNAzymes for the detection, identification or quantification of at least one target. In one embodiment, first and second oligonucleotide components self-assemble only when contacted with a sample containing an assembly facilitator, said self-assembly of the catalytically active MNAzyme thereby indicating the presence of the assembly facilitator, wherein the assembly facilitator is the target. In other embodiments, such as for example those involving an aptamer, the assembly facilitator may not be the target, and thus may comprise only an element required for self-assembly of the MNAzyme.

Generally provided are MNAzyme-based methods that allow detection of at least one target using only nucleic acid enzymes without any need for protein enzymes such as polymerases. Although the use of protein enzymes in conjunction with MNAzymes is not excluded herein, and in certain embodiments herein the inclusion of protein enzymes is permissible, or even preferred, the reaction conditions for methods that do not require protein enzymes are generally less restrictive and more readily optimized, for example for the efficiency of MNAzyme cleavage. The lack of requirement for protein enzymes also generally decreases the cost of reagents.

As further provided herein, some methods of employing MNAzymes for target detection do not require thermocycling and/or denaturation of a target. Isothermal methods are more flexible than methods requiring thermocycling and can also enable differentiation between targets comprising single stranded and double-stranded nucleic acid. Further, the lack of a need for thermocycling may make such methods easier and less expensive. Provided in accordance with the methods herein are simple, fast, cost effective, isothermal, and procedurally-flexible methods of detecting targets of interest in a sample, which may be synthetic or natural.

Certain of the examples provided herein demonstrate detection of a nucleic acid target by target-specific assembly of an MNAzyme leading to MNAzyme-mediated cleavage of, for example, a fluorescent reporter substrate. Furthermore, due to the nature of the MNAzyme molecule, reactions can be performed over a wide range of temperatures, subject only to the requirements for the assembly of MNAzyme and catalytic modification (e.g. cleavage) of the substrate utilized.

A basic example of a MNAzyme may comprise partzyme A and partzyme B which can base-pair with a target molecule, allowing the catalytic core to come into close proximity and thereby form. The substrate arms of the MNAzyme can then interacted with and base-paired with a substrate. Thus the MNAzyme can self-assembled and this process is facilitated through the presence of the target. In the absence of the target, no MNAzyme will form. Modification (in this case, cleavage) of the substrate is catalyzed by the catalytic core of the MNAzyme at the MNAzyme Cleavage Site within the substrate. The substrate in this particular embodiment of the disclosure comprises a detectable portion having a detectable signal, for example fluorophore F, and a quencher portion having a quenching effect on the detectable signal F through the action of quencher Q. Upon cleavage at the MNAzyme Cleavage Site, there is a substantial increase in detectable signal, here fluorescence, which is readily detected or quantified.

This embodiment be understood to depict an example of a basic method of using MNAzymes to detect a target, which in some embodiments comprises an assembly facilitator. Strategy 1 uses MNAzymes adapted for detection of the targets including DNA, RNA and proteins. The reporter substrate can be either free in solution or bound to a support. Signal can be generated by various means such as separation of fluorophore F and quencher Q dye pairs.

More specifically, partzyme A and partzyme B can each comprise a substrate arm portion, catalytic core portion, and a sensor arm portion. In the presence of a target, the sensor arm portions of partzyme A and partzyme B can begin to hybridize to, and base pair with complementary portions of the target, for example a DNA or RNA sequence. Upon contacting the target in this fashion, the MNAzyme self-assembles forming a catalytic core which can modify a substrate which is bound by the substrate arms. Preferably the presence of the MNAzyme is detected through the detection or measurement of its catalytic activity. The substrate arms of the thus assembled MNAzyme can engage a substrate through the interaction of the complementary sequences on the substrate arms and the substrate. Once the substrate is so engaged with the substrate arms, the catalytic core can promote the modification (e.g. cleavage) of the substrate, which can in turn be measured or detected, directly or indirectly.

There are several possible exemplary applications of an MNAzyme assay. Strategy 1 exemplifies a basic application of the MNAzyme assay as described above. An MNAzyme composed of two separate oligonucleotides with recognition sequences for both a target and a substrate forms when the oligonucleotides recognize and bind a target. The substrate, e.g. reporter substrate, is modified by the catalytic action of the MNAzyme and causes generation of a detectable signal, either directly (Strategy 1), during or after target amplification (Strategy 2) or via a signal cascade (Strategy 3). In some embodiments, both target and signal amplification occur simultaneously.

One skilled in the art would recognise that MNAzymes can be used in strategies for detection, identification or quantification of assembly facilitators that cover a broad range of application areas. These areas include, but are not limited to, medical, veterinary, agricultural, food technology, imaging and bioterrorism applications.

It will also be readily apparent to a skilled artisan that MNAzymes can be used to detect, identify and/or quantify targets in solution. For example, strategies involving detecting, identifying and/or quantifying single targets using a single substrate are applicable to such detection. In some embodiments this may involve the use of a generic substrate. Multiple targets can also be detected in solution using multiple MNAzymes which modify a series of generic substrates, the modification of each substrate resulting in a distinctly detectable signal e.g. different fluorescence.

3. Methods Using Multiple MNAzymes

The skilled artisan will recognize that the various assays provided herein can generally be used to detect a single target per reaction or assay, or to detect multiple targets in a single reaction or assay. When detecting multiple targets, one or more MNAzymes can be used depending on the assay and what is to be detected. For example, a single MNAzyme may suffice where detecting multiple related structures, for example a group of sequences sharing a critical sequence (recognized by the MNAzyme) and varying only for example, in length, or in sequence outside of the critical sequence. Any sequence with the critical sequence could be detected. Multiple MNAzymes would be useful where detecting related sequences differing by as little as a single nucleotide or even where vastly different targets are being detected, and it desirable to know the presence or absence of each. Similarly, in some embodiments a single substrate will suffice, while in others a unique substrate is required to detect each of several targets. In some cases, to multiplex the method requires the use of a distinct or unique detectable signal for each substrate to facilitate the design of the method. A distinct or unique detectable signal for each substrate may not be required when the substrates are affixed to a support or supports and can be distinguished by virtue of their localization on the support or supports. These design features will be readily understood by one skilled in the art. In some embodiments, the methods allow detection of a variety of different types of target in one reaction, e.g. a nucleic acid target and a protein.

4. Methods Using Target Amplification

The skilled artisan will readily appreciate that the methods described herein may involve amplification of a target before, during or after MNAzyme catalytic activity. Such target amplification finds particular application in embodiments of the present disclosure where the amount of target being sought to be detected, identified or quantified is of such quantum so as to provide a signal that may otherwise not be detectable. Such amplification may comprise one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR).

Strategy 2 exemplifies the use of an MNAzyme adapted to monitor the accumulation of amplicons during, or following, in vitro amplification of nucleic acid targets. Techniques for in vitro amplification of nucleic acid sequences are known in the art. These include techniques mediated by a DNA polymerase, such as the polymerase chain reaction ("PCR") (see, for example, U.S. Pat. No. 4,683,202; U.S. Pat. No. 4,683,195; U.S. Pat. No. 4,000,159; U.S. Pat. No. 4,965,188; U.S. Pat. No. 5,176,995) (Saiki et al., 1985; Chehab et al., 1987), strand displacement amplification ("SDA") (Walker et al., 1992), rolling circle amplification ("RCA") (Lizardi et al., 1998), reverse transcription polymerase chain reaction (RT-PCR) and loop-mediated isothermal amplification ("LAMP") (Notomi et al., 2000; Nagamine et al., 2002). Other target amplification techniques are mediated by an RNA polymerase, for example, transcription-mediated amplification ("TMA") (Jonas et al., 1993), self-sustained sequence replication ("3SR") (Fahy et al., 1991) and nucleic acid sequence replication based amplification ("NASBA") (Compton, 1991).

The amplification products ("amplicons") produced by PCR, RT-PCR, SDA, RCA and LAMP are composed of DNA, whereas RNA amplicons are produced by TMA, 3SR and NASBA.

With further reference to strategy 2, the disclosure provides methods of using MNAzymes in conjunction with target amplification methods which include, for example, the aforementioned PCR, RT-PCR, SDA, RCA, LAMP, TMA, 3SR and NASBA. Examples 4, 5, 6, and 9 of US 2007/0231810 demonstrate the detection of PCR amplicons. In these examples, end point analysis following PCR facilitated rapid determination of the presence or absence of the target nucleic acids. Examples 8, 10, 11, 13, 14, 15, 16, 19, and 20 in US 2007/0231810 exemplify real time monitoring of PCR amplification, thus permitting quantification of the target nucleic acid. The accumulation of amplicons produced by PCR using either asymmetric or symmetric primer ratios can be monitored using MNAzymes.

In strategy 2 a target nucleic acid may be amplified in accordance with a procedure for amplifying that nucleic acid (i.e. DNA or RNA). Preferably, standard methods of in vitro amplification are used. The amplicons generated during the amplification serve as targets for an MNAzyme, thus MNAzyme activity is indicative of the presence of the target. The skilled artisan will appreciate that such monitoring can be conducted in a single vessel under conditions that permit both the amplification and the MNAzyme assembly and catalytic activity, or the MNAzyme assay can be conducted subsequent to, or at time points throughout, the amplification, by removing samples at the end or during the course of the amplification reactions.

It is also to be appreciated that methods or protocols that combine target amplification with catalytic nucleic acid activity may require specific reaction conditions. Preferably, reaction conditions are compatible with both polymerase activity (for amplification), and catalytic nucleic acid modification of a substrate (for detection). Protocols for determining conditions for concurrent catalytic activity and polymerase activity at high temperature, such as during PCR, have been described for DNAzymes (Impey et al., 2000). The influence of factors including DNAzyme arm length, buffer, temperature, divalent ion concentration and effects of additives was demonstrated in this paper. DNA enzymes are suited for use in combination with in vitro amplification strategies. For example, they are not irreversibly denatured by exposure to high temperatures during amplification.

5. Methods Using Insoluble and Solid Supports

It is also to be understood that generally the methods, whether multiplexed or not, are applicable in solution, or combined with an insoluble support or solid support on which one or more of substrate, enzyme or portion thereof, MNAzyme assembly facilitator and/or target are bound, attached or tethered. Again the features of such assay systems will be generally understood by the skilled artisan provided with the methods and variations exemplified herein and the working examples. Thus, the invention is not to be considered limited to the literal teachings herein, but is capable of being modified and varied consistent with the principles and scope of the teachings provided herein and the knowledge in the art.

Another exemplary method for detecting targets using an MNAzyme and a substrate anchored to a support is also contemplated. In this embodiment, the substrate is preferably a substrate as shown with a detectable portion comprising a detectable signal, for example a fluorophore, and a quencher portion which diminishes or eliminates the detectable signal while the detectable portion and the quencher portion of the substrate remain in close proximity, for example, until the substrate is modified e.g. by cleavage. The substrate is attached to a support. Preferably the support is an insoluble material, or a matrix which retains the substrate and excludes it from freely moving in the bulk of the reaction mixture. Such supports are known in the art for immobilizing or localizing substrates, including nucleic acid targets. The skilled artisan will appreciate that the support can be selected from a wide variety of matrices, polymers, and the like in a variety of forms including beads convenient for use in microassays, as well as other materials compatible with the reaction conditions. In certain preferred embodiments, the support can be a plastic material, such as plastic beads or wafers, or that of the well or tube in which a particular assay is conducted.

The attachment of the substrate to the support is designed such that upon modification, e.g. by cleavage, of the substrate by the MNAzyme, either the detectable portion or the quencher portion, but not both, remains attached to the support, while the other is freed to move into the bulk of the reaction mixture, away from the portion remaining attached. Thus, in a cleavage example, the detectable signal vastly increases as the quencher portion and the detectable portion are separated upon cleavage. In an embodiment the fluorophore-containing detectable portion remains attached after cleavage. This has the benefit of allowing localization of the signal on the support but in certain instances, the fluorophore/ s may be released into solution. In a further embodiment where, for example, ligation occurs, the quencher may be ligated to a fluorophore thus decreasing the detectable signal.

A multiplexed method comprising multiple MNAzyme components for making multiple MNAzymes specific for different targets is also contemplated. This embodiment encompasses a structure which comprises a substrate in a particular known position, e.g. a "chip", where multiple positions are available to bind numerous substrates, e.g. Substrate 1, Substrate 2. The detectable portion of each substrate can be traced to its position and is tethered at that location. For each MNAzyme, e.g. MNAzyme 1, MNAzyme 2, if the target, e.g. Target 1, Target 2, is present in, for example, a test solution, the MNAzyme corresponding to and specific for that target will self-assemble and be able to catalyze the cleavage of its corresponding substrate, resulting in the production of a signal at that location. The position of the detectable signal will thus identify which MNAzyme has cleaved its substrate, and thus which target(s) is present in the test solution. In this embodiment, the modification of the substrate results in an identifiable signal by virtue of its location. The substrate does not need an independently identifiable detection mechanism, e.g., a different fluorophore, although persons skilled in the art would recognize that such contemplation is within the scope of the present invention.

Embodiments of the present disclosure encompassing an insoluble support in the form of a "chip", otherwise known as an array or microarray, typically comprise a plurality of substrates coupled, tethered or otherwise attached to the chip. In particular embodiments, the substrates comprise a nucleic acid. A plurality of nucleic acids may be positioned upon the chip by any suitable method known in the art, for example, by pipette, ink-jet printing, contact printing or photolithography. The chip may be comprised of at least one element, with each element comprising at least one nucleic acid. The at least one element may be comprised of a plurality of nucleic acids of the same sequence. The number of elements comprising a chip may be any number, and where a plurality of elements is positioned on a chip, the elements may be spaced apart at a uniform or a variable distance, or a combination thereof. In some embodiments, the elements may be positioned randomly, with the respective location of each element then determined. The size and shape of the elements will depend upon the particular application of the presently disclosed methods, and different sized and shaped elements may be combined into a single chip. The surface of the chip may be substantially planar or may have features such as depressions or protuberances, and the elements may be positioned either into the depressions or onto the protuberances. Such depressions may provide a reservoir for solutions into which the elements are immersed, or such protuberances may facilitate drying of the elements. For example, elements may be placed in each well of a 96 well plate. In some embodiments, the chip may include unique identifiers such as indicia, radio frequency tags, integrated devices such as microprocessors, barcodes or other markings in order to identify each of the elements. The unique identifiers may additionally or alternatively comprise the depressions or protuberances on the surface of the array. Furthermore, the unique identifiers can provide for correct orientation or identification of the chip. The unique identifiers may be read directly by a data capture device or by an optical scanner or detector.

6. Reporter Substrate Systems Used in the Methods

Also provided in accordance with the present disclosure are generic reporter substrate systems, which allow rapid assay development by allowing facile design changes to create new MNAzymes which recognize different targets. As discussed herein, the substrate arm portion and the catalytic core portion of the partzymes may remain unchanged, with changes only to the sensor arm portion of one or more partzymes required for new targets. Generic substrate sequences are provided and the same substrate can therefore be incorporated in assays for many different targets. Further, the same substrate can be incorporated into the methods in various embodiments herein, including assays where the substrate is free in solution or is tethered or attached to a support. A series of generic substrates can be used in a multiplex reaction allowing simultaneous detection of multiple targets.

MNAzyme strategies using generic substrates offer a major advantage over technologies such as TaqMan® or Beacons which require the design and use of probes specific for each new target.

7. Substrates Used in the Methods

As described in more detail below, MNAzymes have an advantageous property in certain embodiments of being able to utilize a universal or generic substrate. In one configuration the substrate comprises both a detectable portion and a quencher portion. The quencher portion is adapted to diminish or eliminate a detectable signal from the detectable portion of the substrate until the substrate is cleaved by the MNAzyme. For example, the quencher portion may comprise "Black Hole Quencher 1" (BHQ1) or "Black Hole Quencher 2" (BHQ2).

Thus, the MNAzyme cleaves the substrate between the detectable portion and the quencher portion allowing the two portions to separate in solution, thereby allowing the detectable signal to appear or increase as the quencher portion is distanced from, or effectively removed from the local environment of the detectable portion.

The use of the generic or universal substrate is enabled through the design of the MNAzyme's component partzymes. By altering only the sensor arms of the partzymes, but by leaving the substrate arms unchanged, a large variety of MNAzymes specific for each of a plurality of targets can be designed all of which utilize a universal substrate for detection. The skilled artisan will appreciate the advantages that this offers in terms of eliminating the need for customized or unique substrates for each target. Each new target requires only one or more changes in one or more of the sensor arm portions; the substrate arm portion and the catalytic core portion can remain constant. Thus, a single reporter substrate can be used for a single target using an MNAzyme, and multiple targets in a series of assays using altered MNAzymes. A plurality of reporter substrates allows multiplexing to detect multiple targets in a single assay using multiple MNAzymes, one for each target. Such multiplexed methods of using MNAzymes are readily accomplished in solution or with attachment to a support system. It is contemplated herein that multiplexed assays can thus be accomplished in systems involving attaching one or more of the substrate, or the MNAzyme partzymes or assembly facilitator, or additional enzyme activities, to a support as described herein.

Further, the substrates may incorporate additional entities such as labeled nucleic acids, nanoparticles, microparticles, proteins, antibodies, RNA, DNA, nucleic acid analogues, proteins, glycoproteins, lipoproteins, peptide nucleic acids, locked nucleic acids, peptide-nucleic acid chimeras, or any combination thereof. For instance, the nanoparticles may be gold nanoparticles, wherein these gold nanoparticles are associated with a plurality of targets, such as nucleic acids.

Substrates can be modified by an MNAzyme thereby providing a detectable effect. In the detection process, the substrate modification by an MNAzyme may involve, for example, cleavage, ligation, porphyrin metallation, formation of carbon-carbon bonds, ester bonds or amide bonds. As a consequence of substrate modification by an MNAzyme, a detectable effect is generated and the magnitude of the effect may therefore be indicative of the quantity of the target sought to be measured. The detectable effect may be detected by a variety of methods, including fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof.

Several groups have reported detection of nucleic acid targets, and other analytes with colourimetric readouts (Elghanian et al., 1997, Mirkin et al, 1996, and Liu and Lu, 2004). The strategy involves preparation of batches of gold nanoparticles, each of which has a distinct DNA oligonucleotide sequence attached to its surface. Gold particles can then be aggregated by the addition of a "bridging oligonucleotide", which has complementarity with the sequences that are attached to the gold particles. Particle aggregation results in a concomitant change in colour from red to blue (Mirkin et al, 1996). More recent work has shown that the inclusion of a DNAzyme substrate sequence within the bridging oligonucleotide can provide a mechanism for reversing the aggregation of the gold particles (Liu and Lu, 2004). Activation of the DNAzymes, and subsequent cleavage of the substrate/bridging oligonucleotide, resulted in the dissociation of the gold particles and a change in colour from blue to red.

A simple lead detector based on the above concept was devised which functioned by exploiting the dependence of a specific DNAzyme on lead for its catalytic activity. The DNAzyme was designed to cleave a bridging oligonucleotide used to aggregate gold particles (Liu and Lu, 2004). Similarly, an aptazyme containing an aptamer specific for adenosine, and a DNAzyme capable of cleaving a bridging oligonucleotide only in the presence of adenosine, allowed detection of adenosine in a colourimetric format.

8. Optimization of the Methods

The skilled artisan will readily understand that the methods described herein may be optimized using a variety of experimental parameters in order to optimize the detection, identification and/or quantification of a target. The particular experimental parameters that are optimized, and the level of such optimization, will depend upon the particular method being employed and the particular target being sought to be detected, identified and/or quantified. Such parameters include, but are not limited to, time, temperature, concentration of salts, detergents, cations and other reagents including but not limited to dimethylsulfoxide (DMSO), and length, complementarity, GC content and melting point (Tm) of nucleic acids.

In some embodiments, for example those methods involving detection of sequence variation and/or detection of methylated DNA, the experimental parameters, and preferably including the temperature at which the method is performed, may be optimized so as to discriminate between binding of an MNAzyme component nucleic acid to a target nucleic acid that does or does not comprise a sequence variation or a methylated nucleotide, respectively. The temperature at which such methods may be performed may be in the range of about 20° C. to about 96° C., about 20° C. to about 75° C., 20° C. to about 60° C. or about 20 to about 55° C., In one preferred embodiment, optimized reactions for practicing the methods of using MNAzymes are provided herein. In such optimized reactions, catalytic activity is increased by up to 10, 20, or 30% above unoptimized reactions. More preferred reaction conditions improve catalytic activity by at least 35%, or 40%, and preferably up to 50% or more. In still more preferred embodiments, optimized reactions have an increase of catalytic activity of more than 50%, and up to 66%, 75% or even 100%. In yet more preferred embodiments, a fully optimized reaction method will offer 100, 200 or even 300% or more increase in catalytic activity. Other preferred reaction conditions can improve the catalytic activity by up to 1000% or more over methods practiced with unoptimized reaction conditions. A highly preferred reaction condition for optimizing the methods provided herein is the inclusion of certain divalent cations. The catalytic activity of most nucleic acid enzymes may be influenced in a concentration-dependent fashion by the concentration of divalent cations. Preferred optimized reactions are optimized for one or more of Ba2+, Sr2+, Mg2+, Ca2+, Ni2+, Co2+, Mn2+, Zn2+, and Pb2+.

9. Methods Using Aptamers

Persons skilled in the art will readily appreciate that the methods described herein may be performed with aptamers, wherein said aptamers may facilitate the detection, identification and/or quantification of targets including targets other than nucleic acids.

A method of using MNAzymes to detect targets, including non-nucleic acid entities is also contemplated. This method uses aptamers which may comprise a nucleic acid or protein, polypeptide, or peptide or combination thereof that has the ability to recognize one or more ligands. Aptamers may bind, for example, proteins, polypeptides, peptides or nucleic acids, glycoproteins, lipids, lipoproteins, cells, viruses, bacteria, archaea, fungi, antibodies, metabolites, pathogens, toxins, contaminants, poisons, entire organisms, small molecules, polymers, metal ions, metal salts, prions or any derivatives, portions or combinations thereof, or any other entity (Lee et al., 2004).

Preferred aptamers herein may comprise short single-stranded DNA or RNA oligomers or peptides that can be isolated from complex libraries of synthetic nucleic acids or peptides by an iterative process of adsorption, recovery, and reamplification. Aptamers may therefore be generated against almost any target, ranging from small molecules such as amino acids or antibiotics, to protein and nucleic acid structures. In preferred embodiments, aptamers include, for example, nucleic acid binding molecules which are preferably generated by evolution and selection techniques. Preferably, aptamers may comprise DNA or RNA molecules, or a combination of both, including but not limited to the nucleotide analogues as per, for example, Table 2 above.

In such strategies for combining the use of aptamers with MNAzymes, the nucleic acid oligonucleotides required for this MNAzyme detection strategy may include; (a) a standard partzyme; (b) an apta-partzyme which is a partzyme that incorporates an aptamer (bold sequence) as well as a complementary sequence capable of forming a hairpin and therefore inhibiting MNAzyme assembly; (c) an assembly facilitator which can bind to both the apta-partzyme and the partzyme, thus enabling assembly of an active MNAzyme; and (d) a substrate. In the absence of a target analyte (An), the apta-partzyme adopts a hairpin structure which inhibits assembly of an active MNAzyme. In the presence of target analyte, the target analyte binds to the aptamer domain of the apta-partzyme, thus disrupting the hairpin structure and allowing the apta-partzyme to participate in assembly of an active MNAzyme. The active MNAzyme can then modify a substrate causing, for example, fluorescent signal generation.

The nucleic acid oligonucleotides utilized for this MNAzyme detection strategy may include; (a) two standard partzymes; (b) an assembly facilitator that incorporates an aptamer (bold sequence) as well as complementary inhibitor sequence capable of forming a hairpin structure; and (c) a substrate. In the absence of a target analyte, the assembly facilitator adopts a hairpin structure which inhibits the ability of this component to direct the assembly of active MNAzymes. In the presence of target analyte, the target analyte binds to the aptamer domain of the assembly facilitator, thus disrupting the hairpin structure and allowing the component to direct the assembly of an active MNAzyme. The active MNAzyme can then modify a substrate causing, for example, fluorescent signal generation.

One skilled in the art will appreciate that the aptamer may be incorporated into either end of the assembly facilitator molecule or molecules. Further it will be appreciated that multiple aptamers could be incorporated into one or more of the partzyme oligonucleotide components. The assembly facilitator in the strategies discussed herein can comprise DNA, RNA, LNA, PNA or a sequence containing one or more nucleotide base analogues. In other embodiments, the target An is a nucleic acid. In such embodiments, a sequence complementary to the target nucleic acid can replace part of the aptamer sequence.

The nucleic acid oligonucleotides utilized for this MNAzyme detection strategy may include two apta-partzymes, each of which contains a portion of an aptamer. In the absence of a target analyte, active MNAzymes cannot assemble. In the presence of target analyte, the target analyte serves as the assembly facilitator bringing the oligonucleotide components together thus directing the assembly of an active MNAzyme. The active MNAzyme can then modify a substrate causing, for example, fluorescent signal generation.

Another strategy, which combines aptamer binding and MNAzyme assembly, is also contemplated. In this strategy, an aptamer sequence is incorporated at the end of a partzyme (apta-partzyme) in a configuration whereby an active MNAzyme is only formed in the presence of the target analyte. The oligonucleotide components required for the MNAzyme detection strategy illustrated include; (a) a standard partzyme; (b) an apta-partzyme which is a partzyme with an aptamer incorporated into one of its ends; (c) an assembly facilitator which binds to both the apta-partzyme and the partzyme enabling assembly of an active MNAzyme (in the presence of target); (d) a reporter probe substrate; and (e) an assembly inhibitor which hybridizes to the apta-partzyme in a region which spans at least part of the aptamer sequence and part of the substrate binding arm of the partzyme sequence. In the absence of a target (left hand panel), the assembly inhibitor binds to the apta-partzyme thus blocking binding (and cleavage) of the reporter probe substrate. In the presence of a target (right hand panel), the target binds to the aptamer sequence of the apta-partzyme, preventing the binding of the assembly inhibitor and allowing the binding and cleavage of the reporter probe substrate. As such, an active MNAzyme can only form and cause fluorescent signal generation in the presence of target.

Further, it will be appreciated by one skilled in the art that the strategy as discussed above have similar aspects, with a difference being that the complementary inhibitor sequence, which prevents active MNAzyme formation, is either incorporated into an oligonucleotide partzyme component or into a separate molecule. As such, an inhibitor sequence can be a separate molecule or can be incorporated into one of the components that participate in the MNAzyme complex.

It will also be appreciated by one skilled in the art that one or more aptamers could be incorporated into any of the oligonucleotide components, including the partzymes, the assembly facilitator or the substrate. Further the aptamer could be incorporated into either end of any one of these oligonucleotides.

Exemplary embodiments are illustrated in US 2007/0231810 (e.g., examples 18 and 21) in which an aptamer/MNAzyme strategy is used to detect a small molecule (ATP) and a protein (Taq polymerase) respectively.

10. Methods for Detection, Identification and Quantification of MicroRNA

The skilled artisan will understand that the detection, identification and/or quantification of microRNA represents a particular embodiment of the methods described herein. A strategy for amplification of short nucleic acid sequences (e.g. microRNAs (miRs)) and detection of amplicons using MNAzymes is also contemplated.

Detection of short nucleic acid sequences such as microRNAs (miRs) requires additional strategies primarily due to the small size of these targets. MiRs are non-coding RNA molecules of approximately 22 nucleotides in length. They can be detected by cloning or northern blot analysis, but these methods are laborious and require larger amounts of total RNA than techniques such as RT-PCR. The small size of miRs provides insufficient sequence to accommodate two PCR primers of standard design. Further, even if miR amplification is accomplished, it is difficult to distinguish genuine amplicons from primer-dimers using either size (ascertained by electrophoresis), or fluorescence from the intercalation of non-specific dyes, such as SYBR Green or Ethidium Bromide. This limitation could be overcome by probing the miR amplicons with internal hybridization probes such as TaqMan® or Beacon probes, however, again the small size of the amplicons prohibits use of probes of standard designs.

A modified TaqMan® RT-PCR method (Chen et al., 2005) for miR analysis initiates reverse transcription using 3' primers which have miR specific 3' termini and additional unrelated sequences at their 5' termini which can form stem-loops. The cDNA generated is amplified using these 3' primers and 5' primers, which also have miR specific 3' termini and additional unrelated sequences at their 5' termini. The amplification is monitored in real time using TaqMan® probes that bind to both miR sequences and unrelated sequences introduced by the primers. However, due to the primer design, and the size and positioning of the TaqMan® probe there is a still the likelihood that specific miRs may not be distinguished from closely related sequences.

The method employed here preferably employs a 3' primer that binds to a miR at its 3' end and has an extension sequence, unrelated to the miR, which may, or may not, form a stem-loop at the 5' end. The unrelated sequence of the primer may create a loop structure or may merely create a tag structure. In either example, the 3' miR primer is extended in the presence of reverse transcriptase, followed by PCR amplification using 5' and 3' primers with miR-specific sequence at the 3' end with unrelated extension sequence at the 5' ends. The amplicons are readily detected by MNAzymes, which recognize and hybridize to the amplicon including the region between the 5' and 3' primers. The strict requirement for complementarity between the MNAzyme sensor arm and the target nucleic acid allows discrimination of even closely related sequences. Example 5 and Example 10 in the US 2007/0231810 demonstrates the results of using MNAzymes to detect amplicons generated by amplification of short nucleic acid sequences (see also strategy 2, discussed above). Further, the example 5 demonstrates the capacity of methods using MNAzymes to distinguish between two sequences having only a single nucleotide difference. This provides a major advantage in that, even when the amplification process is unable to discriminate between closely related sequences, the MNAzymes allow discrimination between minor sequence variation in the resulting amplicons.

11. Methods Using Cascades

Persons skilled in the art will appreciate that the methods described herein may be used to perform a cascade as herein defined. Particular embodiments of performing such methods as disclosed herein include, but are not limited to (1) use of an MNAzyme to cleave a substrate only in the presence of a target, wherein said substrate is then made available for involvement in a second event such as generation of a detectable signal, wherein cleavage of a substrate makes available an enzyme that may then cleave an anchor, thereby resulting in fluorescent tag dissociating from a quencher; or (2) use of an MNAzyme to cleave a substrate only in the presence of a target, wherein said substrate is then made available for involvement in a second event, wherein performance of said second event in turn makes available a further substrate for involvement in any number of subsequent events, such that a subsequent event makes available a substrate for involvement in the performance of an earlier event, thereby creating a cyclic cascade, wherein such cyclic cascades may be employed to amplify a signal, for example, in applications where the low abundance of a target may not otherwise provide for a signal that is detectable.

A detectable effect amplification cascade may comprise one or more of a ribozyme/ligase cascade, a circular nucleic acid enzyme cascade, a protein enzyme cascade, or one or more enzymes attached to a support, or any combination thereof.

Strategy 3 shows an overview of a method of using an MNAzyme to amplify a signal through the use of a signal cascade. This is discussed in more detail with reference to FIGS. 6, 7 and 25 in US 2007/0231810.

Other exemplary method of MNAzyme detection of target coupled with enzyme mediated signal amplification are also contemplated. As discussed above, the disclosure provides for methods of using MNAzyme detection wherein a target is amplified as well as methods wherein a signal generated is amplified. In some embodiments, combining MNAzyme technology with signal amplification strategies provides an alternative to MNAzyme assays combined with target amplification, although in some instances both target amplification and signal amplification can be used together. Preferred methods of amplifying signals involve cascade mechanisms, which as the skilled artisan will appreciate are often involved in amplifying signals in biological systems.

Several examples of amplification cascades, which use catalytic nucleic acids, are known in the art and are contemplated for use herein. Ligation cascades (Paul and Joyce, 2004) use a first ribozyme (A) which ligates two RNA containing oligonucleotides to form a second ribozyme (B). Ribozyme (B) then ligates two other RNA containing oligonucleotides to form a new first ribozyme (A), thus triggering a cascade reaction.

A second amplification cascade suitable for use herein uses circularized DNAzyme/substrate molecules (Levy and Ellington, 2003). A DNAzyme (A) is inactive when circular, but becomes activated by linearization by a second DNAzyme (B), which cleaves the circular DNAzyme (A). Active linear DNAzyme (A) then cleaves circular DNAzyme (B) molecules thus linearizing and activating them. The two DNAzymes capable of cleaving/linearizing each other result in a cascade of catalytic nucleic acid activity.

Persons of skill in the art will understand that other approaches are available—for example combining the use of DNAzymes with the versatility of aptamers and/or with the catalytic power of traditional protein enzymes (see e.g. Zhang et al., 2005). Zhang's method results in the release of a protein enzyme that can, in turn, catalyze the formation of detectable molecules thereby generating and amplifying signal. Zhang's approach allows sensitive detection, but it is expensive as it requires highly customized molecules for each assay. Methods for coupling of peptides to nucleic acids are known in the art (see e.g. Cheng et al., 1993), as are methods for attaching DNA to support structures. For example, Asher (PCT/US96/02380) described tethering an enzyme (ribozyme) to an insoluble support, which upon release, cleaved a substrate thereby initiating amplification of a signal using two spatially separated ribozymes.

Other examples of signal amplification for in vitro methods are known in the art, and yet other strategies for amplifying signals can be created using techniques similar to those that have proven successful. For example, the branched DNA assay (bDNA) (Urdea, 1993) amplifies a signal by employing a secondary reporter molecule (e.g. alkaline phosphatase) attached to labeled probes mediating the reaction. Fluorescence correlation spectroscopy (FCS) employs electronic amplification of the signal (Eigen and Rigler, 1994). Tyramide signal amplification (TSA) (Bobrow et al., 1989; Adams, 1992; Raap et al., 1995; van Gijlswijk et al., 1997), uses horseradish peroxidase to convert tyramiside to its active form, which binds to tyrosine residues in proteins. TSA is used for various applications of cell immunochemistry. The Invader assay (Hall et al., 2000) employs two oligonucleotides that bind to a target sequence in a manner that allows for nuclease cleavage leading to greater than 1000 cleavage events per target molecule over time, and the cleavage reaction can be coupled to a fluorescent probe. However, there are limitations to the known signal amplification methods. For example, the bDNA assay is not as sensitive as the target amplification methods.

Exemplary methods may employ an enzyme released by MNAzymes as part of a signal amplification strategy. The signal can be generated, for example, by enzyme cleavage of a substrate between a fluorophore moiety and a quencher moiety, thus allowing a signal to be generated. Enzymes contemplated for use herein include, but are not limited to, DNAzymes, MNAzymes, ribozymes, and protein enzymes with measurable activity, such as proteases, restriction endonucleases and other hydrolytic enzymes. Preferred targets are nucleic acid sequences including, but not limited to, human, animal, plant, viral, bacterial DNA or RNA. Other preferred targets may include, prion, yeast or fungus, or any other molecule, for example, including but not limited to glycoproteins, lipids, lipoproteins, entire organisms, cells, viruses, bacteria, archaea, fungi, antibodies, metabolites, pathogens, toxins, contaminants, poisons, small molecules, polymers, metal ions, metal salts, prions or any derivatives, portions or combinations thereof.

An exemplary enzyme may be attached to a first insoluble support, through a cleavable molecule, preferably a nucleic acid. The cleavable molecule acting as the attachment for the enzyme can be a generic or universal MNAzyme substrate. Also attached to an insoluble support not in contact with the first insoluble support may be a cleavable anchor substrate for the enzyme. The enzyme may be any enzyme with a detectable or other desired activity, for example an MNAzyme, DNAzyme, ribozyme, or protein enzyme as described above. In preferred embodiments, MNAzymes or DNAzymes are particularly useful. In the presence of the oligonucleotide components, or partzymes, that self assemble to form an MNAzyme capable of cleaving the universal or generic substrate, and in the presence of the target for the MNAzyme, the MNAzyme forms and catalytically cleaves the enzyme from the support, thereby freeing it and allowing it to access the cleavable anchor substrate and cleave it. Cleavage of the cleavable anchor may release the fluorophore from the attached substrate. The fluorophore is readily detected and measured.

The physical separation of an immobilized or attached enzyme from its substrate, which is preferably also immobilized or attached to a support, is sometimes referred to herein as "spatial separation." One or more enzymes can be "spatially separated" from their respective substrates, and from each other. A signal amplification cascade can result, particularly where the cleavage of the substrate for the first enzyme releases the second enzyme, which in turn releases more first enzyme when the substrate for the second enzyme is cleaved.

In preferred embodiments, the substrate for the enzyme may be a bifunctional substrate comprising both a quencher portion and detectable portion. Particularly preferred are embodiments wherein the substrate for enzyme is a molecule with no detectable signal while in the uncleaved substrate, and whose detectable signal increases by one to many orders of magnitude upon cleavage.

Another exemplary assay using MNAzymes and a signal amplification using two "spatially-separated" enzymes is also contemplated. A signal amplification cascade can also be generated using such "spatially separated" DNAzymes as described above. An initial MNAzyme cleavage event cleaves an immobilized tethered substrate, thereby releasing DNAzyme A. DNAzyme A then migrates to a second sequence where a second DNAzyme B is tethered. DNAzyme A releases DNAzyme B that, in turn, releases more of DNAzyme A. A cascade is initiated that results in signal amplification. In various embodiments, the target can be nucleic acid sequences including, but not limited to, human, viral, bacterial DNA or RNA; or the target can be proteins, viruses, prions, antibodies, whole cells or small molecules.

In particular, it can be seen from the discussion above that DNAzyme A may be attached to a support through a first universal MNAzyme substrate or generic substrate, which is also cleaved by DNAzyme B. DNAzyme B may be attached to an insoluble support through a second generic substrate that is a substrate for DNAzyme A. Both DNAzymes are retained such that their respective substrates are inaccessible to them. In the presence of the partzymes that self assemble to form an MNAzyme that cleaves the universal substrate, and in the further presence of the target, the MNAzyme is formed and cleaves the universal MNAzyme substrate retaining DNAzyme A, thereby releasing DNAzyme A. DNAzyme A can now migrate to the second generic substrate. Upon cleavage of the second generic substrate by DNAzyme A, DNAzyme B is released along with its attached detectable signal, shown here as a fluorophore F. Fluorophore F is now detectable as it separates from a retained quencher portion Q. Freed DNAzyme B, now able to access its substrate does so, cleaving it (the first generic substrate) and thereby releasing additional DNAzyme A, which in turn releases more DNAzyme B and detectable signal F. Thus, a powerful signal amplification cascade is established, with exponentially increasing amounts of detectable signal F.

Another exemplary embodiment of an MNAzyme cascade using tethered partzymes is also contemplated. MNAzymes can be used to initiate signal amplification cascades as illustrated in this discussion. The reaction may contain the following elements; (i) partzymes for MNAzyme 1 which are free in solution; (ii) an assembly facilitator for MNAzymes 2 and 3 (which have the same sensor arms) which is either free in solution (as illustrated) or tethered to an insoluble support by substrate, Sub 1; (iii) partzymes for MNAzyme 2 which are tethered to an insoluble support by the substrate, Sub 1. Sub 1 can be cleaved by either MNAzyme 1 (in the presence of a target analyte) or MNAzyme 3 (in the presence of an assembly facilitator), and cleavage results in the release of the partzymes for MNAzyme 2 into solution; (iv) partzymes for MNAzyme 3 which are tethered to an insoluble support by the substrate, Sub 2. Sub 2 can be cleaved by MNAzyme 2 (in the presence of assembly facilitator) and cleavage results in the release of the partzymes for MNAzyme 3 into solution; (v) Sub 2-FQ, which has the same sequence as Sub 2, but is free in solution and is dual labelled with a fluorophore (F) and a quencher (Q). Sub 2-FQ can be cleaved by MNAzyme 2 to generate a fluorescent signal.

In the presence of the target analyte, active MNAzyme 1 forms from partzymes that are free in solution. MNAzyme 1 cleaves its Sub 1 thus releasing partzymes for MNAzyme 2. Once free, these partzymes hybridize with the assembly facilitator and form MNAzyme 2, which cleaves free Sub 2-FQ (generating a fluorescent signal), or tethered Sub 2 (releasing partzymes for MNAzyme 3). Since MNAzyme 3 shares the same substrate arms as MNAzyme 1, it can also cleave tethered Sub1, thus releasing more partzymes for MNAzyme 2. This results in a cascade of enzymatic generation of the components (partzymes) for more enzymes (MNAzymes) and a concomitant signal amplification cascade.

12. Methods for the Detection, Identification and Quantification of Methylated Nucleic Acid MNAzyme mediated signal generation allows discrimination between fully matched nucleic acid sequences and those containing mismatches. This capacity enables MNAzymes to be used for the detection, identification and quantification of methylated nucleic acid.

Alterations in methylation pattern occur frequently in association with diseases such as cancer, diabetes, autoimmune diseases, and psychiatric disorders. The vast majority of protocols currently used for methylation analysis begin with bisulphite modification of genomic DNA. Bisulphite modification converts unmethylated, but not methylated, cytidines to uridines. If the bisulphite modified nucleic acid is then amplified, for example by PCR, the uridines are replaced with thymidines and the methylated cytidine is replaced by cytidine. The modified amplicons can be analyzed by various methods that allow discrimination of the sequences containing T (in positions originally containing unmethylated C) and C (in positions originally containing methylated C).

The capacity for MNAzymes to discriminate between closely related sequence variants makes this technology well suited for discriminating between bisulphite modified sequences which were originally either methylated or unmethylated. The approach may be better understood by reference to US 2007/0231810 (example 11).

Further, MNAzymes can provide a new approach allowing the direct analysis of methylated and unmethylated DNA without the need for bisulphite modification. This provides a significant advantage because bisulphite modification is laborious, time consuming and destructive to the nucleic acid to be analyzed.

The use of a stabiliser arm with a partzyme that has a truncated sensor arm has been used to demonstrate the capacity of MNAzymes to detect single nucleotide polymorphisms present in assembly facilitators. See US 2007/0231810 (Example 22). Under the experimental conditions used in that example, a partzyme with a truncated (five base) sensor arm was functional at a temperature well above its expected melting temperature. Systems with stabiliser arms, and partzymes that have truncated sensor arms, are very sensitive to small changes in the target, and are amenable to use at highly stringent temperatures. This detection strategy can be further extended to discriminate directly between targets, which are either methylated or unmethylated at specific cytosine residues, without the need for prior bisulphite modification.

The presence of 5-methylcytosine(s) increases the melting temperature of DNA by 1.3° C. per methylated base, relative to unmethylated cytosine(s). When partzymes, a stabiliser arm, and a substrate are incubated at a temperature, which is suitable for hybridization and active MNAzyme assembly in the presence of a methylated target, but which is too high for MNAzyme assembly in the presence of an unmethylated target, a signal would be generated only in the presence of the methylated target. This provides a new strategy for direct analysis of methylation patterns that can provide a method for detection of methylation bases as markers of cancer and other diseases.

Skilled artisans will therefore readily appreciate and understand that the optimization of experimental parameters including temperature as herein disclosed is contemplated as being within the scope of the methods of the present disclosure, and that such optimization finds particular application in the performance of methods relating to detection of methylated DNA either directly or after bisulphite modification.

13. Methods for the Detection and Identification of Nucleic Acid Sequence Variants The present disclosure further provides for methods for the detection and identification of sequence variants on the basis that MNAzyme mediated signal generation allows discrimination between fully matched nucleic acid sequences and those containing mismatches.

Sequence variations capable of detection by the methods of the present disclosure include, but are not limited to, additions, deletions, substitutions, conversions, duplications, translocations, frame-shift sequence variants, nonsense sequence variants, or any combination thereof.

The methods may be applied in any situation in which it is desirable to detect and/or identify a nucleic acid sequence variation, including but not limited to diagnosis of diseases or predispositions thereto, identification of polymorphisms, or assessment of nucleic acid replication fidelity. In addition, larger alterations such as translocations associated with various cancer types, which result in fusion transcripts, may also be detected. These occur frequently in association with leukaemia. For example, PML/RARα fusion transcripts are associated with acute promyelocytic leukaemia and bcr/abl fusion transcripts are associated with chronic granulocytic leukaemia.

MNAzyme-mediated target detection can occur via Watson-Crick base recognition of the partzyme sensor arms and the assembly facilitator. The requirement for complementarity can be exploited to detect small sequence variations, including but not limited to, single base mismatches between the partzyme sensor arm and the assembly facilitator. The capacity for discrimination of sequence variants may be better understood by reference to US 2007/0231810 (examples 5, 19 and 22).

Those examples all demonstrate the capacity of MNAzymes to discriminate between situations where the sensor arm and assembly facilitator are fully matched, and situations where there is at least a single base mismatch or polymorphism.

The capacity to discriminate single base mismatches is dependent on several factors including (a) the stringency of the reaction conditions, which can be influenced by many factors including temperature, salt concentration, cation concentration, (b) the type of mismatch, (c) the position of the mismatch within the partzyme arm, and (d) the length of the partzyme arm. Depending on the application, the stringency of the reaction can be tailored to be either intolerant, or tolerant, to some degree of mismatch between the sensor arm and the assembly facilitator. Stringent conditions allow discrimination of closely related sequence variants, such as a single nucleotide difference. Lower stringency conditions may not discriminate between assembly facilitators with closely related sequences. Therefore, this could be exploited to detect simultaneously a group of closely related sequences in a single reaction with a single MNAzyme.

The discrimination of single nucleotide polymorphisms can be extended by the use of partzymes with truncated sensor arms. Truncated sensor arms can be stabilized by a stabilizer oligonucleotide component, which although a separate molecule, can be considered as a second component of the truncated partzyme, to which it binds adjacently.

14. MNAzymes for Detection, Identification and/or Quantification of Bacteria and Viruses The present disclosure encompasses methods for the detection of bacteria, viruses or any other microorganism, for example, through design of MNAzyme sensor arms that are adapted to hybridize to any molecule such as a nucleic acid that is unique to the microorganism that is sought to be detected, identified and/or quantified. Additionally or alternatively, a class of microorganism may be detected, for example, including but not limited to Gram positive or Gram negative bacteria. Further variations of the methods that are within the scope of contemplation of the person skilled in the art include, but are not limited to, use of an aptamer adapted to bind a protein, small molecule, cell, cellular component or cellular product such as a toxin that is unique to the microorganism that is sought to be detected, identified and/or quantified.

Bacteria and viruses contain DNA and/or RNA which can provide a template for their rapid and sensitive identification, detection and/or quantification using MNAzyme technology. Sequence variation between bacterial and viral species and strains can be used to allow sensitive discrimination between individual species and strains. Multiplex MNAzyme approaches are particularly preferred for the simultaneous detection and/or discrimination of multiple bacterial or viral species, strains or isolates.

Alternatively, regions of sequence similarity across bacterial or viral species and strains can be used to identify the presence or absence of any of a group of individual species and strains in a single MNAzyme assay. This latter approach is exemplified in US 2007/0231810 (Example 15) where a conserved region found in bacterial ribosomal 16S sequence was used as the basis of an assay to replace the bacterial test of a Gram stain for a rapid release test for sterility and/or mycoplasma contamination.

US 2007/0231810 (Example 16), which illustrates the use of MNAzymes for the detection and quantification of HIV-1 viral RNA, demonstrates the use of MNAzymes as a sensitive tool for viral detection and quantification.

15. Kits

The present disclosure also provides kits for practicing the methods disclosed herein. Typically, kits for carrying out the methods of the present disclosure contain all the necessary reagents to carry out the method. For example, in one embodiment a kit may comprise a first container containing at least a first and second oligonucleotide component comprising a first and second partzyme, and a second container comprising a substrate, wherein self-assembly of the first and second partzymes, and the substrate, into an MNAzyme requires association of an assembly facilitator present in a test sample. Accordingly, in such embodiment, the first and second partzymes, and the substrate, may be applied to the test sample in order to determine the presence of the assembly facilitator, wherein the assembly facilitator comprises the target.

Typically, the kits of the present disclosure will also comprise one or more other containers, containing for example, wash reagents, and/or other reagents as required in the performance of the methods of the disclosure.

In the context of the present disclosure, a compartmentalized kit includes any kit in which reagents are contained in separate containers, and may include small glass containers, plastic containers or strips of plastic or paper. Such containers may allow the efficient transfer of reagents from one compartment to another compartment whilst avoiding cross-contamination of the samples and reagents, and the addition of agents or solutions of each container from one compartment to another in a quantitative fashion. Such kits may also include a container which will accept the test sample, a container which contains the reagents used in the assay, containers which contain wash reagents, and containers which contain a detection reagent. Typically, a kit of the present disclosure will also include instructions for using the kit components to conduct the appropriate methods. Kits and methods of the disclosure may be used in conjunction with automated analysis equipment and systems, for example, including but not limited to, real time PCR machines.

For application to detection, identification or quantitation of different targets, a single kit of the present disclosure may be applicable, or alternatively different kits, for example containing reagents specific for each target, may be required. Methods and kits of the present invention find application in any circumstance in which it is desirable to detect, identify or quantitate any entity.

The present invention will now be further described in greater detail by reference to the following specific examples, which should not be construed as in any way limiting the scope of the invention.

EXAMPLES

Example 1

This example illustrates the high failure rate using conventional MNAzyme methodology.

MNAzyme technology, a method for detecting and quantification of real-time PCR that is generally known as an alternative method to the TaqMan based detection and quantification system. Primers, MNAzymes, and probes for real-time PCR amplification of target sequences with MNAzyme detection were designed according to conventional methods, for example as disclosed in US 2007/0231810, WO/2007/041774, and Mokany et al., J Am Chem. Soc. 2010 Jan. 27; 132(3): 1051-1059. The overall success rate was 62% (FIG. 1, GL1 and GL2). This real-time PCR design success rate were significantly lower than real-time PCR design success rate for SYBR Green I-based detection method (which take no consideration of potential secondary structure). The conventional MNAzyme design method employed attempts to avoid secondary structures within the amplicon, which constrained the choice of amplicon and contributed to the failure rate. The MNAzyme design success rate is also low (FIG. 1) when assessed by an isothermal test using the synthesized target for the MNAzyme, indicating that both PCR failure and low or absent MNAzyme activity contributed to the overall low success rate.

FIG. 1 summarizes the large-scale MNAzyme design and experimental verification results. Total design: total number of genes that have been designed for MNAzyme detection of PCR amplification. The genes used in gene list 1 (GL1), gene list 2 (GL2), gene list 3.2 (GL3), gene list 4 (GL4), gene list 5 (GL5) are listed in FIG. 11. Results reported for GL1&2 utilized PCR primers and MNAzymes designed using conventional methods. Out of 178 total designs, only 110 succeeded. For 29 designs (16% of total) failure was attributable to PCR; this relatively high rate PCR failure is apparently attributable to one of the constraints imposed by conventional MNAzyme design, namely selection of a PCR target free of predicted secondary structure. The overall success rate was 62%. In contrast, results reported for GL3-5 achieved an overall 90% success rates utilizing the methodologies described below, which both avoid the aforementioned constraint for selection of the PCR target and thus reduced the PCR failure rate by over 4-fold, and provide further improvements.

Example 2

Figure 3A:
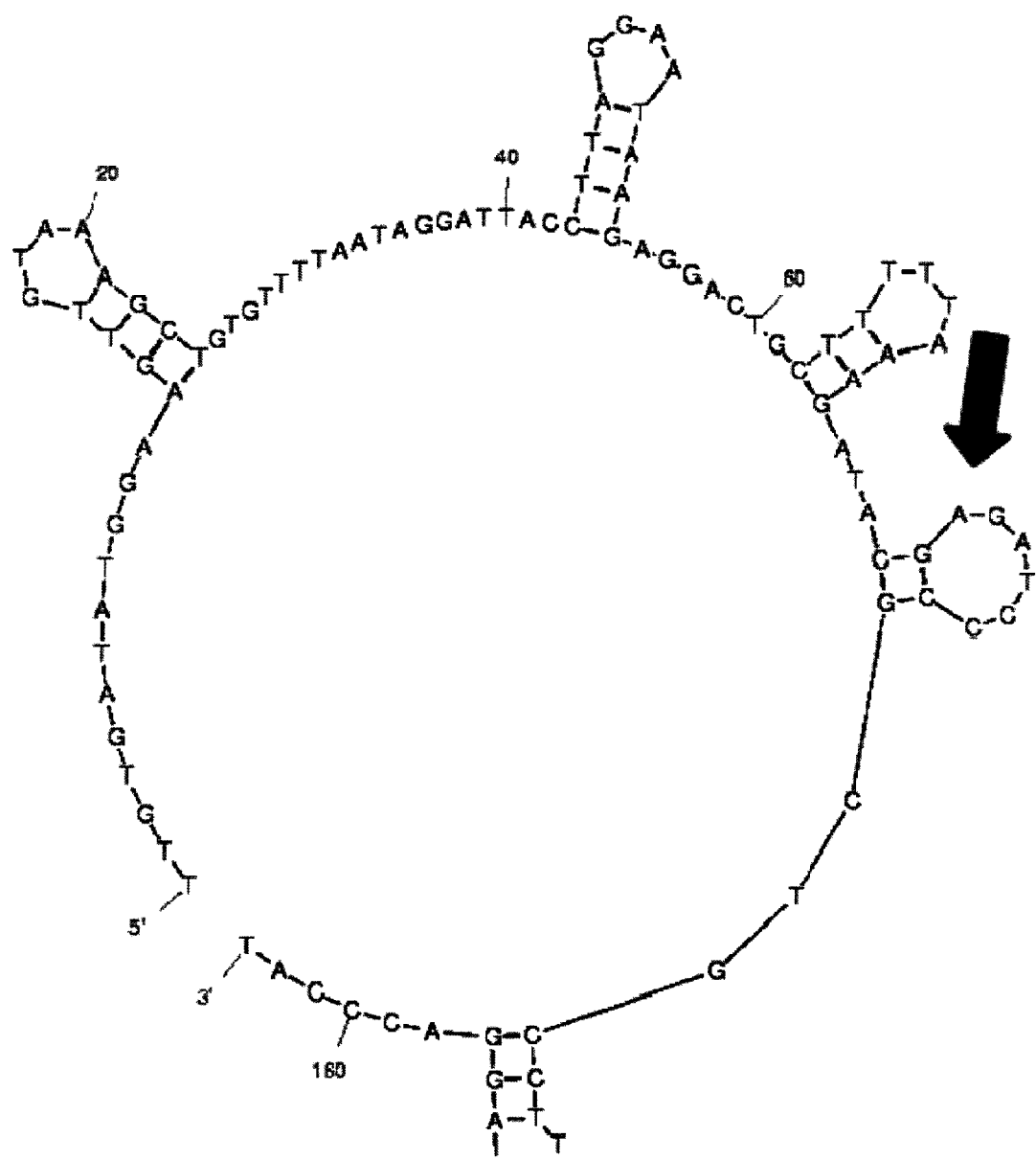
FIG. 3. Predicted secondary structure of the FADD amplicon. The red arrows point to the start and end points of the MNAzyme sensor arms. The point where the partzyme A meets partzyme B is located at the lower stem right beneath the big loop.
Figure 3B:
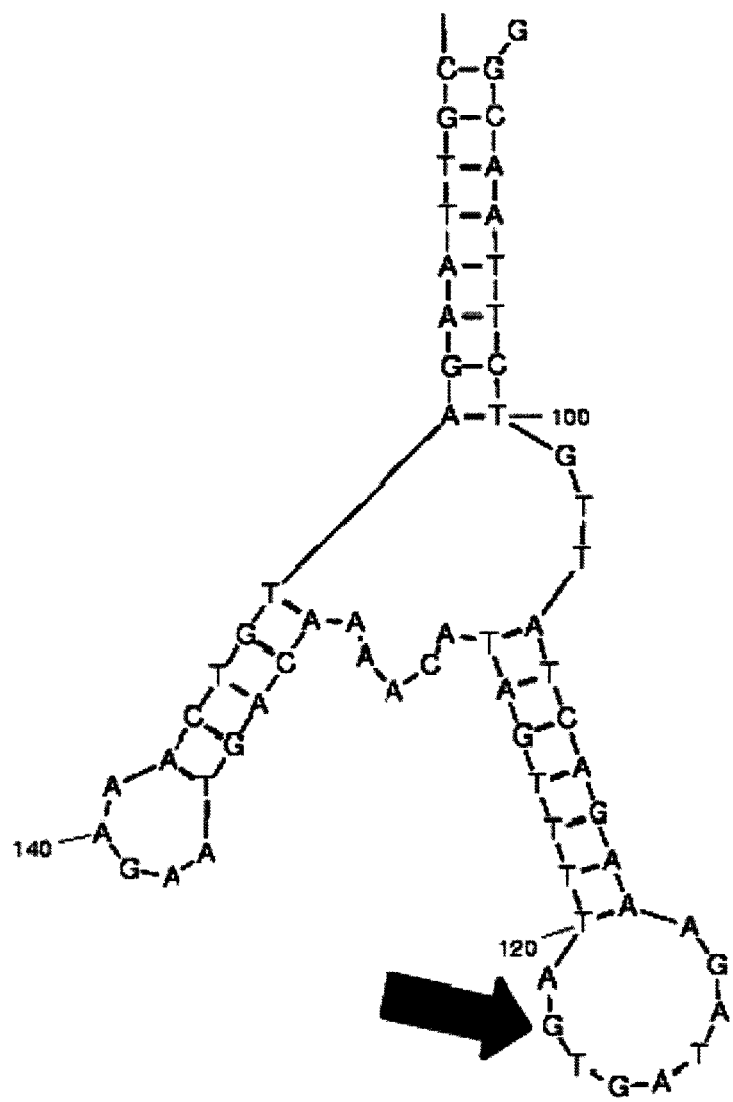
Figure 4A:
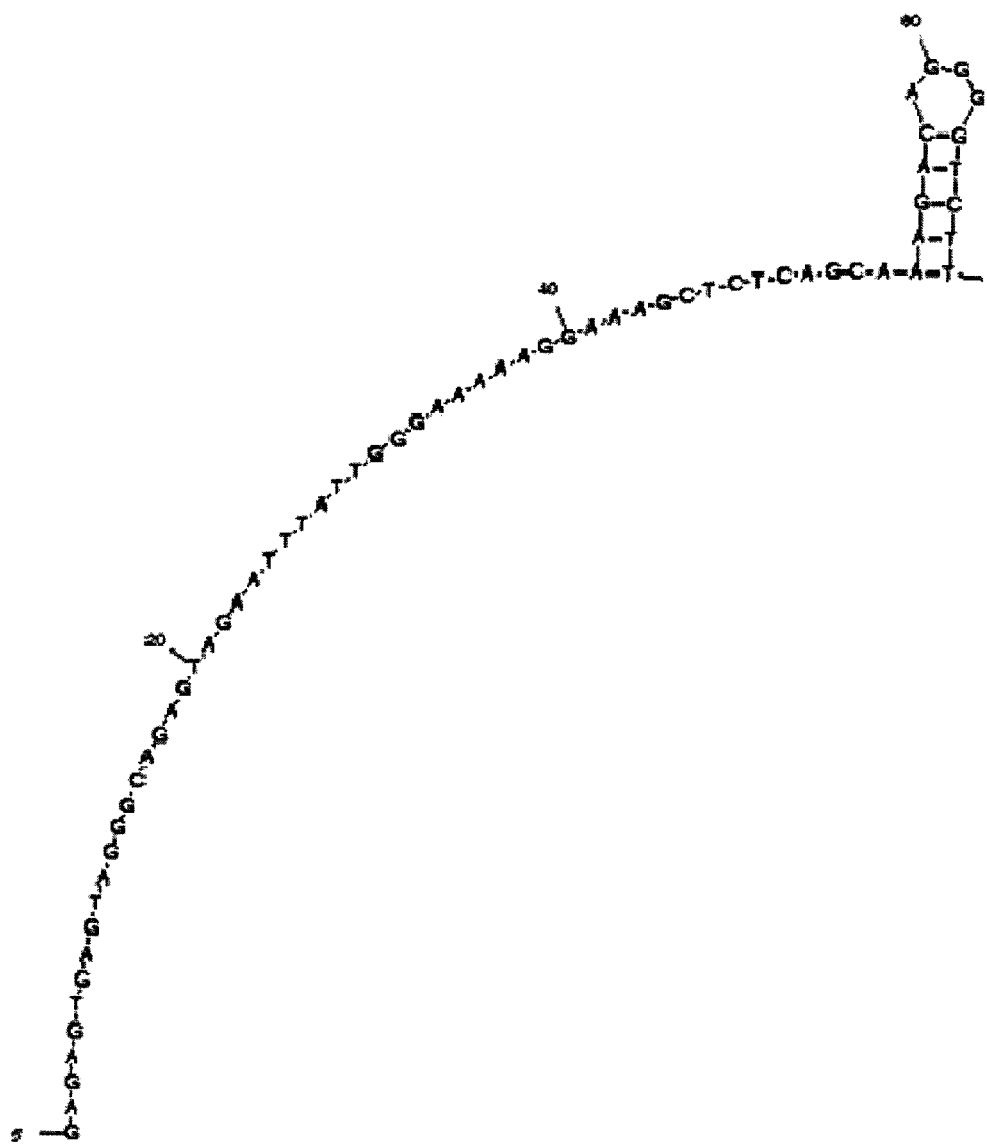
FIG. 4. Predicted secondary structure of the GSTM amplicon. The red arrows point to the start and end points of the MNAzyme sensor arms. The point where the partzyme A meets partzyme B is located in the only stem-loop between the two red-arrows. This picture shows the third design for the MNAzymes on the same amplicon that has been proven to work well in real-time PCR.
Figure 4B:
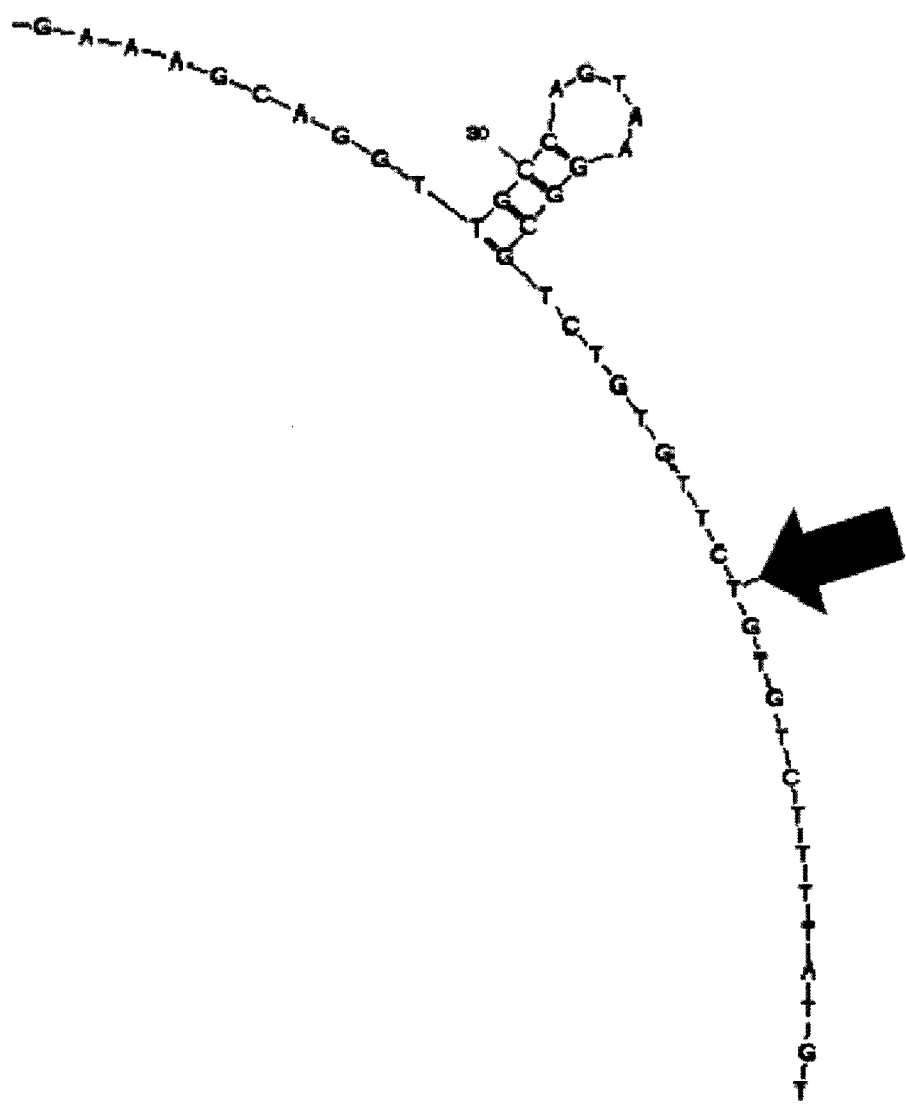
Figure 4C:
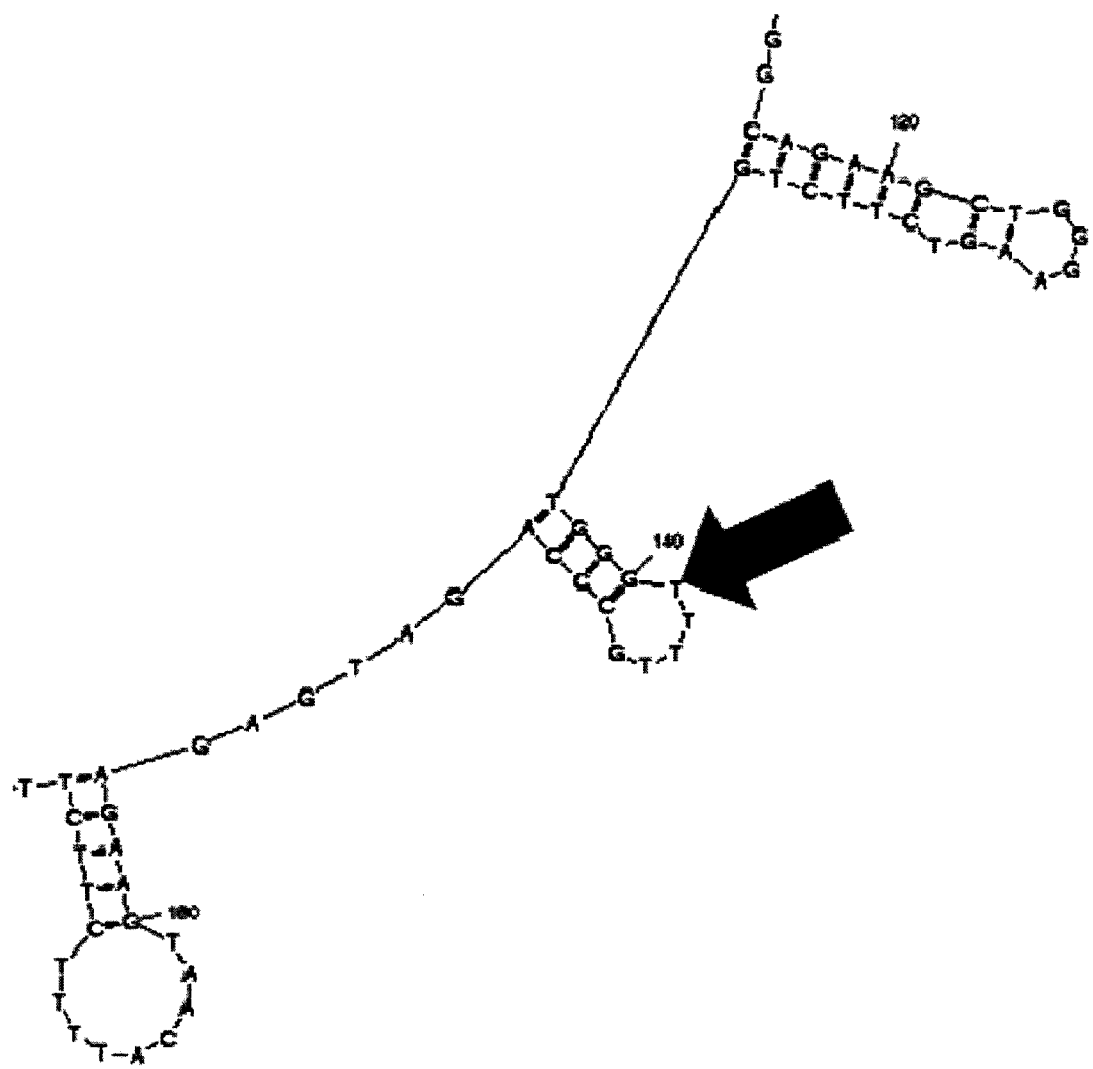
Figure 4D:
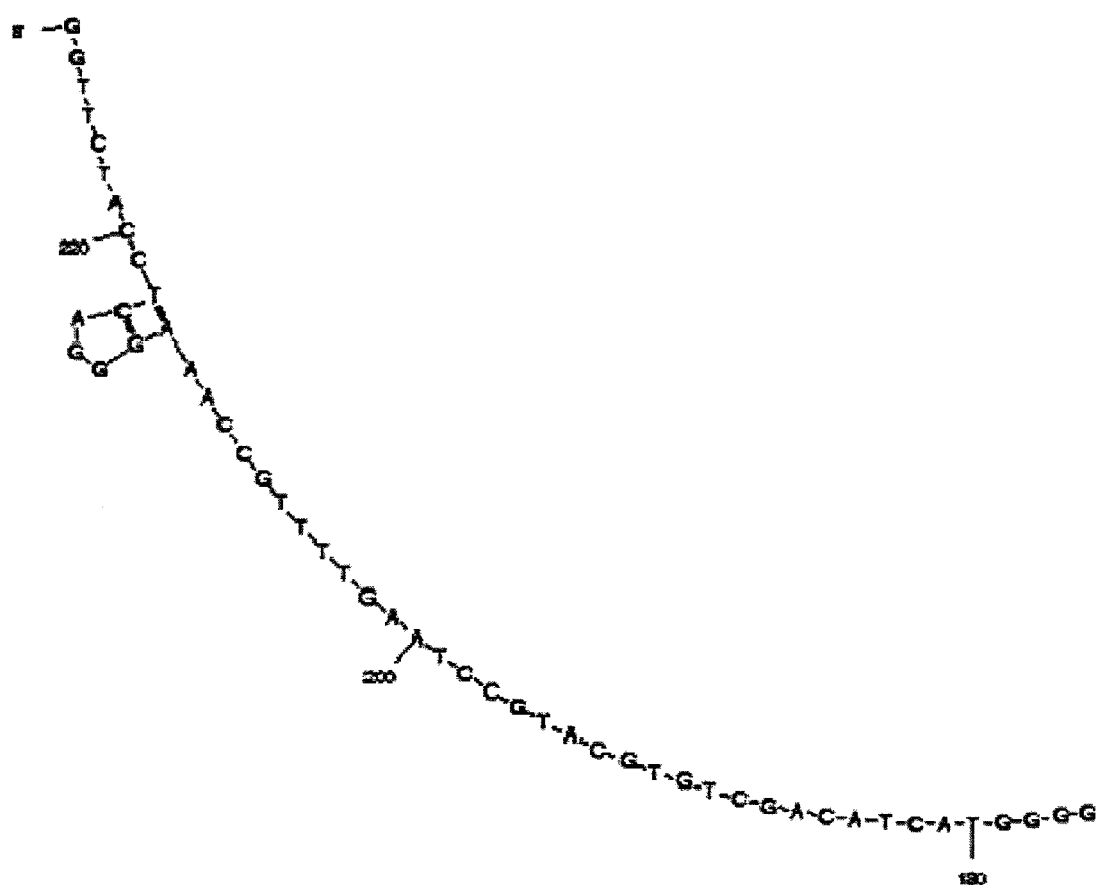
Figure 8B:
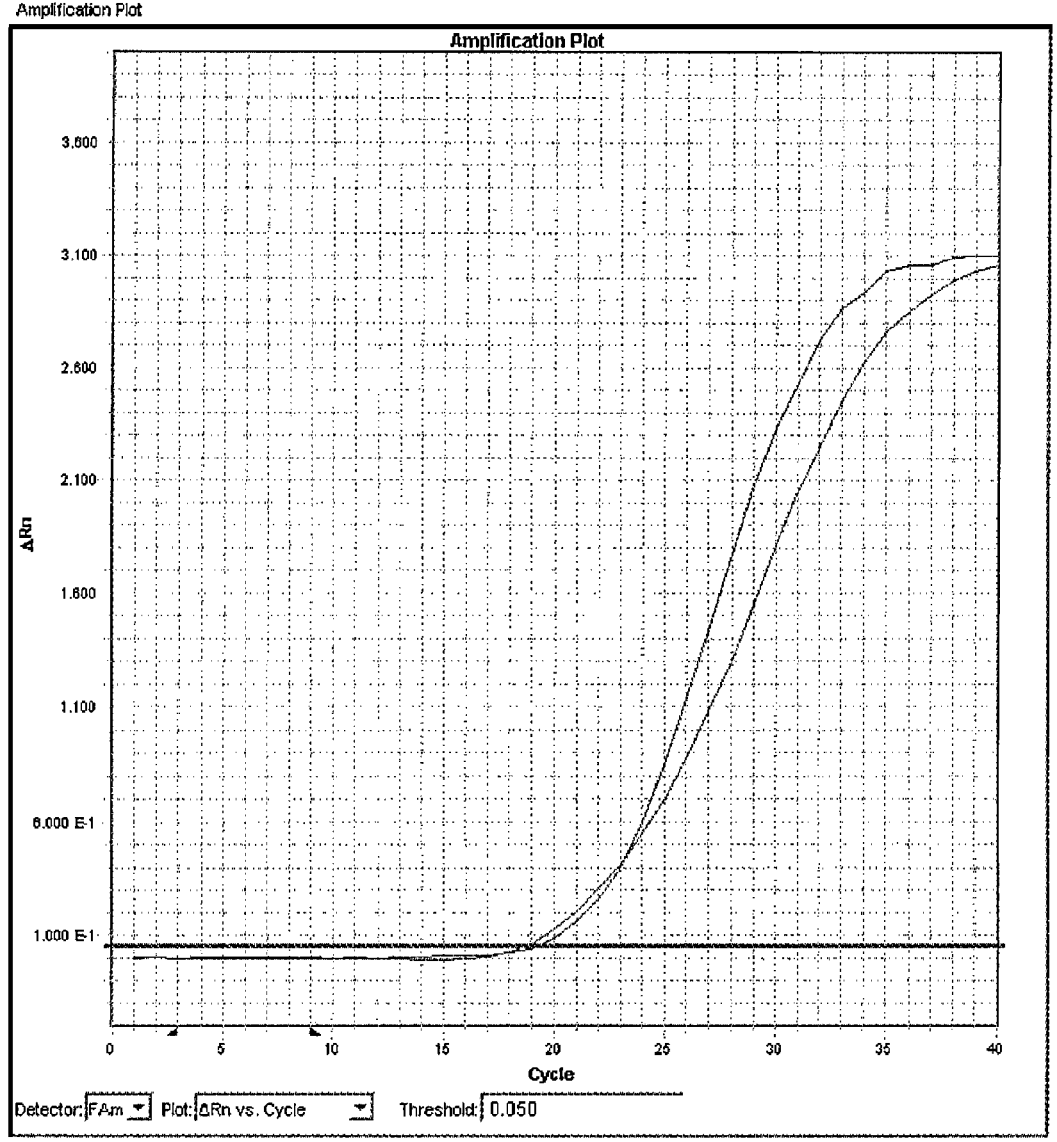
FIG. 8: Gene BIRC4, BAG1, and BIRC3 (Gene list 1) shown in singleplex and duplex under the same assay conditions except for varying Taq units and sources. Duplex performance rescued in 5 U of QIAGEN Taq.
Figure 8C:
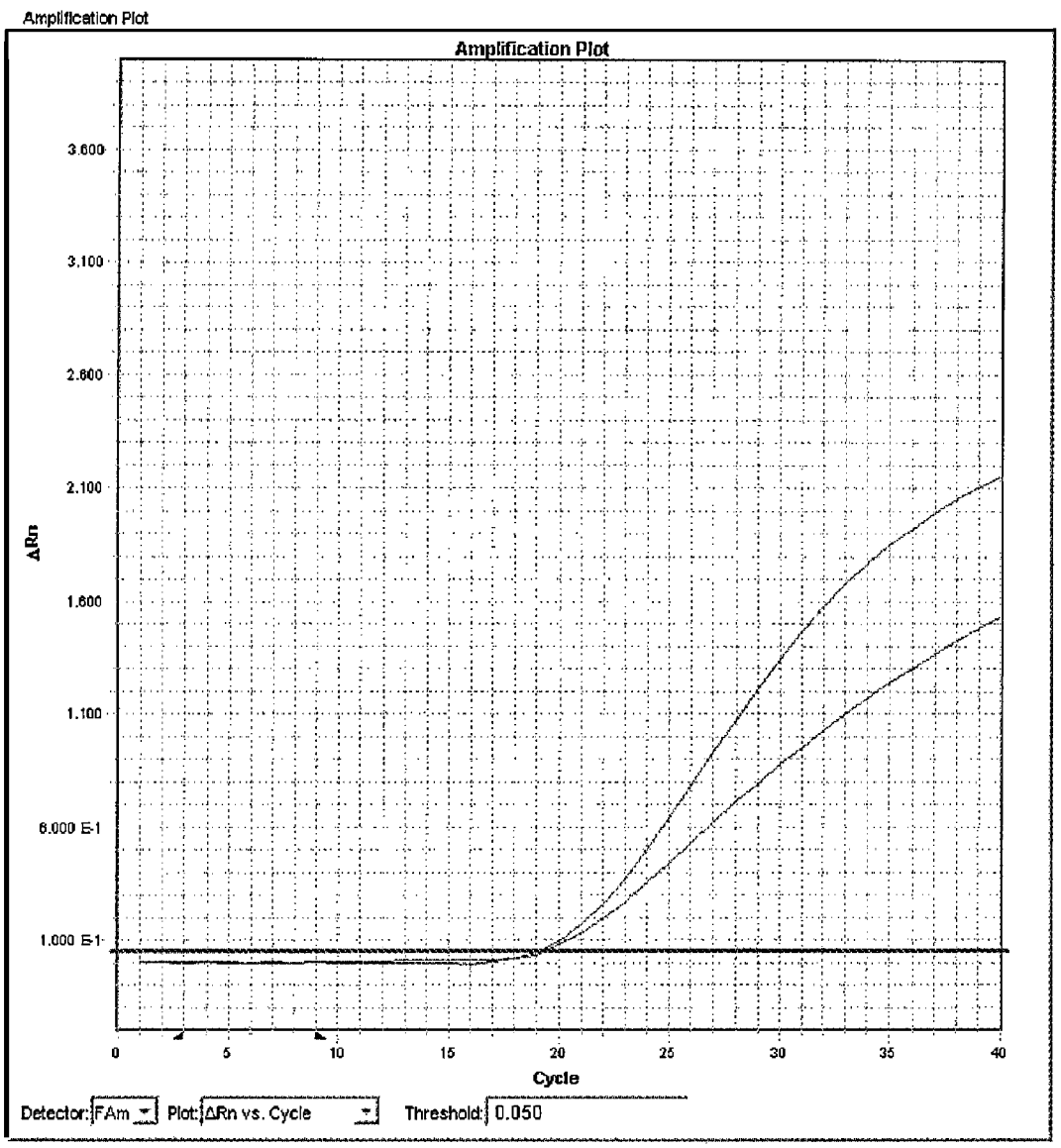
Figure 8D:
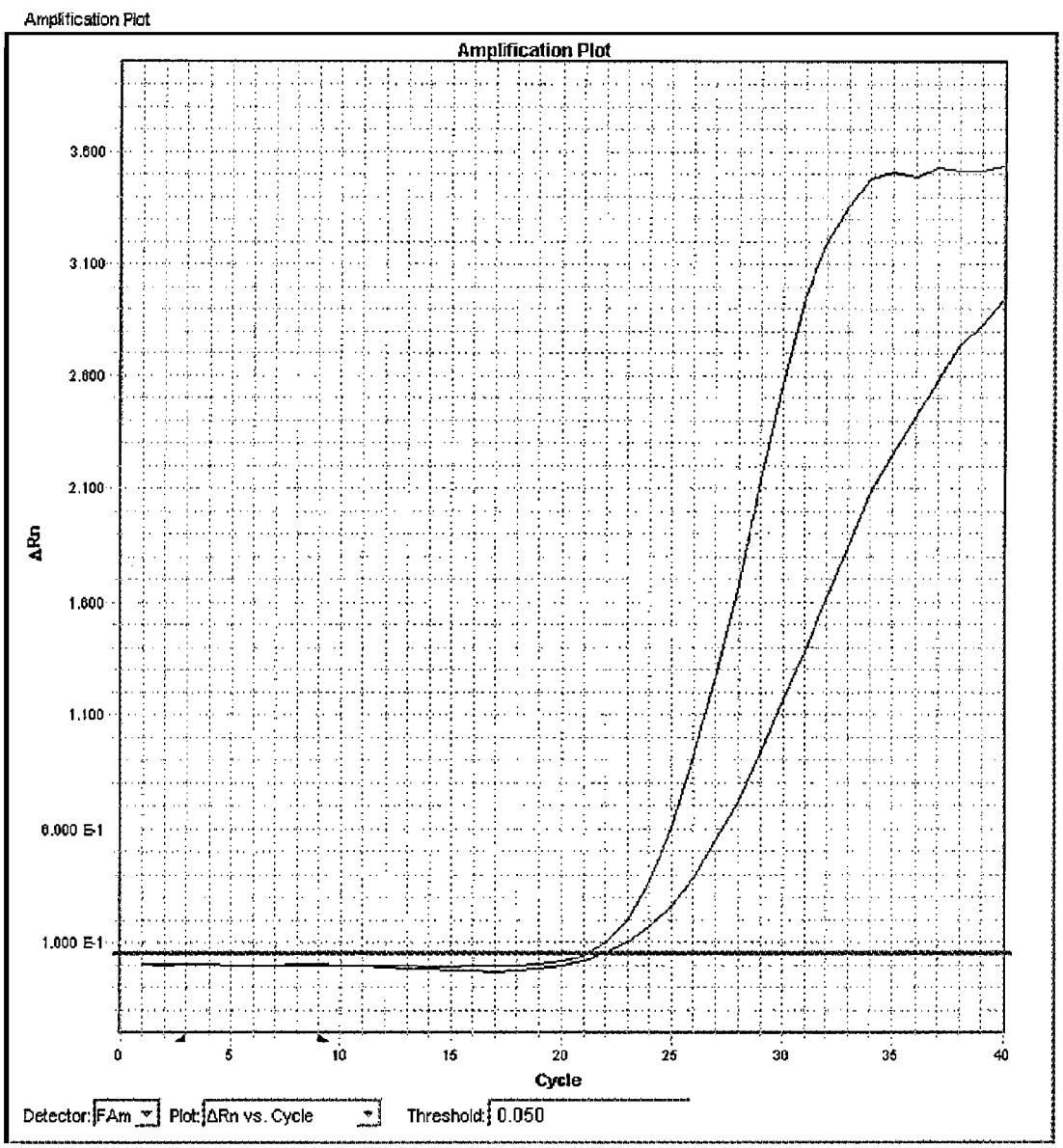
Figure 8E:
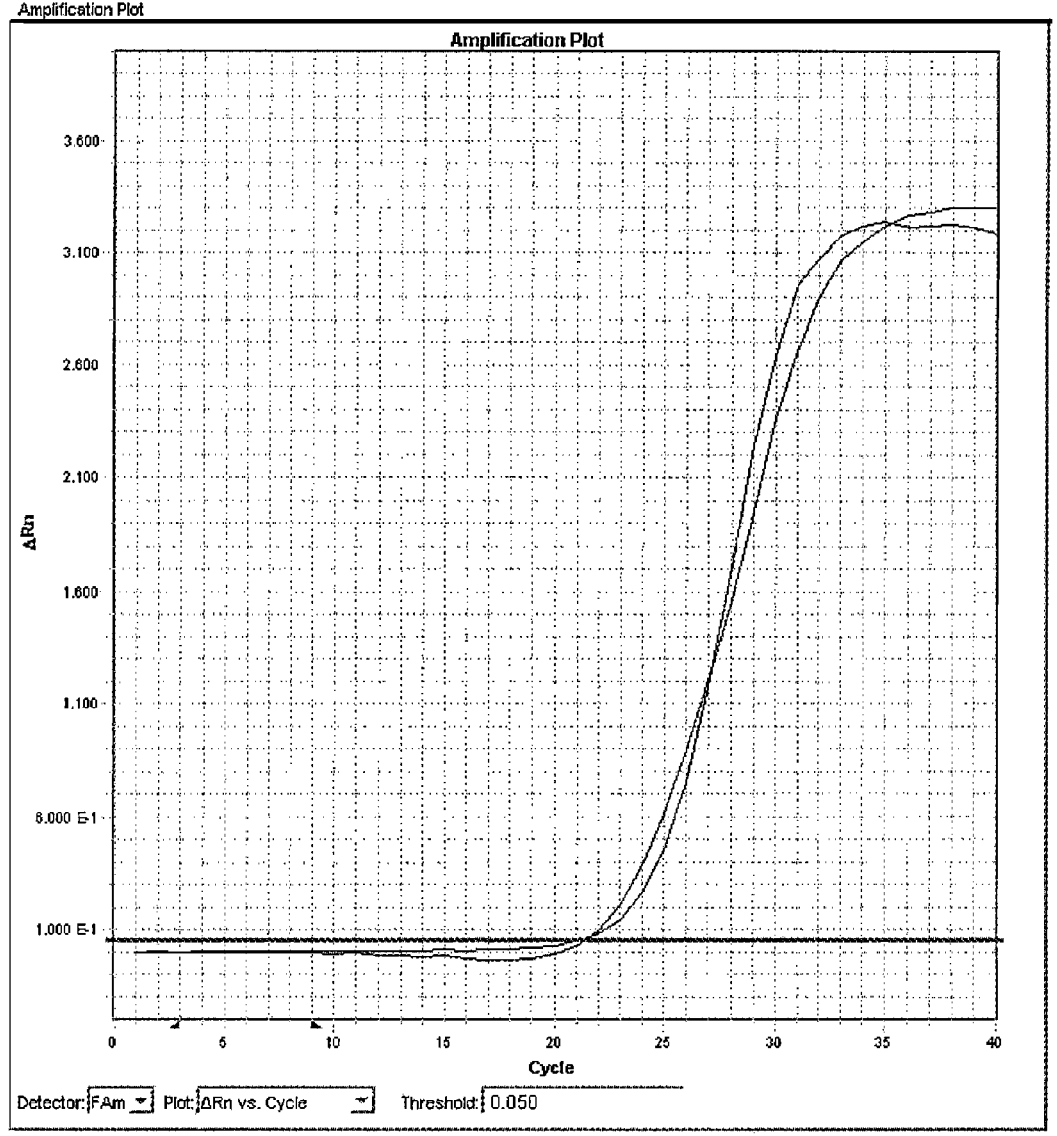
Figure 8F:
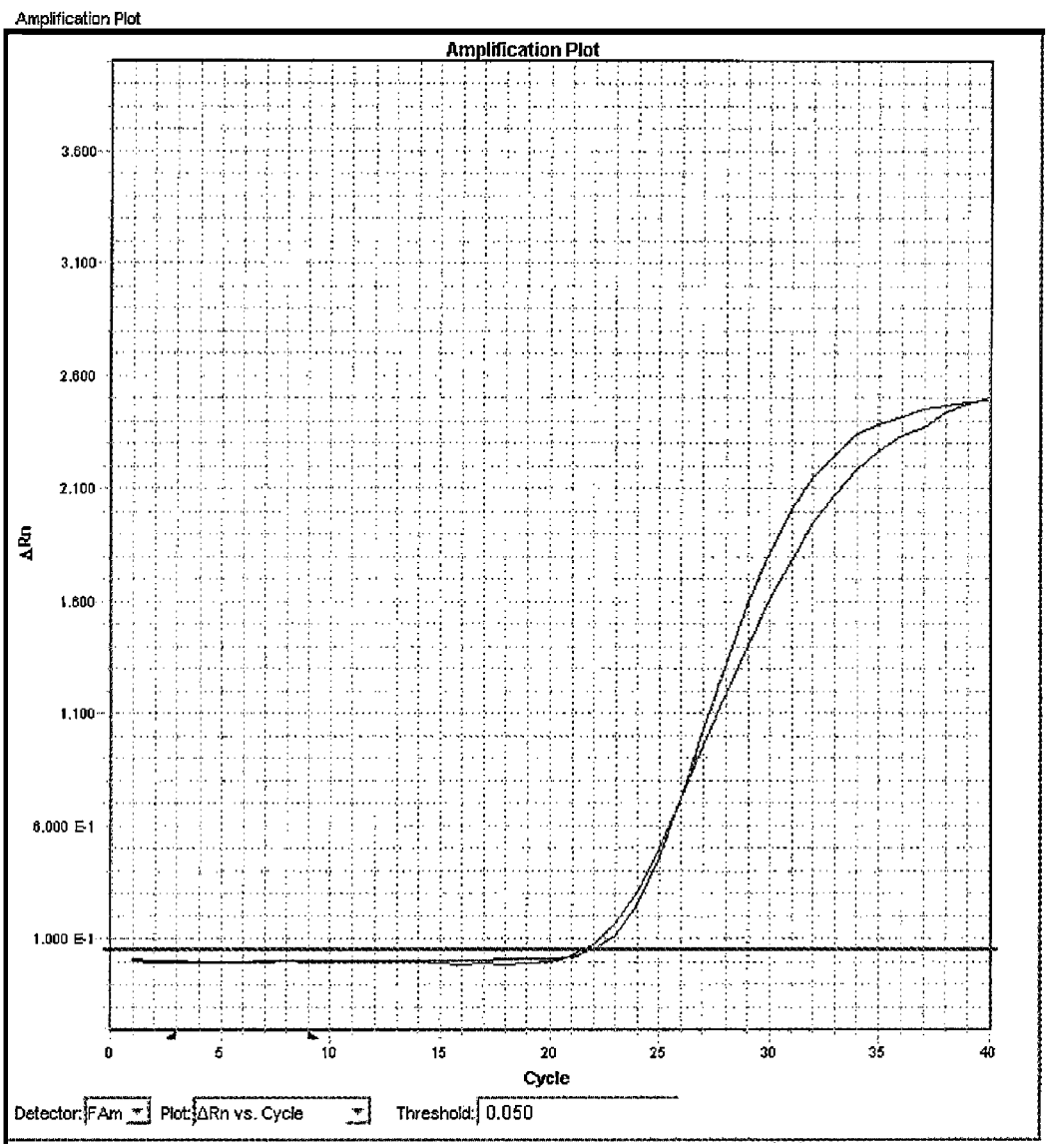
Figure 8G:
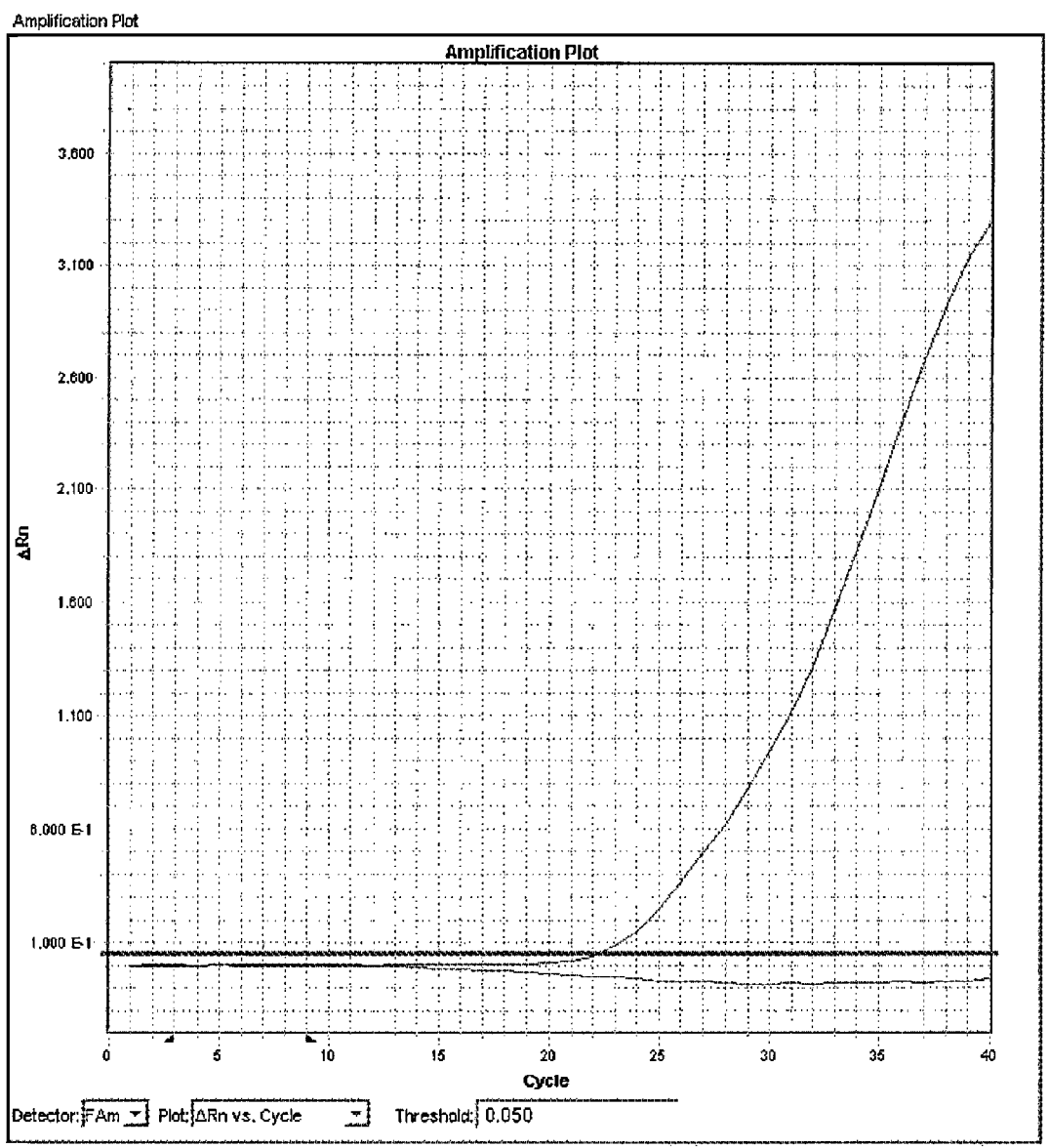
Figure 8H:
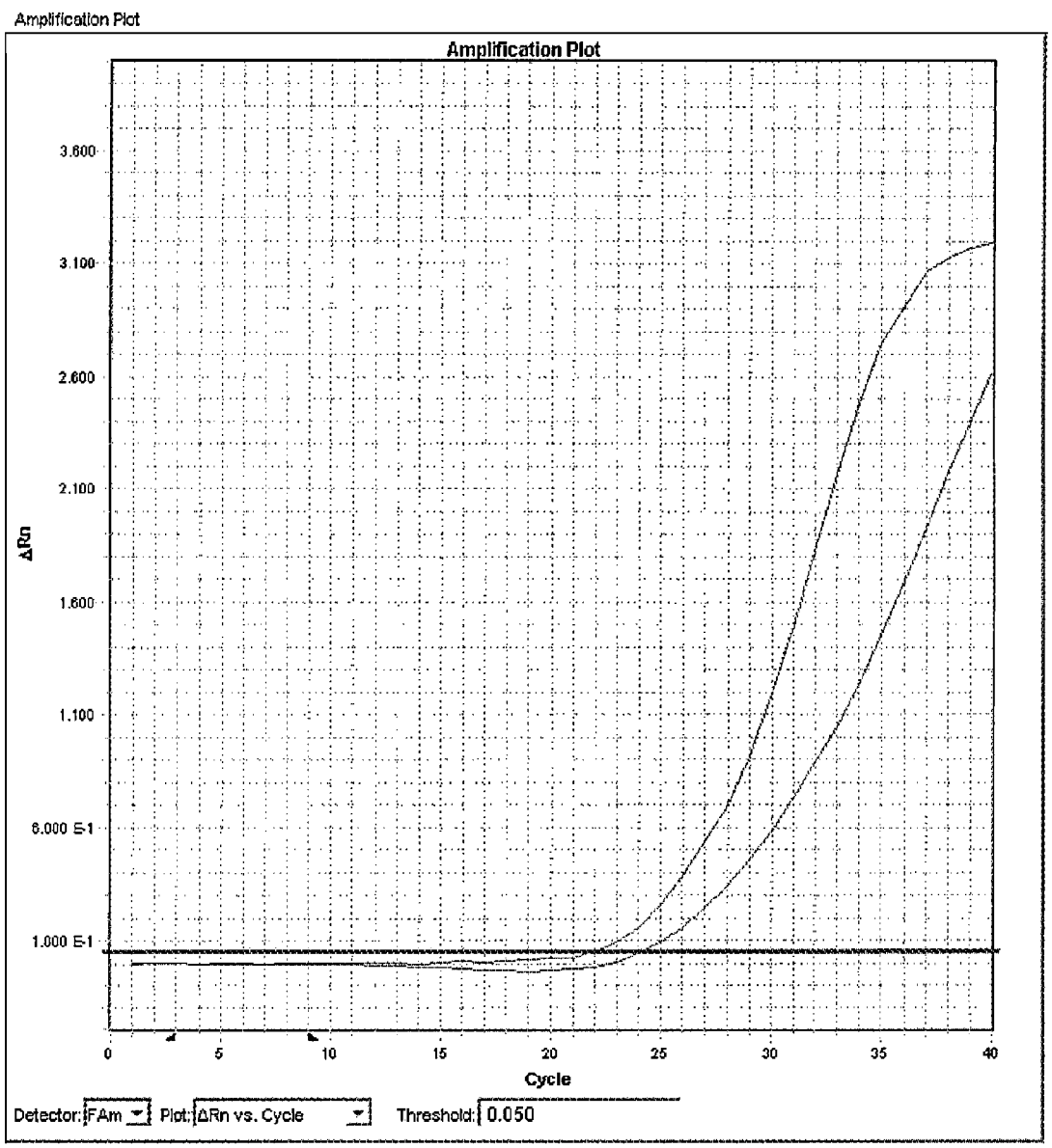
Figure 8I:
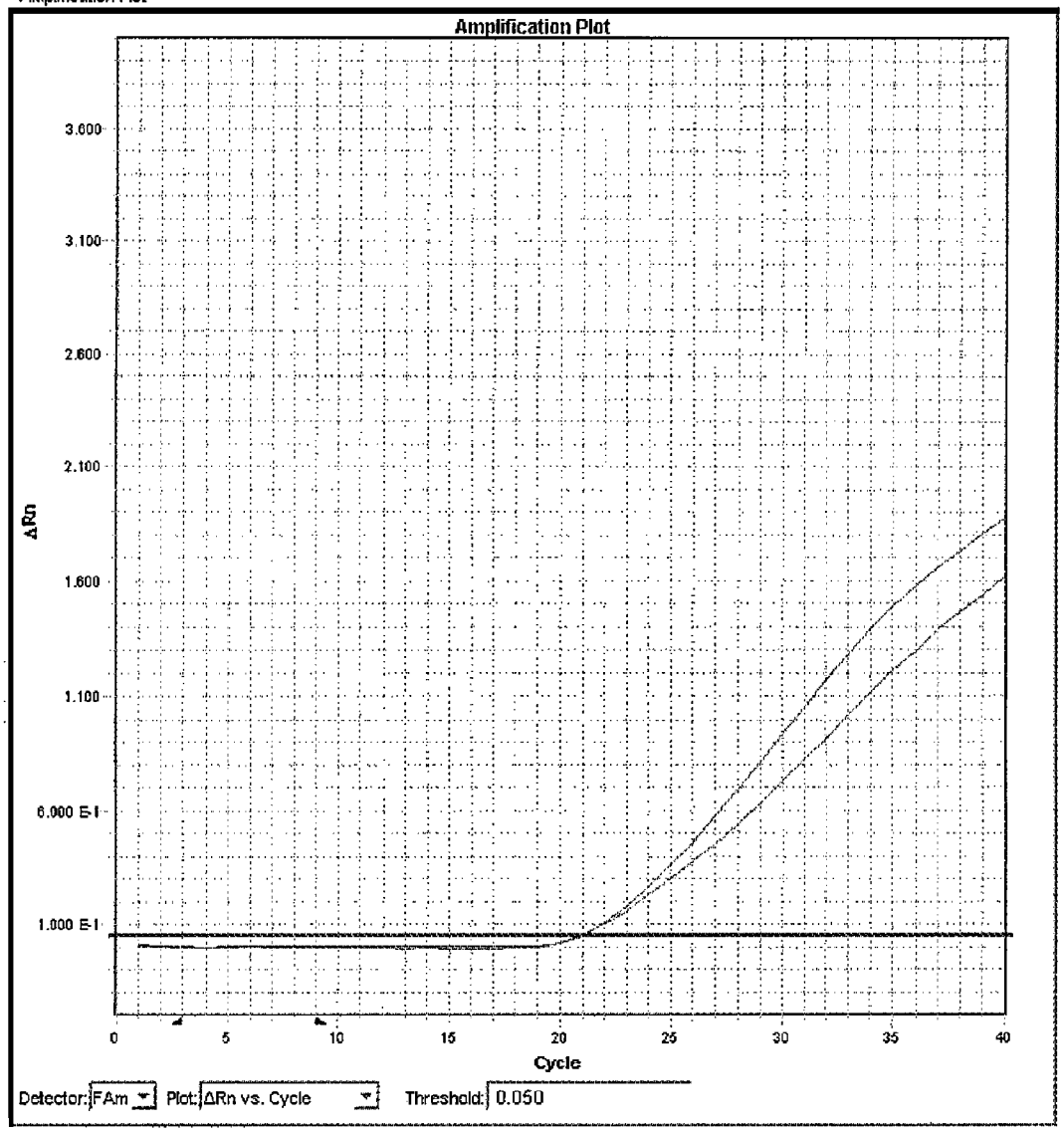

Applicants undertook extensive summarization and classification of results obtained using different MNAzyme designs to determine whether the success rate could be improved, preferably to at least 85%. The goal of this analysis was to identify factors predictive of successful MNAzyme detection of real-time PCR products. The analysis showed that potential secondary structures in the template region need not be avoided. For example, DNAJB4 (FIG. 2) and GSTM (FIG. 4) succeed with the MNAzyme junctions located within a stem-loop region. FADD (FIG. 3) has even more complicated predicted secondary structures that run through by the MNAzyme, also was successful. In these figures, dG is the calculated energy (by the mFOLD program) for the secondary structure shown in the picture.

The prediction of secondary structure of single-stranded mRNA or DNA mentioned in this example was predicted by the free mfold & UNAFold software (Markham, N. R. & Zuker, M. (2005) DINAMelt web server for nucleic acid melting prediction. Nucleic Acids Res., 33, W577-W581; Markham, N. R. & Zuker, M. (2008) UNAFold: software for nucleic acid folding and hybridization. In Keith, J. M., editor, Bioinformatics, Volume II. Structure, Function and Applications, number 453 in Methods in Molecular Biology, chapter 1, pages 3-31. Humana Press, Totowa, N.J. ISBN 978-1-60327-428-9; M. Zuker, D. H. Mathews & D. H. Turner Algorithms and Thermodynamics for RNA Secondary Structure Prediction: A Practical Guide. In RNA Biochemistry and Biotechnology, J. Barciszewski & B. F. C. Clark, eds., NATO ASI Series, Kluwer Academic Publishers, (1999); D. H. Mathews, J. Sabina, M. Zuker & D. H. Turner Expanded Sequence Dependence of Thermodynamic Parameters Provides Robust Prediction of RNA Secondary Structure. J. Mol. Biol. 288, 910-940 (1999)) both of which are freely available from the Rensselaer Polytechnic Institute website mfold.bioinfospi.edu.

These results suggest the potential secondary structures are un-reliable factors to consider in MNAzyme target selection. MNAzyme activity may not be harmed by selecting a stem-loop region when picking a MNAzyme target. However, adhering to this constraint more limits the PCR target selection, which will adversely affect the PCR design output rate and success rate. Consequently, using conventional methods the overall MNAzyme detection rate will be reduced, as PCR amplification is pre-required for MNAzyme activity. As illustrated in FIG. 1, the PCR failure rate was about 16% when targets were selected using conventional methods that avoid secondary structure (row GL1&2), whereas the PCR failure rate was reduced by over 4-fold to less than 4% (row GL3-5). Based on this conclusion, we adopted the target selection methodologies established in high through-put RT-PCR design (using the SYBR green I detection system).

We further considered the MNAzyme design. The conventional view was that two out of the three parts of the MNAzyme are un-changeable: the substrate recognition arm and the catalytic core, and the only part that can be modified is the sensor arm. However, we observed that the MNAzyme activity can vary greatly, which suggested there is space to improve. In addition to the general rules in sensor region selection such as uniqueness, no cross-hybridization to un-wanted region, no un-wanted secondary structure that adversely affect the direct binding between the sensor and the target, we considered the sensor arm junction. Our analysis identified a more optimal MNAzyme design. Particularly, we determined that the optimal junction for MNAzyme activity is G|C/G (FIGS. 6 and 7). These figures illustrate average relative MNAzyme activity for each combination of Partzyme A sensor last base and Partzyme B first base tested (parentheses indicate the numbers of MNAzymes tested containing each combination). Following this rule the partzyme sensor A ends at G, partzyme B sensor begins with C or G at the junction offers the greatest MNAzyme activity on average. We further evaluated whether the bases flanking these junctions could have any beneficial or detrimental effect. Somewhat reduced enzyme activity was observed for the GG|GA junction (the Partzyme A sensor region ends with GG and partzyme sensor B begins with GA) (FIG. 7). In this experiment, junctions following the G|C/G rule had average activity of 9.93, whereas junctions GG|GA had significantly reduced average activity of 7.61. Though the GG|GA junction gave significantly reduced activity relative to other G|C/G junctions, they are nonetheless still considered preferable over junctions that do not follow the G|C/G rule. The rule of preferring partzyme endpoints that contain a G|C/G junction but preferably are not GG|GA is referred to as the partzyme endpoint rule.

Example 3

This example provides illustrative pseudo code for implementing the partzyme end point rule described in the latter portion of Example 2.

For i=5'primer_length + 20; i<amplicon_size – 3'primer_length −20; i ++
    If ith base !~ /G$/ OR (i+1)th base !~ /^(C|G)/
        Search for next end point;
        * optional:
        If (i−1 to i+2)th base eq GGGA
            Search for next end point;
        Else further evaluate the two partzymes (separated at the ith base)

* Optional means we may enforce the rule in the first round design and remove the rule in a later round design if the first round design is unsuccessful. For example, in a large-scale design (with many genes), in the first round design some genes may have no design matching these constraints, in which case additional round design with gradually loosed rules can improve the output rate (proportion of genes with design).

Example 4

MNAzyme Design

In addition to the end-point rule algorithm described in Example 3, we also adopted the following design guidelines. Those of skill in the art will appreciate that these guidelines are not necessarily strict requirements and that acceptable MNAzyme activity can be obtained without adhering to every guideline. For example, for a given MNAzyme design problem it may be unnecessary to or impossible to select target sequences that satisfy every guideline, and that easing of some of these guidelines may still yield acceptable MNAzyme designs. Moreover, candidate designs may be routinely constructed and tested for activity, optionally using a high-throughput format, to identify those designs that are acceptable for a given circumstance. These additional design guidelines are as follows:

Partzyme A and partzyme B sensor arm TM has no difference bigger than 5 degrees C.;

The six bases around the partzyme junction does not form a palindrome structure;

Our experimental evidence (FIG. 5 and FIG. 6) indicated that further benefit can be achieved by avoiding potential base matches between the partzyme core and positions in the target adjacent to the partzyme sensor arm binding region. When partzyme B sensor arm target start with T and partzyme A sensor arm target end with A, a lowered MNAzyme activity is observed. Based on these observations, we determined that a single base match between the core of one partzyme and the sensor of the other partzyme can severely interfere with MNAzyme activity. Thus, we adopted the further constraint that no potential matching bases should be present within the first three bases of the sensor arm and the core, e.g., when the partzyme A catalytic core is SEQ ID NO: 3 (acaacga) and the partzyme B catalytic core is SEQ ID NO: 12 (ggctagct), the first three bases of the partzyme B sensor region should not be T, G, and T respectively, and the final three bases of the partzyme A sensor region should not be C, G, and A, respectively (note that in this example the 5' end of the partzyme A catalytic core is adjacent to its sensor arm, and the 3' end of the partzyme B catalytic core is adjacent to its sensor arm). Avoidance of potentially matching bases within regions longer than three bases may confer further benefit and can be readily determined through routine experimentation. Moreover, in some instances avoidance of potentially matching bases within regions shorter than three bases (e.g., two bases, one base, or even no bases) may nonetheless give a satisfactory result for a given instance. Finally, the desirable length within which to avoid potentially matching bases may be independently determined for partzymes A and B.

Other general rules in primer/probe design are also observed in our MNAzyme design, these rules include: the partzyme melting temperature can be routinely optimized for a given application (too high or too low can reduce MNAzyme activity), and sequences can be chosen to avoid the unwanted binding between partzymes, between partzyme and amplicon, between probe and the amplicon. Any stretch of 5 bases (AAAAA/TTTTT/GGGGG/CCCCC) in the partzyme sensor region is also generally avoided.

Combinations of the aforementioned methodologies can provide synergistic benefits. For example, removing the constraint of avoiding predicted secondary structure within the target sequence improves the success rate of the amplification reaction. Further benefit can be achieved by selecting junction sequences that avoid interference between the sensor arm targets and partzyme core sequences, as described in the preceding paragraph. Yet further benefit can be achieved by selecting target and sensor sequences having the junction sequences described in Example 3. These methodologies may be used individually or in combinations to obtain improved MNAzyme

Example 5

This example describes modifications of conventional PCR assay methods which were used to improve success rates of real-time PCR with MNAzyme detection. In addition to the design methods described above, adjustments in the PCR chemistry also contributed to the overall success rate improvement from 62% to 90% (FIG. 1, GL3-5).

Changes in the adjusted chemistry (MMQ4) over the original chemistry (MMSA) include: 1) use of QIAGEN HotStar Taq Polymerase instead of SABiosciences Taq Polymerase; 2) increasing Taq amount from 2 Units to 5 Units per 25 microliter reaction; 3) changing the buffer pH from 7.9 to 8.2, and 4) eliminating a complex component (buffer C) of MMSA, except that the amount of Tween-20 contributed by buffer C was retained.

QIAGEN HotStar Taq Polymerase gave better PCR specificity, and increasing the Taq amount improved duplex assay performance (FIG. 8). Genes BIRC4, BAG1, and BIRC3 are shown in singleplex and duplex under the same assay conditions except for varying Taq units and sources. Duplex performance rescued in 5 U of QIAGEN Taq.

Conventional MNAzyme methods do not teach any relationship between assay pH and MNAzyme effectiveness or any desirability of modifying pH from whatever standard pH is utilized in the desired amplification reaction. However, additional improvement was obtained by modification of the assay pH. Results are summarized in FIG. 9. The genes in gene list 1 were each assayed by real-time PCR with MNAzyme detection assays performed at pH 7.4, 7.9, 8.2, and 8.4. Results were classified as "Bad" (inadequate signal), "Good" (adequate signal) and "Marginal" (between "Good" and "Bad") and percentages of genes in each classification are shown (due to round-off, not all columns total 100%). Compared to the original assay pH of 7.9, which gave 31% bad, 31% marginal, and 39% good, more optimal results were obtained at pH 8.2, which gave 33% bad, 12% marginal, and 55% good results. Lower pH and higher pH values tested gave fewer good results, specifically pH 7.4 gave 61% bad, 25% marginal, and 14% good results, and pH 8.4 gave 36% bad, 13% marginal, and 51% good results. It is expected that testing of additional pH values might give some further improvement. Moreover, it is expected that optimal pH could vary depending on the particular assay conditions (including catalytic core sequences, ions present, osmolarity, temperature, detergent, etc.) and can readily be determined for any given circumstance.

Figure 10A:
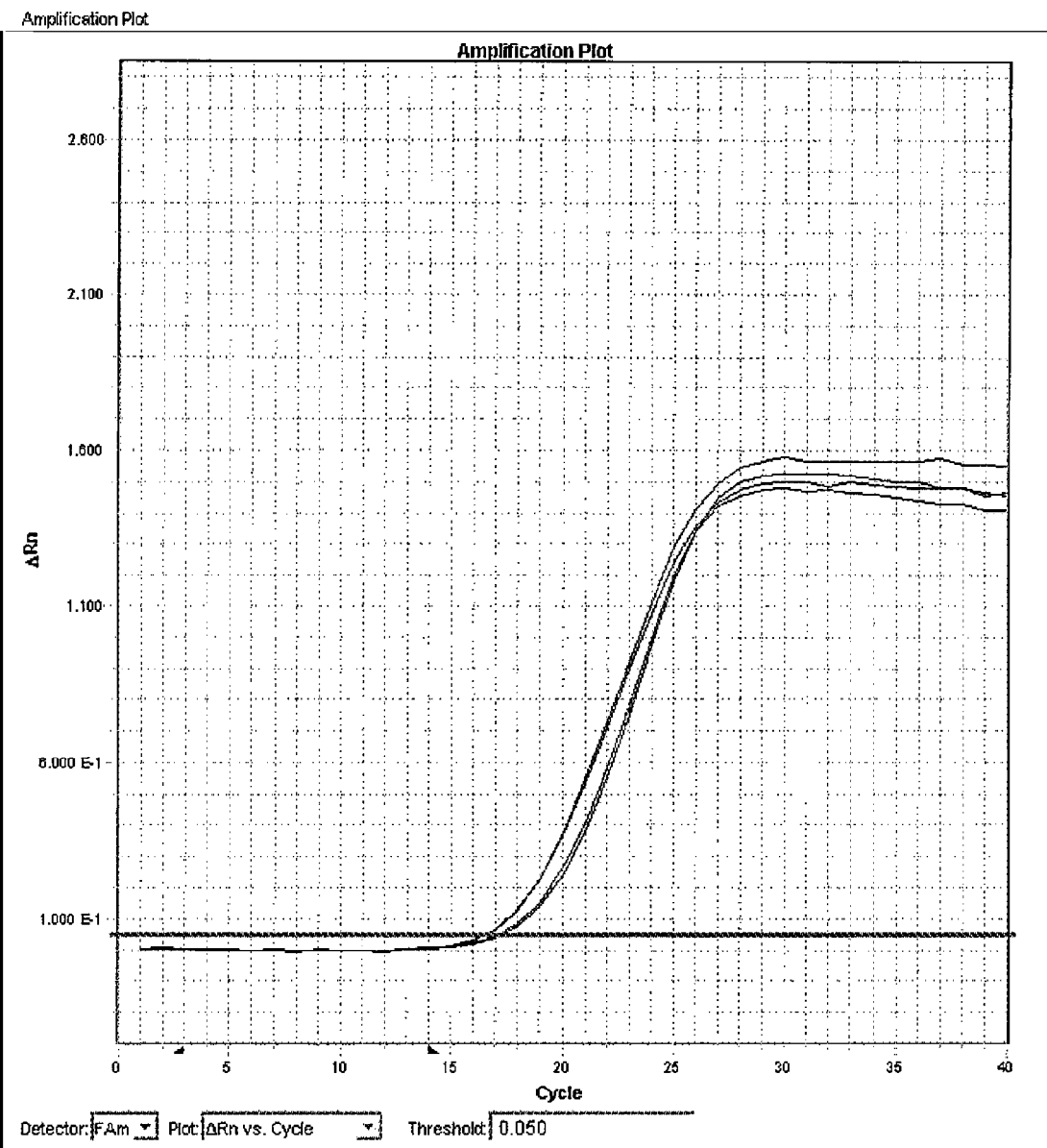
FIG. 10. Comparison of mastermix with buffer C and mastermix without buffer C but added Tween 20 in multiple genes.
Figure 10B:
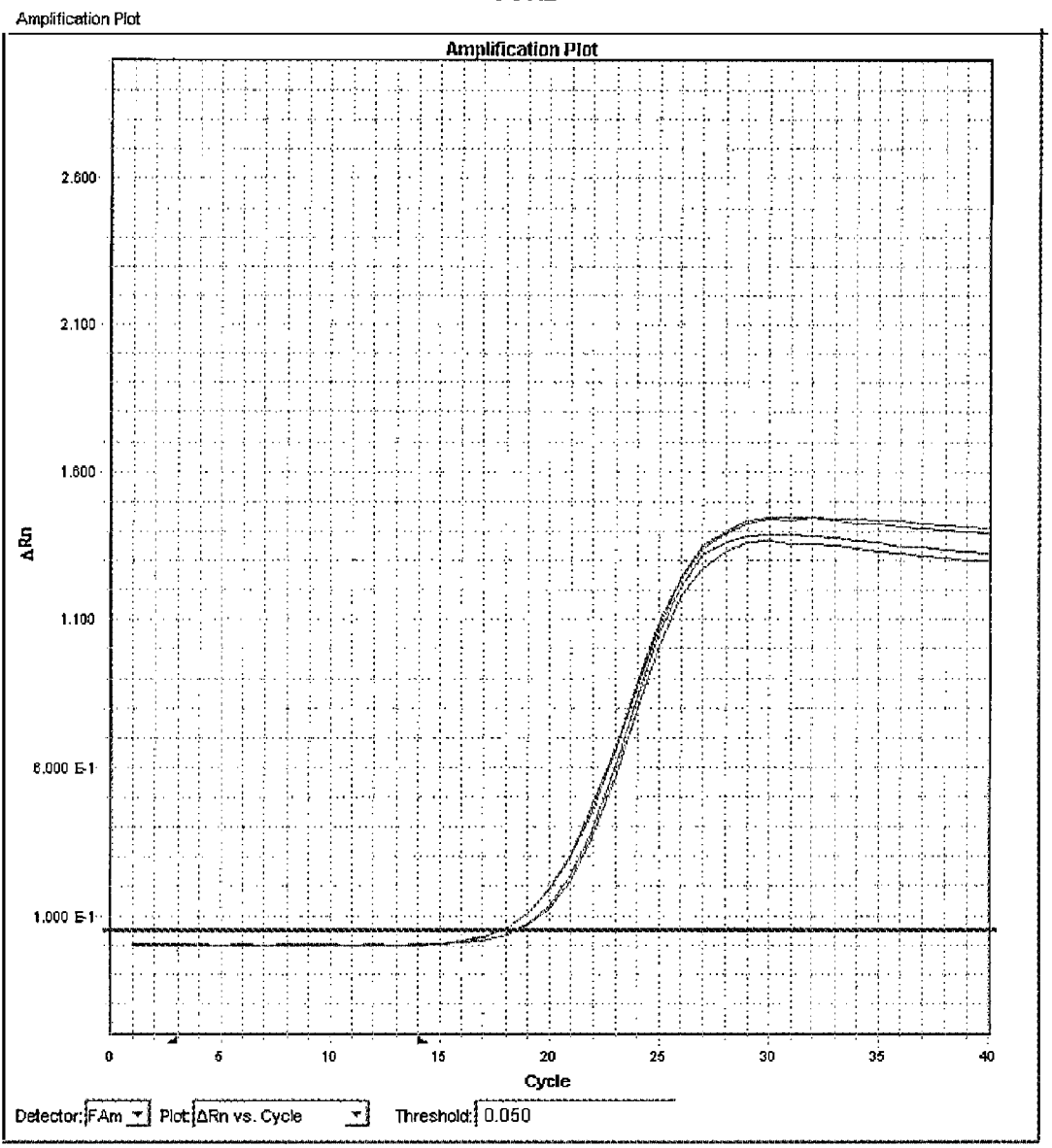
Figure 10C:
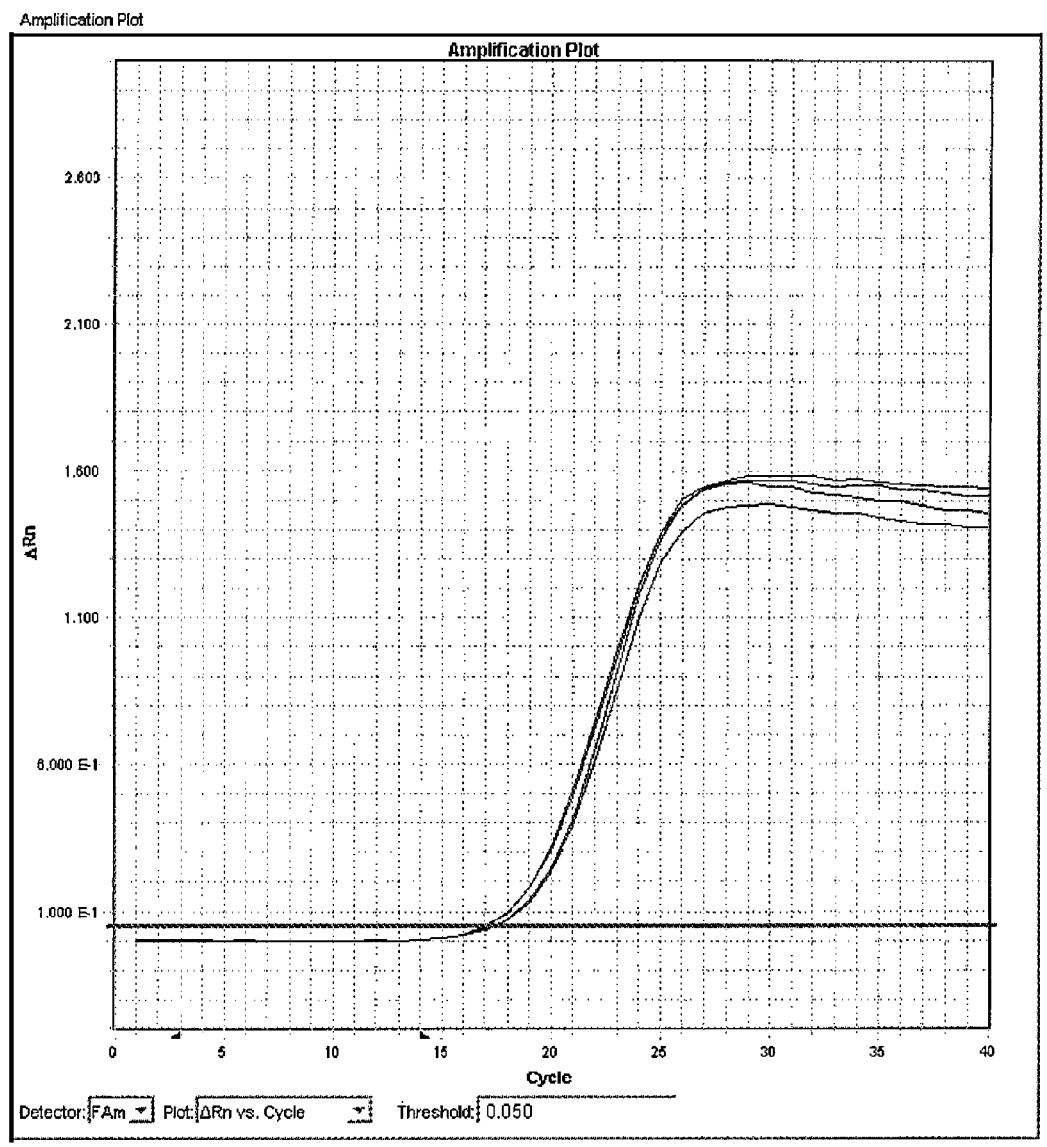
Figure 17A:
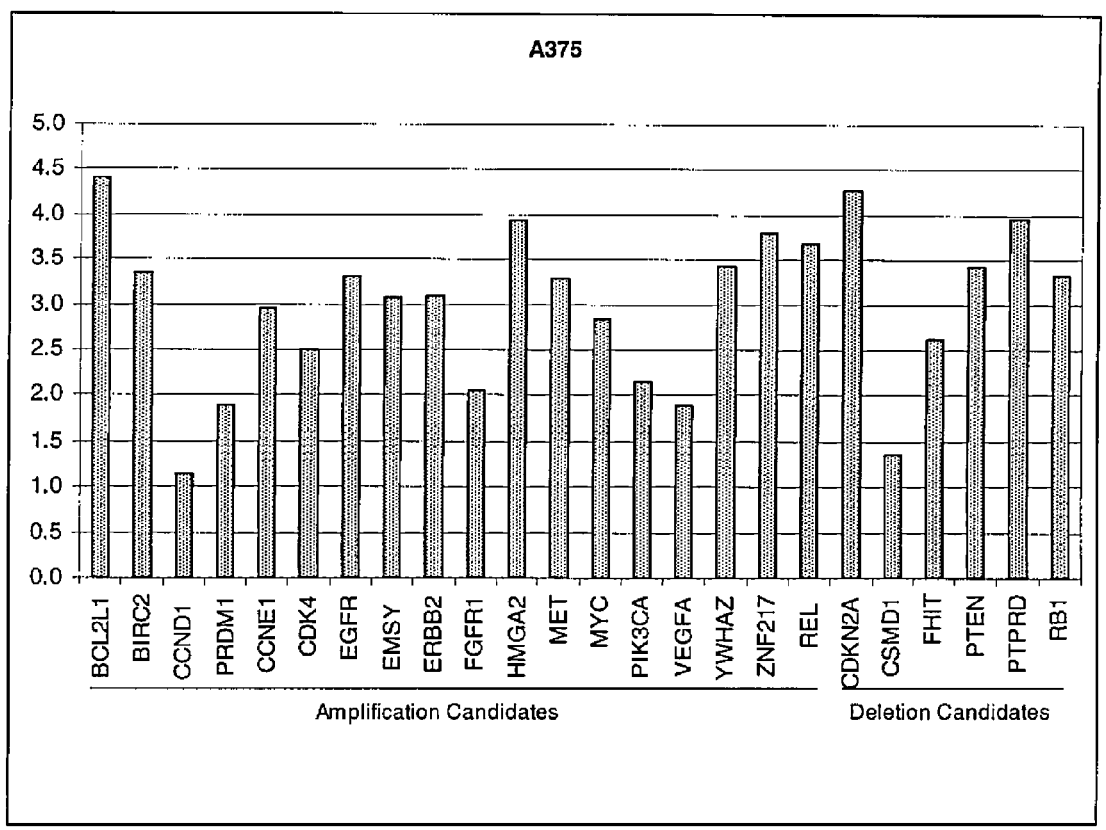
FIG. 17A-I shows the results of detecting copy number alteration profiles of 24 target genes for each of 9 different cancer cell lines as determined by an MNAzyme duplex assay. Detected amplified genes (having six or more copies) are indicated with a solid arrow, and deleted genes (having one or two deleted copies) are indicated with a dashed arrow.
Figure 17B:
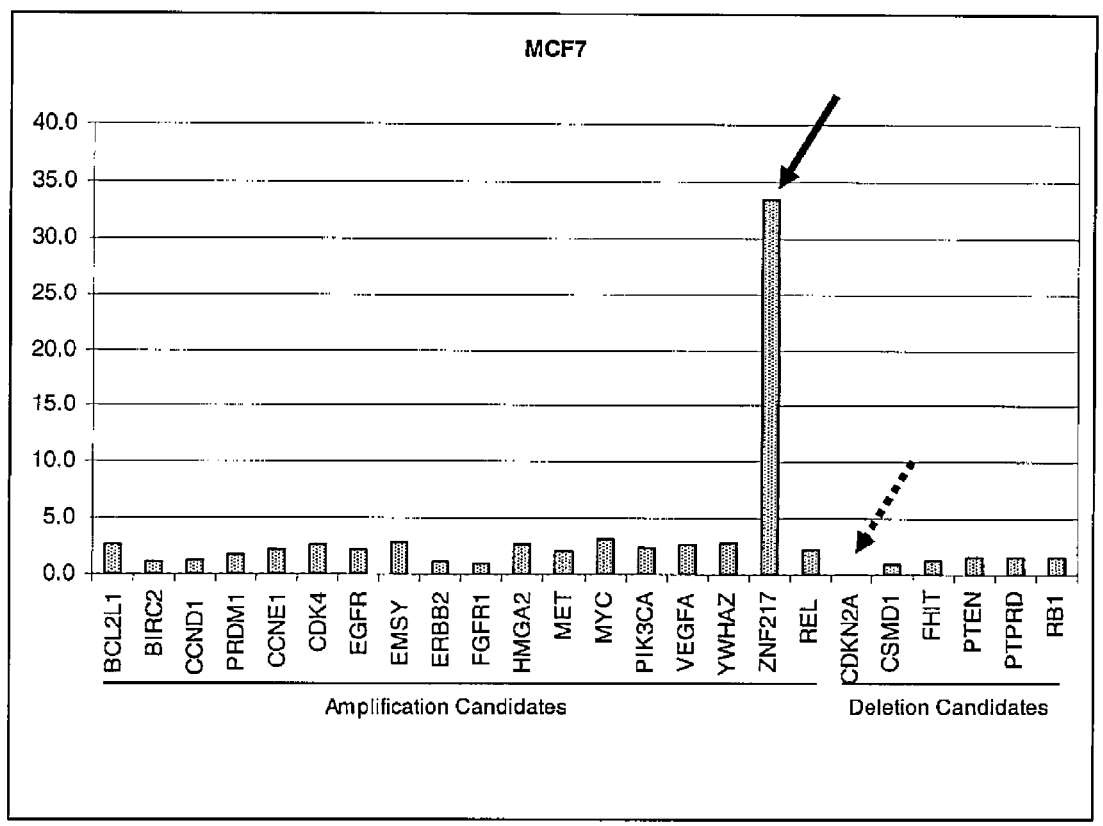
Figure 17C:
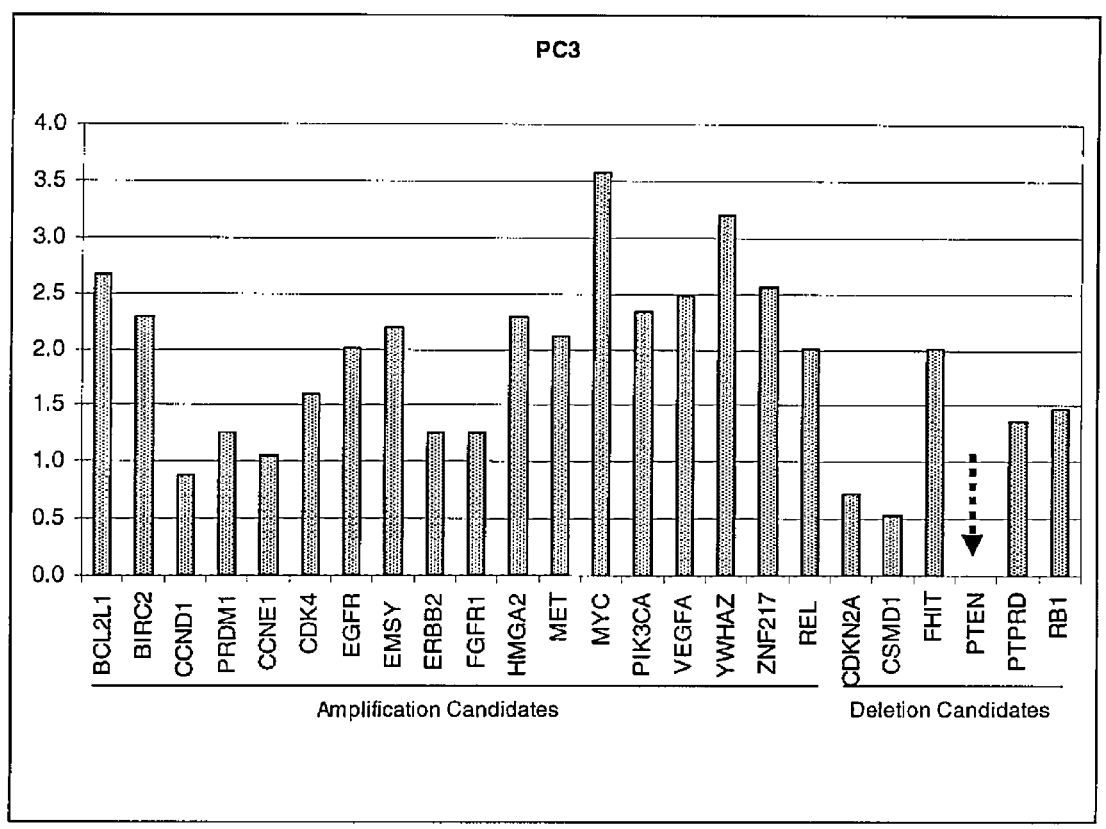
Figure 17D:
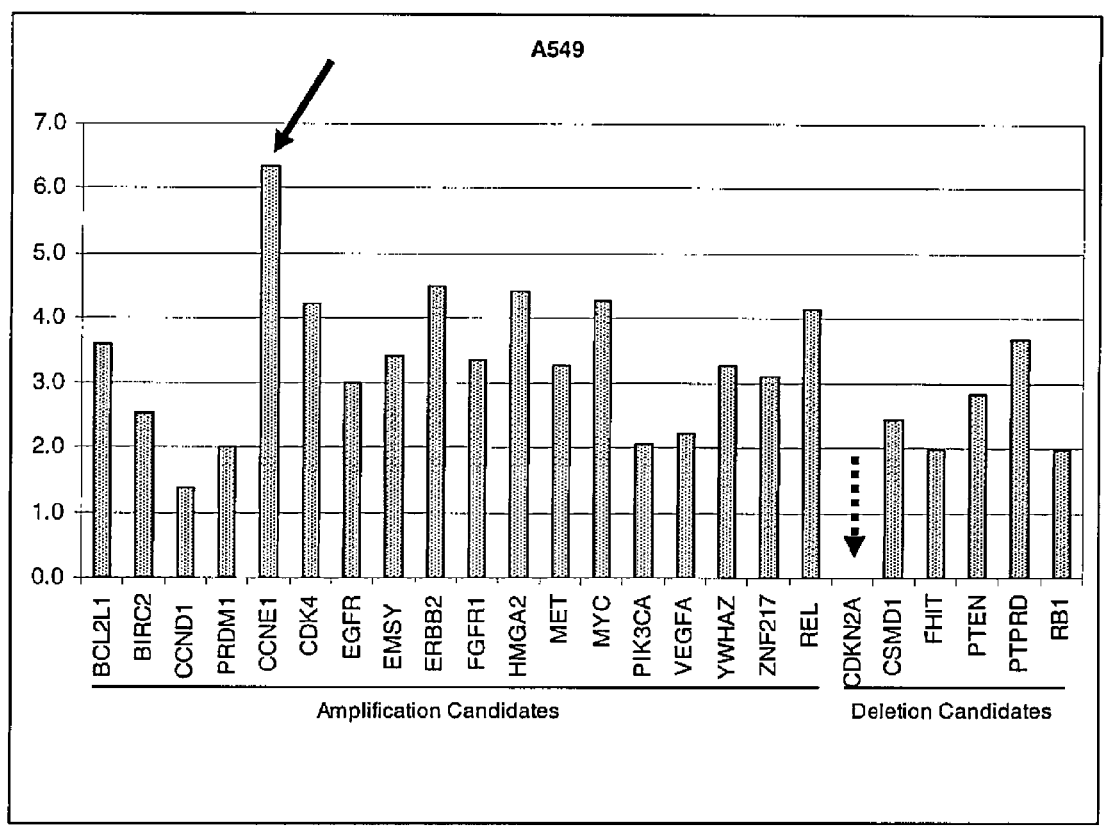
Figure 17E:
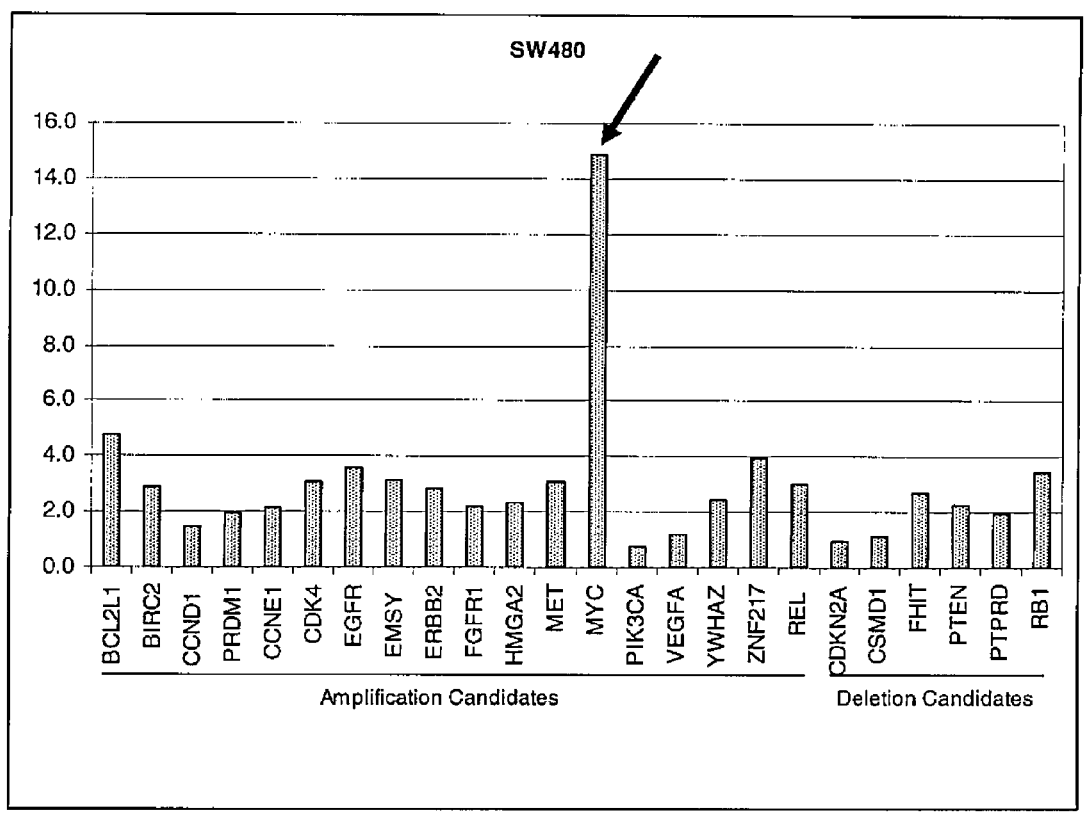
Figure 17F:
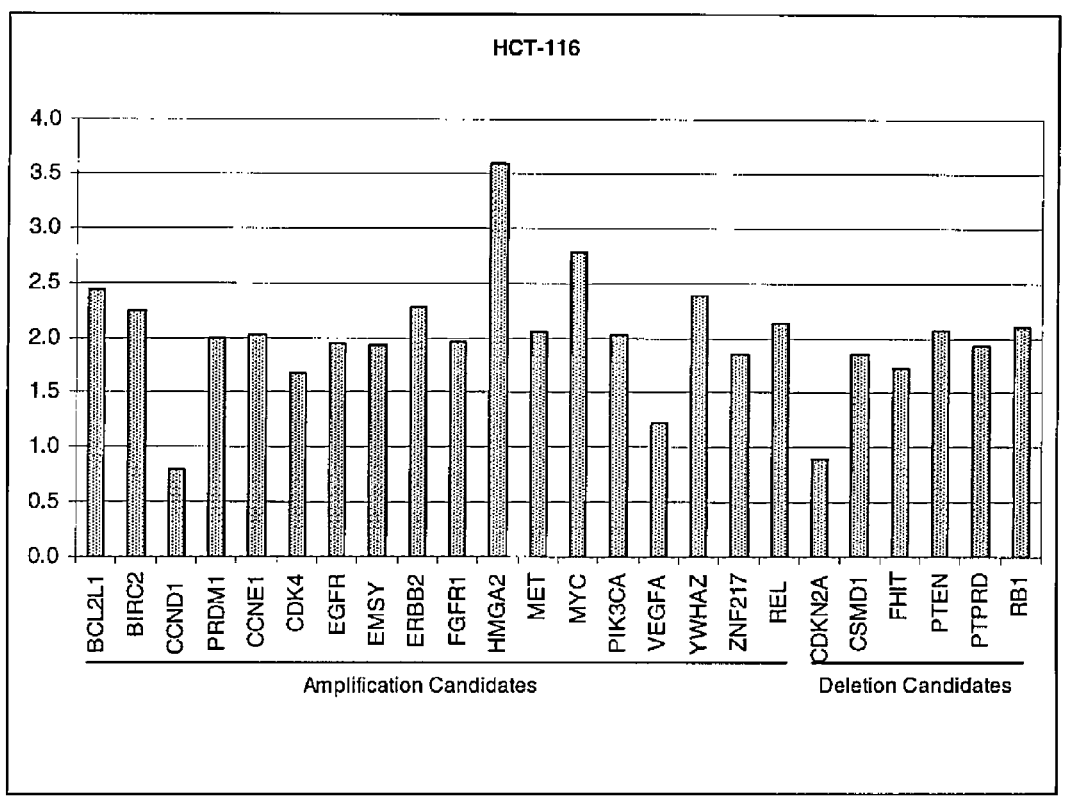
Figure 17G:
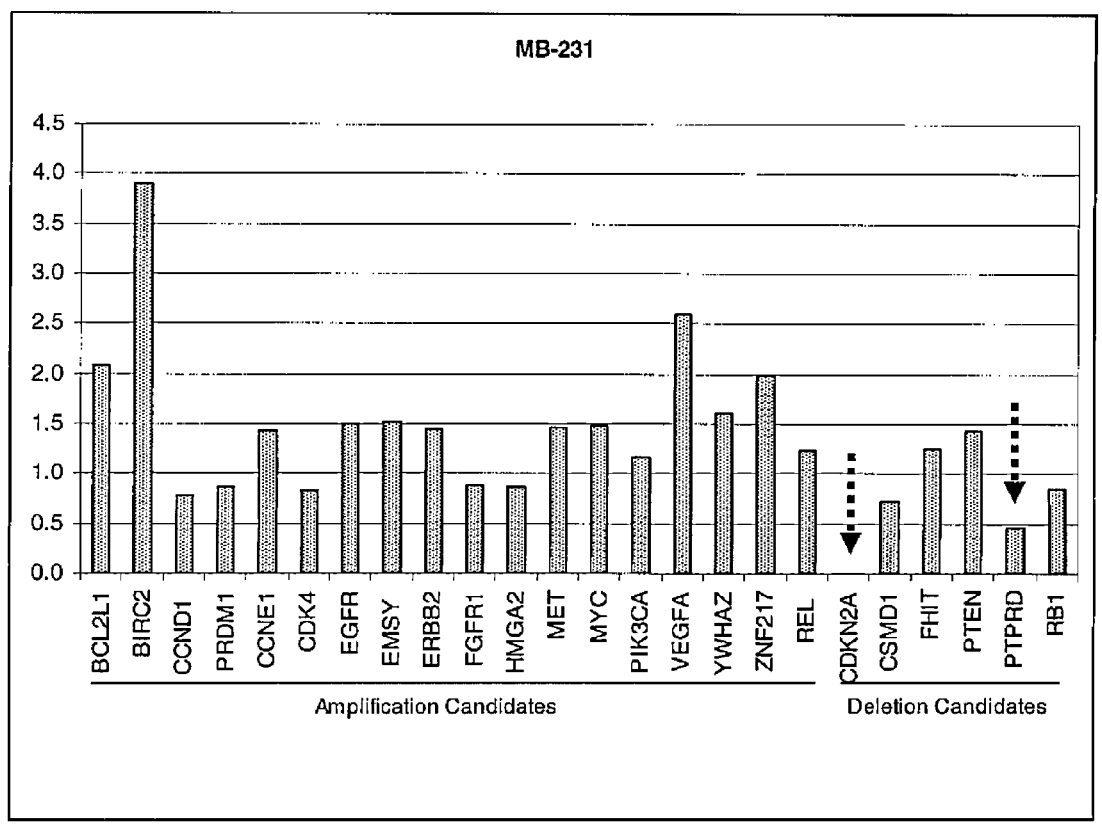
Figure 17H:
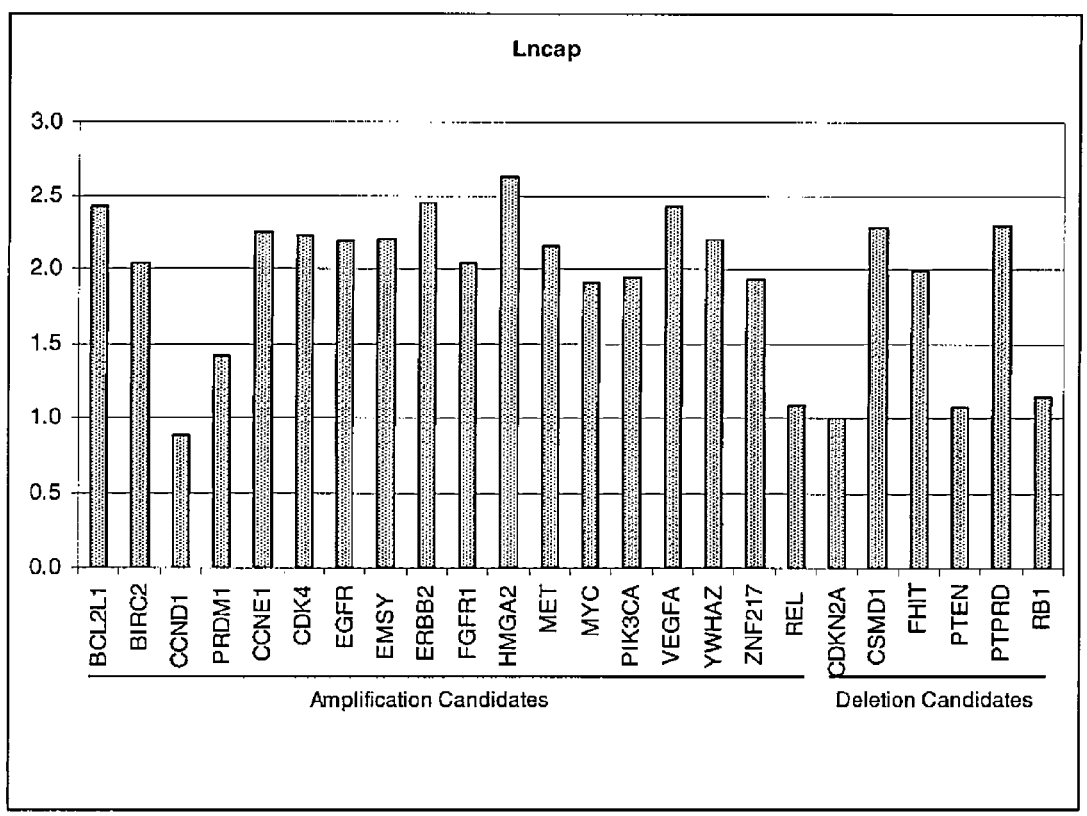
Figure 17I:
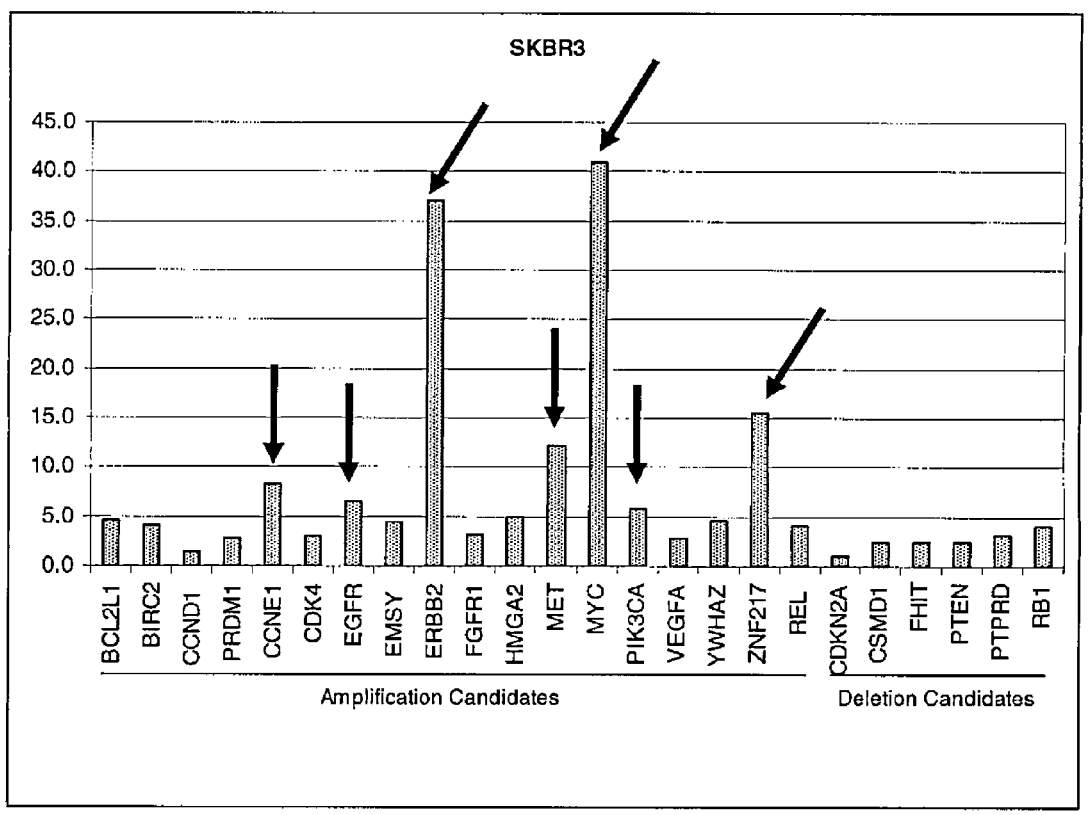

Further, the original MMSA PCR system included a complex component, buffer C. To simplify the production of the mastermix we tested candidate buffers containing fewer than the full constituency of buffer C to determine whether an equally active buffer could be obtained. Our tests revealed that equal effectiveness was obtained solely with Tween 20. FIG. 10 illustrates that the same curve shapes and Ct values between mastermix made with Buffer C and mastermix made with the same amount of Tween 20 were obtained, indicating Tween 20 alone was sufficient.

Example 6

In the foregoing examples, the following methods were used for MNAzyme Real-Time PCR assays. Assays used human genomic DNA (Promega, Madison, Wis.) as a template. Each 10 ul reaction contained limiting primer (40 nM), regular primer (200 nM), partzymes (200 nM each), 2×PCR buffer, probe labeled with fluorophore and quencher (e.g., FAM and Blackhole quencher) (200 nM), and genomic DNA. Four different concentrations of genomic DNA (0.2 ng/ul, 0.05 ng/ul, 0.0125 ng/ul and 0.003125 ng/ul) were used to calculate PCR efficiency of each design. Reactions were run and data collected using the 7900HT Fast Real-Time PCR System (Life Technologies Corporation, Carlsbad, Calif.) with following cycling condition:

| Stage 1 | | 95 C.-15 min |
|---------|-----------|-----------------------------|
| Stage 2 | 10 cycles | 95 C.-15 sec |
|         |           | 60 C.-1 min |
| Stage 3 | 40 cycles | 95 C.-15 sec |
|         |           | 50 C.-1 min, Data collection |

Example 7

Multiplex Assay for Virus Detection

This example demonstrates use of MNAzyme technology, particularly the design methods described above in Examples 2, 3, and 4, for virus detection. Specifically, this example demonstrates simultaneous and discriminatory detection of Human Immunodeficiency Virus Type 1 (HIV-1) RNA, Hepatitis C Virus (HCV) RNA and Hepatitis B Virus (HBV) DNA using real time PCR and multiplex MNAzyme detection. These methods may be particularly suitable for screening (preferably high-throughput screening) of a large number of samples, which may be used to screen for pathogens in a blood bank, a bank of cells or tissues intended for transplant, patient samples, etc.

Primer and partzyme designs were generated using our MNAzyme design program, which implemented the design methods described above in examples 2, 3 and 4. The primers were selected for quantitative PCR amplification of sequences within the specified template (carried out in this instance using the Qiagen Rotor Gene). The partzyme sequences were designed so that each amplicon could hybridized to its respective Partzyme A and Partzyme B, resulting in an MNAzyme able to hybridize to and specifically cleave the probe sequence, thereby liberating the fluorophore from the quencher and producing a detectable fluorescence signal upon appropriate excitation. The four respective fluorophores have distinguishable fluorescent characteristics, permitting the concentration of each free fluorophore to be quantified in the same reaction.

Due to high mutation rate and large numbers of genetic variants, relatively conserved region in representative sequences were selected for amplification and MNAzyme detection. HBV was designed to target PreC region of subtype ayr (GenBank: X04615.1). HCV was designed in 5'UTR region of a genotype 1 representative (NC_004102.1). HIV-1 was designed in GAG CDS region in consensus sequence of group M genotype B. HIV sequences were obtained from the HIV Sequence Database operated by Los Alamos National Security, LLC, for the U.S. Department of Energy's National Nuclear Security Administration (www.hiv.lanl.gov/content/sequence/HIV/mainpage.html). Also see HIV Sequence Compendium 2009, Kuiken et al., eds., Theoretical Biology and Biophysics, Los Alamos National Laboratory, Los Alamos, N. Mex. which is incorporated by reference herein in its entirety. The sequences to be detected are shown in Table 4 ("Template").

Though the templates used in this example were synthetic DNAs, these methods may be readily adapted for detection of RNAs (e.g., HIV-1 or HCV genomic RNAs). For example, reverse transcriptase and a suitable complementary primer may be used to synthesize DNA complementary to the RNA to be detected.

The resulting probe, primer, and partzyme sequences used in this example are shown in Table 4. Four different probes (referred to as Sub2-Cy5, Sub6-Hex, Sub3-Rox and Sub17-Fam) were used for four targets respectively (HBV, HIV-1, PPC and HCV). PPC was a sample-independent positive control polynucleotide added to each sample, amplification of which confirms successful PCR amplification; failure to amplify or detect PPC indicates identifies a failed reaction for which a negative result would not be informative. Additionally, target copy number may be computed using ΔΔCt values as described below, wherein ΔCt values may be computed between each target and the sample-independent positive control. Further exemplary positive control sequences are disclosed in U.S. Pub. No. 20090124516, which is incorporated by reference herein in its entirety. Though not included in this example, a positive control sequence associated with the sample may also be amplified and detected (for example, where the samples are expected to contain human cells or human DNA or RNA, a human genomic DNA sequence or human RNA sequence may be used as a positive control).

Each probe used in this example included a 5' fluorophore and 3' quencher. Each partzyme A included the catalytic core sequence ACAACGA (SEQ ID NO: 3) and each partzyme B included the catalytic core sequence GGCTAGCT (SEQ ID NO: 12).

TABLE 4

Primers, partzymes and template sequences used in Example 7.
Partzyme catalytic core sequences are shown in bold and underlined.

| Target | Name | Sequence | SEQ ID NO |
|---|---|---|---|
| HIV-1 | Limiting Primer | AGAATGCTGGTAGGGCTATAC | 17 |
| HIV-1 | Reverse Primer | CAGGAACAAATAGGATGGATG | 18 |
| HIV-1 | Partzyme A | TCTTTTATAGATTTCTCCTACTGACAACGAGAGGCGTGAT | 19 |
| HIV-1 | Partzyme B | CTGGGAGGAAGGCTAGCTGGATAGGTGGATTATTTGT/3Phos/ | 20 |
| HIV-1 | Template | CAGGAACAAATAGGATGGATGACAAATAATCCACCTATCCCAGTAGGAGAAATCTATAAAAGATGGATAATCCTGGGATTAAATAAAATAGTAAGAATGTATAGCCCTACCAGCATTCT | 21 |
| HIV-1 | Probe | /5HEX/ATCACGCCTCrGrUTCCTCCCAG/3BHQ_1/* | 22 |
| HBV | Limiting Primer | TTAAAGACTGGGAGGAGTTG | 23 |
| HBV | Reverse Primer | ACATGAGATGATTAGGCAGAG | 24 |
| HBV | Partzyme A | AGGTCTTTGTACTAGGAGGACAACGAGAGGAAACCTT | 25 |
| HBV | Partzyme B | TGCCCAGGGAGGCTAGCTCTGTAGGCATAAATTGGTCT/3Phos/ | 26 |
| HBV | Template | ACATGAGATGATTAGGCAGAGGGGAAAAAGTTGCATGGTGCTGGTGAACAGACCAATTTATGCCTACAGCCTCCTAGTACAAAGACCTTTAACCTAATCTCCTCCCCCAACTCCTCCCAGTCTTTAA | 27 |
| HBV | Probe | /5CY5/AAGGTTTCCTCrGrUCCCTGGGCA/3BHQ_2/* | 28 |
| HCV | Limiting Primer | GGCGTTAGTATGAGTGTCGTG | 29 |
| HCV | Reverse Primer | GAGCGGGTTTATCCAAGAAAG | 30 |
| HCV | Partzyme A | ATAGTGGTCTGCGGAACCGACAACGAGTCCCATGTT | 31 |
| HCV | Partzyme B | ACCCAGCCAAGGCTAGCTGTGAGTACACCGGAATTGCC/3Phos/ | 32 |
| HCV | Template | GAGCGGGTTTATCCAAGAAAGGACCCGGTCGTCCTGGCAATTCCGGTGTACTCACCGGTTCCGCAGACCACTATGGCTCTCCCGGGAGGGGGGGTCCTGGAGGCTGCACGACACTCATACTAACGCC | 33 |

TABLE 4-continued

Primers, partzymes and template sequences used in Example 7.
Partzyme catalytic core sequences are shown in bold and underlined.

| Target | Name | Sequence | SEQ ID NO |
|---|---|---|---|
| HCV | Probe | /56-FAM/AACATGGGACrGrUTGGCTGGGT/3BHQ_1/* | 34 |
| PPC | Limiting Primer | AGCTGATCTCCGAGGTGCAG | 35 |
| PPC | Reverse Primer | AGCTCTCGTACCGTGTTTGCTGT | 36 |
| PPC | Partzyme A | ACTTCACTGATGTCCCCTGACAACGAGGTTGTGCTG | 37 |
| PPC | Partzyme B | CGGTTGGTGAGGCTAGCTGTCGATGGTACGGATGGTT/3Phos/ | 38 |
| PPC | Template | AGCTCTCGTACCGTGTTTGCTGTTGATTACAACCATCCGTACCATCGACCAGGGGACATCAGTGAAGTCTGCGATGATGTGTTTCCAGTAACAGTCGCTCCTTCTAAGTTAGCGTTCGTTAGAAATCTGCACCTCGGAGATCAGCT | 39 |
| PPC | Probe | /56-ROXN/CAGCACAACCrGrUCACCAACCG/3BHQ_2/* | 40 |

* Nucleotide with a prefix "r" represents RNA base.
Abbreviations used in Table 4 are as follows:
/SHEX/ indicates coupling of the 5' end of the polynucleotide to the fluorophore HEX (6 - carboxy - 2',4,4',5',7,7' - hexachlorofluorescein, succinimidyl ester).
/5CY5/ indicates coupling of the 5' end of the polynucleotide to the fluorophore CY5.
/56-FAM/ indicates coupling of the 5' end of the polynucleotide to the fluorophore 6-FAM (6-carboxyfluorescein).
/56-ROXN/ indicates coupling of the 5' end of the polynucleotide to the fluorophore 6-ROXN (6 - carboxy - X - rhodamine).
/3BHQ_1/ indicates coupling of the 3' end of the polynucleotide to the quencher BHQ 1 (Black Hole Quencher 1, Biosearch Technologies, Inc., Novato, CA).
/3BHQ_2/ indicates coupling of the 3' end of the polynucleotide to the quencher BHQ 2 (Black Hole Quencher 2, Biosearch Technologies, Inc., Novato, CA).
/3Phos/ indicates a polynucleotide having a 3' phosphate.

Multiplex PCR and MNAzyme detection was performed by using synthetic DNA as templates. Six different template concentrations were used, containing between 16 and 4000 template copies per 25 uL reaction, as well as a negative control containing zero copies of each template (in these experiments, each of the four templates was added to each sample in the same number of copies). Each row in Table 5 shows the cycle number at which the fluorescence intensity reached a set threshold selected within the exponential amplification range (Ct) detected from each of the four probes. Results presented are the average and standard deviation of six replicates of each experiment. As few as 16 copies of each synthetic template in a 25 uL reaction could be detected (i.e., gave a fluorescence signal distinguishable from background). As expected, Ct decreased with increasing template concentration, with a slope ranging between −3.39 and −3.52, efficiency between 0.92 and 0.97, and R-squared (RSQ) value between 0.995 and 0.997.

To investigate the assay performance in human genomic DNA background, 10 ng of human universal genomic DNA was spiked into each 25 uL reaction as described in the preceding paragraph. No significant Ct difference was observed compared to assays without gDNA, indicating the assay can be performed in high human genome background (Table 6).

It is worth noting that the standard deviation was close to or higher than 1 when there were only 16 copies of templates for most assays. This could be explained by sampling error due to the limited amount of templates in the assay. The observed high standard deviation may indicate a relatively lower quantification accuracy of the assay for samples containing a low template concentration. However, the detection limit of this assay could reach down to less than 16 copies in the reaction for qualification purpose because the amplification curves and Cts are separated nicely from that of no-template control (NTC). The limit of detection of currently available products, such as Procleix Ultrio Assay from Gen-Probe and COBAS TaqScreen MPX Test from Roche Molecular Systems, with >90% of detection rate, is roughly around 30 copies per mL sample. The sensitivity demonstrated by these results was in a similar range, if not better, than with these products.

To investigate the detection of different genetic variants, several reference sequences were retrieved from NCBI Genbank (www.ncbi.nlm.nih.gov/), the HIV Sequence Database operated by Los Alamos National Security, LLC, for the U.S. Department of Energy's National Nuclear Security Administration (www.hiv.lanl.gov/content/sequence/HIV/mainpage-.html), and HCV sequence database operated by Los Alamos National Security, LLC. for the U.S. Department of Energy's National Nuclear Security Administration (hcv.lanl.gov/content/sequence/HCV/ToolsOutline.html), and aligned along with designed sequences. Alignment results are shown in FIG. 12 (HBV), FIG. 13 (HCV) and FIG. 14 (HIV).

From the sequence alignments, it is expected that these assays will be able to detect majority of the genetic variants listed with reasonably high sensitivity. A few variants, such as HBV genotype G&H, HIV-1 group O&N, and HCV genotype 2, 4, 5, might demonstrate decreased sensitivity with these specific designs due to mismatch(es) in locations expected to contribute to activity, e.g., point such as near 3' end of primer, or junction region of partzymes A&B. However, it is expected that sensitivity of detection of these variant viral sequences could be improved using variants of the primer and/or partzyme sequences disclosed in table 4 above, e.g., by using a mixture of primers and/or partzymes that eliminate mismatches and restore base pairing with these variants.

Thus, these results demonstrate that these design methods can be used to select amplification primers and MNAzyme sequences for sensitive and specific multiplex detection of viral sequences such as HBV, HCV and HIV in human samples, and moreover that the concentration of viral nucleic acids can be accurately quantified using these methods (with quantification generally accuracy increasing with viral concentration).

sequences of primers, partzymes, and probes used in this example are shown in FIG. 15A-C. Each reaction was a duplex reaction that amplified and detected two targets, specifically a gene of interest (GOI) and a reference gene (RNase P gene in this case, though numerous other reference genes could be readily selected by those of ordinary skill in the art). Each reaction included two probes (Sub2-FAM, SEQ ID NO: 141 and Sub6-HEX, SEQ ID NO: 142): one (Sub2-FAM) was for the gene of interest (GOI), and the other (Sub6-HEX) was for reference gene for normalization to minimize well-to-well

TABLE 5

Multiplex qPCR assay with MNAzyme detection with serial dilution of templates.

| COPY NUMBER IN 25 MICROLITER REACTION | HBV-CY5 | | HCV-FAM | | HIV-HEX | | PPC-ROX | |
|---|---|---|---|---|---|---|---|---|
| (HBV; HCV; HIV; PPC) | Ave Ct | StDev | Ave Ct | StDev | Ave Ct | StDev | Ave Ct | StDev |
| 4000; 4000; 4000; 4000 | 16.63 | 0.35 | 17.42 | 0.41 | 19.64 | 0.58 | 16.39 | 0.23 |
| 1000; 1000; 1000; 1000 | 18.76 | 0.22 | 19.4 | 0.6 | 21.97 | 0.59 | 18.54 | 0.17 |
| 250; 250; 250; 250 | 20.93 | 0.35 | 21.65 | 0.25 | 23.82 | 0.44 | 20.69 | 0.17 |
| 62.5; 62.5; 62.5; 62.5 | 23.12 | 0.36 | 23.85 | 0.31 | 25.65 | 0.53 | 22.93 | 0.42 |
| 16; 16; 16; 16 | 24.67 | 0.85 | 25.47 | 0.71 | 28.38 | 1.32 | 24.42 | 0.57 |
| 0; 0; 0; 0 | 35.9 | 6.37 | 36.69 | 5.23 | 39.78 | 0.55 | 38.77 | 3.01 |
| Slope | −3.39 | | −3.41 | | −3.52 | | −3.4 | |
| Efficiency | 0.97 | | 0.96 | | 0.92 | | 0.97 | |
| RSQ | 0.997 | | 0.997 | | 0.995 | | 0.996 | |

TABLE 6

Multiplex qPCR assay with MNAzyme detection in human genomic DNA background.

| COPY NUMBER IN 25 UL RXN | HBV-Cy5 | | HCV-FAM | | HIV-HEX | | PPC-ROX | |
|---|---|---|---|---|---|---|---|---|
| (HBV; HCV; HIV; PPC) | Ave Ct | StDev | Ave Ct | StDev | Ave Ct | StDev | Ave Ct | StDev |
| 4000; 4000; 4000; 4000 | 16.86 | 0.39 | 17.75 | 0.40 | 19.95 | 0.32 | 16.74 | 0.25 |
| 1000; 1000; 1000; 1000 | 19.33 | 0.42 | 20.25 | 0.42 | 22.65 | 0.58 | 19.12 | 0.36 |
| 250; 250; 250; 250 | 21.05 | 0.51 | 22.13 | 0.59 | 24.43 | 0.81 | 20.98 | 0.47 |
| 62.5; 62.5; 62.5; 62.5 | 23.19 | 0.69 | 24.22 | 0.54 | 26.13 | 0.68 | 23.00 | 0.42 |
| 16; 16; 16; 16 | 24.70 | 0.89 | 26.29 | 0.96 | 28.27 | 0.97 | 25.01 | 1.81 |
| 0; 0; 0; 0 | 31.80 | 7.92 | 30.44 | 5.04 | 38.59 | 2.77 | 40.00 | 0.00 |
| Slope | −3.25 | | −3.50 | | −3.34 | | −3.39 | |
| Efficiency | 1.03 | | 0.93 | | 0.99 | | 0.97 | |
| RSQ | 0.99 | | 1.00 | | 0.99 | | 1.00 | |

10 ng human universal gDNA was added to each reaction.

Example 8

Duplex Assay to Detect DNA Copy Number Variation

This example demonstrates use of MNAzyme methods for DNA copy number analysis, which may be used for number alteration studies. This example describes characterization of cancer cell lines, and the same general methods are expected to be usable for detecting or characterizing neoplasias, as well as pre-implantation and other genetic testing. For example, it is expected that these methods can be used to detect gene amplification and/or deletion events associated with cancer and other malignancies, as well as pre-malignant conditions and elevated risk of developing malignancies.

A panel of 24 target genes was selected based on literature survey. These genes were reported to be frequently amplified or deleted in different cancer cells. Primers and partzymes for detection of these target genes were designed using our MNAzyme design program as described in Example 7. The variation and comparison across all tested samples. In addition to the cancer cell samples, a "calibrator" sample containing normal genomic DNA (expected to contain two copies of each gene) was also analyzed. Use of duplex reactions that analyzed one gene of interest and one reference gene, along with use of normal diploid genomic DNA as a calibrator, allowed ΔΔCT to be used to accurately determine copy number across a set of samples for a given target, as further described below (ΔCT is the difference in CT between the gene of interest and reference gene in a given sample, and ΔΔCT is the difference in ΔCT between different samples).

All reactions were performed in an ABI 7900HT fast real-time PCR system with MNAzyme chemistry and cycling conditions as described in Example 6 above, except that reactions were done in duplex (thus, each primer, probe, and partzyme from both reactions being performed in duplex was added in the specified concentration) using 0.2 ng/microliter total genomic DNA purified from the specified cell types as the template.

In one experiment, the breast cancer cell line MCF7 was titrated with normal diploid human cells to study the detection sensitivity of this platform. The normal DNA percentage in each dilution point was: 0.0%, 12.5%, 25.0%, 50.0%, 75.0%, 87.5% and 100.0% respectively. Representative results that were obtained for two genes (ZNF217 and CDKN2A) are shown graphically in FIG. 16A-B, with detected gene copy number (determined from ΔΔCT values) shown on the Y-axis. The gene copy number (CN) is calculated using Ct values for the GOI and reference gene that were detected from normal diploid genomic DNA (expected to contain two copies of the target gene per genome) as the calibrator, based on the expectation that the copy number of reference gene is two copies per genome in both calibrator and test samples. The copy number of the target gene in the test sample was calculated by the ΔΔCT method, using the following formulae:

$$CN = 2*(2^{(\Delta Ct_{Calibrator} - \Delta Ct_{Sample})}) \text{ where}$$

$\Delta Ct_{Calibrator} = Ct_{target} - Ct_{reference}$ of the calibrator, i.e., $Ct_{target}$ and $Ct_{reference}$ in this equation refer to the Ct value measured for the target and reference genes, respectively, in the calibrator sample (e.g., normal diploid DNA), and $\Delta Ct_{Sample} = Ct_{target} - Ct_{reference}$ of the test sample, i.e., $Ct_{target}$ and $Ct_{reference}$ in this equation refer to the Ct value measured for the target and reference genes, respectively, in the test sample (e.g., cancer cell line DNA).

In undiluted MCF7 DNA samples, ZNF217 was detected to be amplified (FIG. 16A); and CDKN2A was detected to be homozygously deleted (FIG. 16B). For samples containing a mixture of MCF7 and normal DNA, the results for CDKN2A showed that 0.25 copy difference can be discriminated across the mixed samples, demonstrating the sensitive power of this method. Thus, it is expected that loss of heterozygosity can be detected even in heterogeneous samples, e.g., samples in which only 50% of the cells are heterozygous, or samples in which only 25% of cells have deleted both copies of a gene.

In the second experiment, copy number alteration profiles of the twenty-four target genes in nine different cancer cell lines were investigated. These twenty-four target genes were: BCL2L1, BIRC2, CCND1, PRDM1, CCNE1, CDK4, EGFR, EMSY, ERBB2, FGFR1, HMGA2, MET, MYC, PIK3CA, VEGFA, YWHAZ, ZNF217, REL, CDKN2A, CSMD1, FHIT, PTEN, PTPRD, and RB1. The nine cancer cell lines were: A375, MCF7, PC3, A549, SW480, HCT-116, MB-231, LNCaP, and SKBR3.

Results of these experiments are shown graphically in FIG. 17, with the detected gene copy number (determined using the ΔΔCT method, computed by the formula described above) shown on the Y-axis. We were able to identify both gene amplification and homozygous deletion events in different cancer cell lines. For example, an elevated number of copies of CCNE1, EGFR, ERBB2, MET, MYC, PIK3CA, and ZNF217 were detected in the cell line SKBR3; and an elevated number of copies of MYC was detected in cell line SW480, and an elevated number of copies of CCNE1 was detected in the cell line A549 and an elevated number of copies of ZNF217 was detected in the cell line MCF7. Additionally, a decreased number of copies of CDKN2A was detected in each of the cell lines MCF7, A549, and MB231; a decreased number of copies of PTEN was detected in the cell line PC3, and a decreased number of copies of PTPRD was detected in the cell line MB231.

Overall, this example demonstrated that MNAzyme duplex PCR platform can be sued for copy number alteration analysis. For example, these methods may be used as a diagnostic or screening tool, or as a discovery tool.

REFERENCES

Zipper H, Brunner H, Bernhagen J, Vitzthum F (2004). "Investigations on DNA intercalation and surface binding by SYBR Green I, its structure determination and methodological implications". Nucleic acids research 32 (12): e103. doi:10.1093/nar/gnh101. PMID 15249599.

Schneeberger C., Speiser, P., Kury, F. and Zeillinger, R. (1995) Quantitative detection of reverse transcriptase-PCR products by means of a novel and sensitive DNA stain. PCR Methods Appl., 4, 234-238.

Jin X., Dong, F. and Singer, V. L. (1996) SYBR Green I nucleic acid gel stain provides a sensitive fluorescent method for detecting gel mobility shift products. FASEB J., 10, A1128.

Mokany E, Bone S M, Young P E, Doan T B, Todd A V. MNAzymes, a versatile new class of nucleic acid enzymes that can function as biosensors and molecular switches. J Am Chem. Soc. 2010 Jan. 27; 132(3):1051-9.

Nauwelaers D, Vijgen L, Atkinson C, Todd A, Geretti A M, Van Ranst M, Stuyver L. Development of a real-time multiplex RSV detection assay for difficult respiratory samples, using ultrasone waves and MNAzyme technology. J Clin Virol. 2009 November; 46(3):238-43. Epub 2009 Sep. 15.

Gerasimova Y V, Kolpashchikov D M. Nucleic acid detection using MNAzymes. Chem. Biol. 2010 Feb. 26; 17(2):104-6.

Teller C, Willner I. Functional nucleic acid nanostructures and DNA machines. Curr Opin Biotechnol. 2010 Aug. 18. [Epub ahead of print]

WO/2007/041774, Mokany et al., Apr. 19, 2007

U.S. Pat. No. 5,210,015 (Gelfand et al., May 11, 1993)

U.S. Pat. No. 7,413,708, Mayrand, Aug. 19, 2008

U.S. Pat. No. 5,723,591, Livak et al. Mar. 3, 1998

U.S. Pat. No. 5,876,930, Livak et al. Mar. 2, 1999

U.S. Pat. No. 5,866,336, Nazarenko et al., Feb. 2, 1999

U.S. Pat. No. 6,090,552, Nazarenko et al., Jul. 18, 2000

U.S. Pat. No. 6,150,097, Tyagi et al., Nov. 21, 2000

U.S. Pat. No. 5,807,718, Joyce et al., Sep. 15, 1998

U.S. Pat. No. 6,201,113, Todd et al., Mar. 13, 2001

U.S. Pat. No. 6,326,174, Joyce et al., Dec. 4, 2001

U.S. Pat. No. 6,183,959, Thompson Feb. 6, 2001

U.S. Pat. No. 7,141,665, Joyce et al., Nov. 28, 2006

U.S. Pat. No. 7,355,035, Atkins et al., Apr. 8, 2008

U.S. Pat. No. 6,174,670, Wittwer et al., Jan. 16, 2001

U.S. PGPub. No. 20100221711, Respiratory Syncytial Virus (RSV) Viral Load Detection Assay U.S. PGPub. No. 20100136536, Molecular Switches And Methods For Their Use U.S. PGPub. No. 20100035229, METHODS, PLASMID VECTORS AND PRIMERS FOR ASSESSING HIV VIRAL FITNESS U.S. PGPub. No. 20070231810, Multicomponent nucleic acid enzymes and methods for their use Each of the publications cited herein is hereby incorporated by reference in its entirety.

The invention claimed is:

1. A method of designing and synthesizing MNAzyme sensor arms that detects an assembly facilitator that comprises a nucleic acid sequence, the method comprising:

identifying a junction sequence having the sequence 5'-CG-3' within said assembly facilitator wherein the center of said junction sequence is in between said G and C residues of said junction sequence;

selecting as the Partzyme A sensor arm a sequence capable of hybridizing to a sequence of said assembly facilitator beginning at the center of said junction sequence and extending 3' therefrom, and selecting as the Partzyme B sensor arm a sequence capable of hybridizing to a sequence of said assembly facilitator beginning at the center of said junction sequence and extending 5' therefrom, wherein said MNAzyme comprises a Partzyme A and a Partzyme B that self-assemble in the presence of said assembly facilitator to form a catalytically active multi-component nucleic acid enzyme (MNAzyme), wherein said Partzyme A comprises a Partzyme A catalytic core, Partzyme A sensor arm, and a Partzyme A substrate arm, and wherein said Partzyme B comprises a Partzyme B catalytic core, Partzyme B sensor arm, and a Partzyme B substrate arm, wherein said Partzyme A sensor arm and said Partzyme B sensor arm each comprise a nucleic acid, and wherein said assembly facilitator comprises a nucleic acid that is complementary to said Partzyme A sensor arm and comprises a nucleic acid that is complementary to said Partzyme B sensor arm, wherein the base at the 5' terminus of said Partzyme B sensor arm is not G; and synthesizing a nucleic acid comprising said Partzyme A sensor arm and synthesizing a nucleic acid comprising said Partzyme B sensor arm.

2. The method of claim 1, wherein the center of said junction sequence is contained within a predicted stem loop structure of said assembly facilitator.

3. The method of claim 1, wherein one of the two bases at the 3' terminus of the Partzyme A sensor arm is not G, or the base immediately 3' to the 5' terminus of said Partzyme B sensor arm is not A.

4. The method of claim 1, wherein the base 3' of said Partzyme A sensor arm is not complementary to the base 5' of said nucleic acid that is complementary to said Partzyme A sensor arm, the second base 3' of said Partzyme A sensor arm is not complementary to the second base 5' of said nucleic acid that is complementary to said Partzyme A sensor arm, and the third base 3' of said Partzyme A sensor arm is not complementary to the third base 5' of said nucleic acid that is complementary to said Partzyme A sensor arm.

5. The method of claim 1, wherein the base 5' of said Partzyme B sensor arm is not complementary to the base 3' of said nucleic acid that is complementary to said Partzyme B sensor arm, the second base 5' of said Partzyme B sensor arm is not complementary to the second base 3' of said nucleic acid that is complementary to said Partzyme B sensor arm, and the third base 5' of said Partzyme B sensor arm is not complementary to the third base 3' of said nucleic acid that is complementary to said Partzyme B sensor arm.

6. The method of claim 1, wherein the Partzyme A catalytic core comprises a nucleic acid selected from the group consisting of SEQ ID NOS: 1-10, sequences at least 80% identical to said sequences, and sequences at least 90% similar to said sequences.

7. The method of claim 1, wherein the Partzyme B catalytic core comprises a nucleic acid selected from the group consisting of SEQ ID NOS: 11-16, sequences at least 80% identical to said sequences, and sequences at least 90% similar to said sequences.

8. The method of claim 1, further comprising detecting the presence of said assembly facilitator, the method comprising contacting said Partzyme A and said Partzyme B with a sample putatively containing said assembly facilitator, under conditions permitting: (1) the self-assembly of said catalytically active MNAzyme, and (2) the catalytic activity of said catalytically active MNAzyme; and detecting the presence of the catalytic activity of said catalytically active MNAzyme, wherein the presence of the catalytic activity is indicative of the presence of said assembly facilitator.

9. The method of claim 8, further comprising providing at least a third oligonucleotide component that contacts at least a portion of either or both of the Partzyme A and the Partzyme B to self-assemble the MNAzyme, wherein said assembly facilitator comprises a nucleic acid.

10. The method of claim 8, further comprising a step of amplifying the assembly facilitator or a nucleic acid containing the sequence of the reverse complement of the assembly facilitator.

11. The method of claim 8, wherein the step of amplifying comprises one or more selected from the group consisting of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), and reverse transcription polymerase chain reaction (RT-PCR).

12. The method of claim 8, wherein the step of detecting the presence of the catalytic activity of said catalytically active MNAzyme comprises providing a substrate, said substrate capable of being modified by said MNAzyme, wherein said modification of said substrate by said MNAzyme provides a detectable effect wherein said substrate comprises a nucleic acid and wherein said substrate arms engage said substrate through complementary base pairing.

13. The method of claim 8, wherein the substrate comprises a detectable portion and a quencher portion, wherein upon modification of the substrate by the MNAzyme, a detectable effect provided by the detectable portion is increased or decreased.

14. The method of claim 8, wherein said assembly facilitator comprises at least one HPV polynucleotide and said method is used to identify, detect and/or quantitatively measure one or more HPV serotypes in a sample.

15. The method of claim 8, wherein said assembly facilitator includes at least one of HIV-1, HBV, or HCV polynucleotides.

16. The method of claim 2, wherein said predicted stem loop is identified using the structure prediction algorithms implemented by the mfold or Unafold program.

17. The method of claim 2, wherein said assembly facilitator is selected from the group consisting of: BCL2L1, BIRC2, CCND1, PRDM1, CCNE1, CDK4, EGFR, EMSY, ERBB2, FGFR1, HMGA2, MET, MYC, PIK3CA, YEGFA, YWHAZ, ZNF217, REL, CDKN2A, CSMD1, FHT, PTEN, PTPRD, and RB1.

18. A method of designing and synthesizing MNAzyme sensor arms that detects an assembly facilitator that comprises a nucleic acid sequence, the method comprising:

identifying a junction sequence having the sequence 5'-CG-3' within said assembly facilitator, wherein the sequence wherein the center of said junction sequence is in between said G and C residues of said junction sequence, and wherein said junction sequence is contained within a predicted stem loop of said assembly facilitator sequence;

selecting as the Partzyme A sensor arm a sequence capable of hybridizing to a sequence of said assembly facilitator beginning at the center of said junction sequence and extending 3' therefrom, and selecting as the Partzyme B sensor arm a sequence capable of hybridizing to a sequence of said assembly facilitator beginning at the center of said junction sequence and extending 5' therefrom, wherein said MNAzyme comprises a Partzyme A and a Partzyme B that self-assemble in the presence of said assembly facilitator to form a catalytically active multi-component nucleic acid enzyme (MNAzyme), wherein said Partzyme A comprises a Partzyme A catalytic core, Partzyme A sensor arm, and a Partzyme A substrate arm, and wherein said Partzyme B comprises a Partzyme B catalytic core, Partzyme B sensor arm, and a Partzyme B substrate arm, wherein said Partzyme A sensor arm and said Partzyme B sensor arm each comprise a nucleic acid, and wherein said assembly facilitator comprises a nucleic acid that is complementary to said Partzyme A sensor arm and comprises a nucleic acid that is complementary to said Partzyme B sensor arm; and synthesizing a nucleic acid comprising said Partzyme A sensor arm and synthesizing a nucleic acid comprising said Partzyme B sensor arm.

19. The method of claim 18, wherein the Partzyme A catalytic core comprises a nucleic acid selected from the group consisting of SEQ ID NOS: 1-10, sequences at least 80% identical to said sequences, and sequences at least 90% similar to said sequences.

20. The method of claim 18, wherein the Partzyme B catalytic core comprises a nucleic acid selected from the group consisting of SEQ ID NOS: 11-16, sequences at least 80% identical to said sequences, and sequences at least 90% similar to said sequences.

* * * * *

SEQUENCE LISTING

```
<160> NUMBER OF SEQ ID NOS: 154

<210> SEQ ID NO 1
<211> LENGTH: 8
<212> TYPE: DNA
<213> ORGANISM: Artificial
<220> FEATURE:
<223> OTHER INFORMATION: MNAZYME PARTZYME A CATALYTIC CORE
<220> FEATURE:
<221> NAME/KEY: misc_feature
<222> LOCATION: (2)..(2)
<223> OTHER INFORMATION: RNA base

<400> SEQUENCE: 1 tacaacga                                                                 8

<210> SEQ ID NO 2
<211> LENGTH: 8
<212> TYPE: DNA
<213> ORGANISM: Artificial
<220> FEATURE:
<223> OTHER INFORMATION: MNAZYME PARTZYME A CATALYTIC CORE

<400> SEQUENCE: 2 cggtcgaa                                                                 8

<210> SEQ ID NO 3
<211> LENGTH: 7
<212> TYPE: DNA
<213> ORGANISM: Artificial
<220> FEATURE:
<223> OTHER INFORMATION: MNAZYME PARTZYME A CATALYTIC CORE
<220> FEATURE:
<221> NAME/KEY: misc_feature
<222> LOCATION: (7)..(7)
<223> OTHER INFORMATION: RNA base

<400> SEQUENCE: 3 acaacga                                                                  7

<210> SEQ ID NO 4
<211> LENGTH: 8
<212> TYPE: DNA
<213> ORGANISM: Artificial
<220> FEATURE:
<223> OTHER INFORMATION: MNAZYME PARTZYME A CATALYTIC CORE

<400> SEQUENCE: 4 tacaacga                                                                 8

<210> SEQ ID NO 5
<211> LENGTH: 8
<212> TYPE: DNA
<213> ORGANISM: Artificial
<220> FEATURE:
<223> OTHER INFORMATION: MNAZYME PARTZYME A CATALYTIC CORE

<400> SEQUENCE: 5 tacaacga                                                                 8

<210> SEQ ID NO 6
<211> LENGTH: 8
<212> TYPE: DNA
<213> ORGANISM: Artificial
<220> FEATURE:
<223> OTHER INFORMATION: MNAZYME PARTZYME A CATALYTIC CORE

<400> SEQUENCE: 6
```

```
tacaacaa                                                          8

<210> SEQ ID NO 7
<211> LENGTH: 8
<212> TYPE: DNA
<213> ORGANISM: Artificial
<220> FEATURE:
<223> OTHER INFORMATION: MNAZYME PARTZYME A CATALYTIC CORE

<400> SEQUENCE: 7 ttcaacga                                                          8

<210> SEQ ID NO 8
<211> LENGTH: 8
<212> TYPE: DNA
<213> ORGANISM: Artificial
<220> FEATURE:
<223> OTHER INFORMATION: MNAZYME PARTZYME A CATALYTIC CORE

<400> SEQUENCE: 8 tacatcga                                                          8

<210> SEQ ID NO 9
<211> LENGTH: 8
<212> TYPE: DNA
<213> ORGANISM: Artificial
<220> FEATURE:
<223> OTHER INFORMATION: MNAZYME PARTZYME A CATALYTIC CORE

<400> SEQUENCE: 9 tactacga                                                          8

<210> SEQ ID NO 10
<211> LENGTH: 6
<212> TYPE: DNA
<213> ORGANISM: Artificial
<220> FEATURE:
<223> OTHER INFORMATION: MNAZYME PARTZYME A CATALYTIC CORE

<400> SEQUENCE: 10 caacga                                                            6

<210> SEQ ID NO 11
<211> LENGTH: 6
<212> TYPE: DNA
<213> ORGANISM: Artificial
<220> FEATURE:
<223> OTHER INFORMATION: MNAZYME PARTZYME B CATALYTIC CORE

<400> SEQUENCE: 11 ccgagc                                                            6

<210> SEQ ID NO 12
<211> LENGTH: 8
<212> TYPE: DNA
<213> ORGANISM: Artificial
<220> FEATURE:
<223> OTHER INFORMATION: MNAZYME PARTZYME B CATALYTIC CORE

<400> SEQUENCE: 12 ggctagct                                                          8

<210> SEQ ID NO 13
<211> LENGTH: 7
<212> TYPE: DNA
```

```
<213> ORGANISM: Artificial
<220> FEATURE:
<223> OTHER INFORMATION: MNAZYME PARTZYME B CATALYTIC CORE

<400> SEQUENCE: 13 ggctagc                                                                   7

<210> SEQ ID NO 14
<211> LENGTH: 7
<212> TYPE: DNA
<213> ORGANISM: Artificial
<220> FEATURE:
<223> OTHER INFORMATION: MNAZYME PARTZYME B CATALYTIC CORE

<400> SEQUENCE: 14 ggctaga                                                                   7

<210> SEQ ID NO 15
<211> LENGTH: 7
<212> TYPE: DNA
<213> ORGANISM: Artificial
<220> FEATURE:
<223> OTHER INFORMATION: MNAZYME PARTZYME B CATALYTIC CORE

<400> SEQUENCE: 15 ggccagc                                                                   7

<210> SEQ ID NO 16
<211> LENGTH: 9
<212> TYPE: DNA
<213> ORGANISM: Artificial
<220> FEATURE:
<223> OTHER INFORMATION: MNAZYME PARTZYME B CATALYTIC CORE

<400> SEQUENCE: 16 ggctagcta                                                                 9

<210> SEQ ID NO 17
<211> LENGTH: 21
<212> TYPE: DNA
<213> ORGANISM: Artificial
<220> FEATURE:
<223> OTHER INFORMATION: HIV-1 PCR PRIMER

<400> SEQUENCE: 17
agaatgctgg tagggctata c                                                  21

<210> SEQ ID NO 18
<211> LENGTH: 21
<212> TYPE: DNA
<213> ORGANISM: Artificial
<220> FEATURE:
<223> OTHER INFORMATION: HIV-1 PCR PRIMER

<400> SEQUENCE: 18
caggaacaaa taggatggat g                                                  21

<210> SEQ ID NO 19
<211> LENGTH: 40
<212> TYPE: DNA
<213> ORGANISM: Artificial
<220> FEATURE:
<223> OTHER INFORMATION: HIV-1 PARTZYME A

<400> SEQUENCE: 19
tcttttatag atttctccta ctgacaacga gaggcgtgat                              40
```

```
<210> SEQ ID NO 20
<211> LENGTH: 37
<212> TYPE: DNA
<213> ORGANISM: Artificial
<220> FEATURE:
<223> OTHER INFORMATION: HIV-1 PARTZYME B

<400> SEQUENCE: 20
ctgggaggaa ggctagctgg ataggtggat tatttgt                              37

<210> SEQ ID NO 21
<211> LENGTH: 119
<212> TYPE: DNA
<213> ORGANISM: Artificial
<220> FEATURE:
<223> OTHER INFORMATION: HIV-1 PCR TEMPLATE CONTAINING TARGET SEQUENCE

<400> SEQUENCE: 21
caggaacaaa taggatggat gacaaataat ccacctatcc cagtaggaga aatctataaa      60
agatggataa tcctgggatt aaataaaata gtaagaatgt atagccctac cagcattct     119

<210> SEQ ID NO 22
<211> LENGTH: 21
<212> TYPE: DNA
<213> ORGANISM: Artificial
<220> FEATURE:
<223> OTHER INFORMATION: HIV-1 PROBE
<220> FEATURE:
<221> NAME/KEY: misc_feature
<222> LOCATION: (12)..(12)
<223> OTHER INFORMATION: n is uracil
<220> FEATURE:
<221> NAME/KEY: misc_feature
<222> LOCATION: (11)..(12)
<223> OTHER INFORMATION: RNA bases

<400> SEQUENCE: 22
atcacgcctc gntcctccca g                                               21

<210> SEQ ID NO 23
<211> LENGTH: 20
<212> TYPE: DNA
<213> ORGANISM: Artificial
<220> FEATURE:
<223> OTHER INFORMATION: HBV PCR PRIMER

<400> SEQUENCE: 23
ttaaagactg ggaggagttg                                                 20

<210> SEQ ID NO 24
<211> LENGTH: 21
<212> TYPE: DNA
<213> ORGANISM: Artificial
<220> FEATURE:
<223> OTHER INFORMATION: HBV PCR PRIMER

<400> SEQUENCE: 24
acatgagatg attaggcaga g                                               21

<210> SEQ ID NO 25
<211> LENGTH: 37
<212> TYPE: DNA
<213> ORGANISM: Artificial
<220> FEATURE:
<223> OTHER INFORMATION: HBV PARTZYME A
```

<400> SEQUENCE: 25
aggtctttgt actaggagga caacgagagg aaacctt                                37

<210> SEQ ID NO 26
<211> LENGTH: 38
<212> TYPE: DNA
<213> ORGANISM: Artificial
<220> FEATURE:
<223> OTHER INFORMATION: HBV PARTZYME B

<400> SEQUENCE: 26
tgcccaggga ggctagctct gtaggcataa attggtct                               38

<210> SEQ ID NO 27
<211> LENGTH: 127
<212> TYPE: DNA
<213> ORGANISM: Artificial
<220> FEATURE:
<223> OTHER INFORMATION: HBV TEMPLATE CONTAINING TARGET SEQUENCE

<400> SEQUENCE: 27
acatgagatg attaggcaga ggggaaaaag ttgcatggtg ctggtgaaca gaccaattta      60
tgcctacagc ctcctagtac aaagaccttt aacctaatct cctcccccaa ctcctcccag     120
tctttaa                                                              127

<210> SEQ ID NO 28
<211> LENGTH: 22
<212> TYPE: DNA
<213> ORGANISM: Artificial
<220> FEATURE:
<223> OTHER INFORMATION: HBV PROBE
<220> FEATURE:
<221> NAME/KEY: misc_feature
<222> LOCATION: (13)..(13)
<223> OTHER INFORMATION: n is uracil
<220> FEATURE:
<221> NAME/KEY: misc_feature
<222> LOCATION: (12)..(13)
<223> OTHER INFORMATION: RNA bases

<400> SEQUENCE: 28
aaggtttcct cgnccctggg ca                                               22

<210> SEQ ID NO 29
<211> LENGTH: 21
<212> TYPE: DNA
<213> ORGANISM: Artificial
<220> FEATURE:
<223> OTHER INFORMATION: HCV PCR PRIMER

<400> SEQUENCE: 29
ggcgttagta tgagtgtcgt g                                                21

<210> SEQ ID NO 30
<211> LENGTH: 21
<212> TYPE: DNA
<213> ORGANISM: Artificial
<220> FEATURE:
<223> OTHER INFORMATION: HCV PCR PRIMER

<400> SEQUENCE: 30
gagcgggttt atccaagaaa g                                                21

<210> SEQ ID NO 31
<211> LENGTH: 36

```
<212> TYPE: DNA
<213> ORGANISM: Artificial
<220> FEATURE:
<223> OTHER INFORMATION: HCV PARTZYME A

<400> SEQUENCE: 31
atagtggtct gcggaaccga caacgagtcc catgtt                          36

<210> SEQ ID NO 32
<211> LENGTH: 38
<212> TYPE: DNA
<213> ORGANISM: Artificial
<220> FEATURE:
<223> OTHER INFORMATION: HCV PARTZYME B

<400> SEQUENCE: 32
acccagccaa ggctagctgt gagtacaccg gaattgcc                        38

<210> SEQ ID NO 33
<211> LENGTH: 127
<212> TYPE: DNA
<213> ORGANISM: Artificial
<220> FEATURE:
<223> OTHER INFORMATION: HCV TEMPLATE CONTAINING PARTZYME TARGET
      SEQUENCE

<400> SEQUENCE: 33
gagcgggttt atccaagaaa ggacccggtc gtcctggcaa ttccggtgta ctcaccggtt    60
ccgcagacca ctatggctct cccgggaggg ggggtcctgg aggctgcacg acactcatac   120
taacgcc                                                            127

<210> SEQ ID NO 34
<211> LENGTH: 21
<212> TYPE: DNA
<213> ORGANISM: Artificial
<220> FEATURE:
<223> OTHER INFORMATION: HCV PROBE
<220> FEATURE:
<221> NAME/KEY: misc_feature
<222> LOCATION: (12)..(12)
<223> OTHER INFORMATION: n is uracil
<220> FEATURE:
<221> NAME/KEY: misc_feature
<222> LOCATION: (11)..(12)
<223> OTHER INFORMATION: RNA bases

<400> SEQUENCE: 34
aacatgggac gntggctggg t                                          21

<210> SEQ ID NO 35
<211> LENGTH: 20
<212> TYPE: DNA
<213> ORGANISM: Artificial
<220> FEATURE:
<223> OTHER INFORMATION: PPC PCR PRIMER

<400> SEQUENCE: 35
agctgatctc cgaggtgcag                                            20

<210> SEQ ID NO 36
<211> LENGTH: 23
<212> TYPE: DNA
<213> ORGANISM: Artificial
<220> FEATURE:
<223> OTHER INFORMATION: PPC PCR PRIMER

<400> SEQUENCE: 36
```

-continued

```
agctctcgta ccgtgtttgc tgt                                              23

<210> SEQ ID NO 37
<211> LENGTH: 36
<212> TYPE: DNA
<213> ORGANISM: Artificial
<220> FEATURE:
<223> OTHER INFORMATION: PPC PARTZYME A

<400> SEQUENCE: 37
acttcactga tgtcccctga caacgaggtt gtgctg                                36

<210> SEQ ID NO 38
<211> LENGTH: 37
<212> TYPE: DNA
<213> ORGANISM: Artificial
<220> FEATURE:
<223> OTHER INFORMATION: PPC PARTZYME B

<400> SEQUENCE: 38
cggttggtga ggctagctgt cgatggtacg gatggtt                               37

<210> SEQ ID NO 39
<211> LENGTH: 146
<212> TYPE: DNA
<213> ORGANISM: Artificial
<220> FEATURE:
<223> OTHER INFORMATION: PPC TEMPLATE CONTAINING TARGET SEQUENCE

<400> SEQUENCE: 39
agctctcgta ccgtgtttgc tgttgattac aaccatccgt accatcgacc aggggacatc      60
agtgaagtct gcgatgatgt gtttccagta acagtcgctc cttctaagtt agcgttcgtt     120
agaaatctgc cctcggaga tcagct                                          146

<210> SEQ ID NO 40
<211> LENGTH: 21
<212> TYPE: DNA
<213> ORGANISM: Artificial
<220> FEATURE:
<223> OTHER INFORMATION: PPC PROBE
<220> FEATURE:
<221> NAME/KEY: misc_feature
<222> LOCATION: (12)..(12)
<223> OTHER INFORMATION: n is uracil
<220> FEATURE:
<221> NAME/KEY: misc_feature
<222> LOCATION: (11)..(12)
<223> OTHER INFORMATION: RNA bases

<400> SEQUENCE: 40
cagcacaacc gncaccaacc g                                                21

<210> SEQ ID NO 41
<211> LENGTH: 21
<212> TYPE: DNA
<213> ORGANISM: Artificial
<220> FEATURE:
<223> OTHER INFORMATION: BCL21 PRIMER

<400> SEQUENCE: 41
tccctttcct tccatcccta c                                                21

<210> SEQ ID NO 42
<211> LENGTH: 21
<212> TYPE: DNA
```

```
<213> ORGANISM: Artificial
<220> FEATURE:
<223> OTHER INFORMATION: BCL21 PRIMER

<400> SEQUENCE: 42
cctggtcctt gcatctttat c                                              21

<210> SEQ ID NO 43
<211> LENGTH: 37
<212> TYPE: DNA
<213> ORGANISM: Artificial
<220> FEATURE:
<223> OTHER INFORMATION: BCL21 PARTZYME A

<400> SEQUENCE: 43
cctaagagcc atttagggga caacgagagg aaacctt                              37

<210> SEQ ID NO 44
<211> LENGTH: 38
<212> TYPE: DNA
<213> ORGANISM: Artificial
<220> FEATURE:
<223> OTHER INFORMATION: BCL21 PARTZYME B

<400> SEQUENCE: 44
tgcccaggga ggctagctcc acttttgact agggattc                             38

<210> SEQ ID NO 45
<211> LENGTH: 21
<212> TYPE: DNA
<213> ORGANISM: Artificial
<220> FEATURE:
<223> OTHER INFORMATION: BIRC2 PRIMER

<400> SEQUENCE: 45
agatagggta gcctgctttg c                                               21

<210> SEQ ID NO 46
<211> LENGTH: 21
<212> TYPE: DNA
<213> ORGANISM: Artificial
<220> FEATURE:
<223> OTHER INFORMATION: BIRC2 PRIMER

<400> SEQUENCE: 46
gctgaactgg aacactagat g                                               21

<210> SEQ ID NO 47
<211> LENGTH: 37
<212> TYPE: DNA
<213> ORGANISM: Artificial
<220> FEATURE:
<223> OTHER INFORMATION: BIRC2 PARTZYME A

<400> SEQUENCE: 47
agcatgcaga cacatgcaga caacgagagg aaacctt                              37

<210> SEQ ID NO 48
<211> LENGTH: 43
<212> TYPE: DNA
<213> ORGANISM: Artificial
<220> FEATURE:
<223> OTHER INFORMATION: BIRC2 PARTZYME B

<400> SEQUENCE: 48
tgcccaggga ggctagctct cgaatgagaa catttatgta ctg                       43
```

<210> SEQ ID NO 49
<211> LENGTH: 21
<212> TYPE: DNA
<213> ORGANISM: Artificial
<220> FEATURE:
<223> OTHER INFORMATION: CCND1 PRIMER

<400> SEQUENCE: 49
aacaagctca agtggaacct g                                              21

<210> SEQ ID NO 50
<211> LENGTH: 19
<212> TYPE: DNA
<213> ORGANISM: Artificial
<220> FEATURE:
<223> OTHER INFORMATION: CCND1 PRIMER

<400> SEQUENCE: 50
acagagggca acgaaggtc                                                 19

<210> SEQ ID NO 51
<211> LENGTH: 37
<212> TYPE: DNA
<213> ORGANISM: Artificial
<220> FEATURE:
<223> OTHER INFORMATION: CCND1 PARTZYME A

<400> SEQUENCE: 51
ctctccaaaa tgccagagga caacgagagg aaacctt                             37

<210> SEQ ID NO 52
<211> LENGTH: 38
<212> TYPE: DNA
<213> ORGANISM: Artificial
<220> FEATURE:
<223> OTHER INFORMATION: CCND1 PARTZYME B

<400> SEQUENCE: 52
tgcccaggga ggctagctcg gaggagaaca aacagatc                            38

<210> SEQ ID NO 53
<211> LENGTH: 21
<212> TYPE: DNA
<213> ORGANISM: Artificial
<220> FEATURE:
<223> OTHER INFORMATION: PRDM1 PRIMER

<400> SEQUENCE: 53
tcactgttgg tggcatactt g                                              21

<210> SEQ ID NO 54
<211> LENGTH: 21
<212> TYPE: DNA
<213> ORGANISM: Artificial
<220> FEATURE:
<223> OTHER INFORMATION: PRDM1 PRIMER

<400> SEQUENCE: 54
gaggctgagt ttgaagagaa g                                              21

<210> SEQ ID NO 55
<211> LENGTH: 37
<212> TYPE: DNA
<213> ORGANISM: Artificial
<220> FEATURE:

<223> OTHER INFORMATION: PRDM1 PARTZYME A

<400> SEQUENCE: 55
atcagcacca gaatcccaga caacgagagg aaaccctt                                37

<210> SEQ ID NO 56
<211> LENGTH: 38
<212> TYPE: DNA
<213> ORGANISM: Artificial
<220> FEATURE:
<223> OTHER INFORMATION: PRDM1 PARTZYME B

<400> SEQUENCE: 56
tgcccaggga ggctagctgg gtggtcgttc acaatgta                                38

<210> SEQ ID NO 57
<211> LENGTH: 21
<212> TYPE: DNA
<213> ORGANISM: Artificial
<220> FEATURE:
<223> OTHER INFORMATION: CCNE1 PRIMER

<400> SEQUENCE: 57
agtacccaca atgagtcaaa g                                                   21

<210> SEQ ID NO 58
<211> LENGTH: 21
<212> TYPE: DNA
<213> ORGANISM: Artificial
<220> FEATURE:
<223> OTHER INFORMATION: CCNE1 PRIMER

<400> SEQUENCE: 58
tgatggaatt aacacagaag c                                                   21

<210> SEQ ID NO 59
<211> LENGTH: 38
<212> TYPE: DNA
<213> ORGANISM: Artificial
<220> FEATURE:
<223> OTHER INFORMATION: CCNE1 PARTZYME A

<400> SEQUENCE: 59
atccatttat ttaatggtgg acaacgagag gaaaccctt                               38

<210> SEQ ID NO 60
<211> LENGTH: 37
<212> TYPE: DNA
<213> ORGANISM: Artificial
<220> FEATURE:
<223> OTHER INFORMATION: CCNE1 PARTZYME B

<400> SEQUENCE: 60
tgcccaggga ggctagctgt gggagttgtg ttctttt                                 37

<210> SEQ ID NO 61
<211> LENGTH: 21
<212> TYPE: DNA
<213> ORGANISM: Artificial
<220> FEATURE:
<223> OTHER INFORMATION: CDK4 PRIMER

<400> SEQUENCE: 61
tctctgaggc tatggagggt c                                                   21

```
<210> SEQ ID NO 62
<211> LENGTH: 21
<212> TYPE: DNA
<213> ORGANISM: Artificial
<220> FEATURE:
<223> OTHER INFORMATION: CDK4 PRIMER

<400> SEQUENCE: 62
tataaaggta gggaaaggga c                                              21

<210> SEQ ID NO 63
<211> LENGTH: 37
<212> TYPE: DNA
<213> ORGANISM: Artificial
<220> FEATURE:
<223> OTHER INFORMATION: CDK4 PARTZYME A

<400> SEQUENCE: 63
tcccacctct cctttgaga caacgagagg aaaccctt                             37

<210> SEQ ID NO 64
<211> LENGTH: 38
<212> TYPE: DNA
<213> ORGANISM: Artificial
<220> FEATURE:
<223> OTHER INFORMATION: CDK4 PARTZYME B

<400> SEQUENCE: 64
tgcccaggga ggctagctgc ttctccttct ccttccca                            38

<210> SEQ ID NO 65
<211> LENGTH: 20
<212> TYPE: DNA
<213> ORGANISM: Artificial
<220> FEATURE:
<223> OTHER INFORMATION: EGFR PRIMER

<400> SEQUENCE: 65
aggaggtggc tggttatgtc                                                20

<210> SEQ ID NO 66
<211> LENGTH: 24
<212> TYPE: DNA
<213> ORGANISM: Artificial
<220> FEATURE:
<223> OTHER INFORMATION: EGFR PRIMER

<400> SEQUENCE: 66
tgcatcatag ttagataaga ctgc                                           24

<210> SEQ ID NO 67
<211> LENGTH: 37
<212> TYPE: DNA
<213> ORGANISM: Artificial
<220> FEATURE:
<223> OTHER INFORMATION: EGFR PARTZYME A

<400> SEQUENCE: 67
cattgccctc aacacagtga caacgagagg aaaccctt                            37

<210> SEQ ID NO 68
<211> LENGTH: 38
<212> TYPE: DNA
<213> ORGANISM: Artificial
<220> FEATURE:
<223> OTHER INFORMATION: EGFR PARTZYME B
```

<400> SEQUENCE: 68
tgcccaggga ggctagctga gcgaattcct ttggaaaa　　　　　　　　　　　　38

<210> SEQ ID NO 69
<211> LENGTH: 21
<212> TYPE: DNA
<213> ORGANISM: Artificial
<220> FEATURE:
<223> OTHER INFORMATION: EMSY / C11orf30 PRIMER

<400> SEQUENCE: 69
gtagaactgc tgctgccact g　　　　　　　　　　　　　　　　　　　　　21

<210> SEQ ID NO 70
<211> LENGTH: 21
<212> TYPE: DNA
<213> ORGANISM: Artificial
<220> FEATURE:
<223> OTHER INFORMATION: EMSY / C11orf30 PRIMER

<400> SEQUENCE: 70
attctctcca aatcccataa c　　　　　　　　　　　　　　　　　　　　　21

<210> SEQ ID NO 71
<211> LENGTH: 37
<212> TYPE: DNA
<213> ORGANISM: Artificial
<220> FEATURE:
<223> OTHER INFORMATION: EMSY / C11orf30 PARTZYME A

<400> SEQUENCE: 71
taacaactgg tggcttctga caacgagagg aaacctt　　　　　　　　　　　　　37

<210> SEQ ID NO 72
<211> LENGTH: 38
<212> TYPE: DNA
<213> ORGANISM: Artificial
<220> FEATURE:
<223> OTHER INFORMATION: EMSY / C11orf30 PARTZYME B

<400> SEQUENCE: 72
tgcccaggga ggctagctgg ttgtagaagc aatgactg　　　　　　　　　　　　38

<210> SEQ ID NO 73
<211> LENGTH: 19
<212> TYPE: DNA
<213> ORGANISM: Artificial
<220> FEATURE:
<223> OTHER INFORMATION: ERBB2 PRIMER

<400> SEQUENCE: 73
tgaagtacca cctcccgag　　　　　　　　　　　　　　　　　　　　　　19

<210> SEQ ID NO 74
<211> LENGTH: 19
<212> TYPE: DNA
<213> ORGANISM: Artificial
<220> FEATURE:
<223> OTHER INFORMATION: ERBB2 PRIMER

<400> SEQUENCE: 74
cataagccaa attctgtgc　　　　　　　　　　　　　　　　　　　　　　19

<210> SEQ ID NO 75
<211> LENGTH: 37

```
<212> TYPE: DNA
<213> ORGANISM: Artificial
<220> FEATURE:
<223> OTHER INFORMATION: ERBB2 PARTZYME A

<400> SEQUENCE: 75
gaggtagagt ggtgaacaga caacgagagg aaacctt                              37

<210> SEQ ID NO 76
<211> LENGTH: 37
<212> TYPE: DNA
<213> ORGANISM: Artificial
<220> FEATURE:
<223> OTHER INFORMATION: ERBB2 PARTZYME B

<400> SEQUENCE: 76
tgcccaggga ggctagctga cagcaaaggt tctaccc                              37

<210> SEQ ID NO 77
<211> LENGTH: 21
<212> TYPE: DNA
<213> ORGANISM: Artificial
<220> FEATURE:
<223> OTHER INFORMATION: FGFR1 PRIMER

<400> SEQUENCE: 77
ctgtacctgg agatcatcat c                                               21

<210> SEQ ID NO 78
<211> LENGTH: 21
<212> TYPE: DNA
<213> ORGANISM: Artificial
<220> FEATURE:
<223> OTHER INFORMATION: FGFR1 PRIMER

<400> SEQUENCE: 78
atctggctgt ggaagtcact c                                               21

<210> SEQ ID NO 79
<211> LENGTH: 37
<212> TYPE: DNA
<213> ORGANISM: Artificial
<220> FEATURE:
<223> OTHER INFORMATION: FGFR1 PARTZYME A

<400> SEQUENCE: 79
ctcatctcct gcatggtgga caacgagagg aaacctt                              37

<210> SEQ ID NO 80
<211> LENGTH: 38
<212> TYPE: DNA
<213> ORGANISM: Artificial
<220> FEATURE:
<223> OTHER INFORMATION: FGFR1 PARTZYME B

<400> SEQUENCE: 80
tgcccaggga ggctagctgg tcggtcatcg tctacaag                             38

<210> SEQ ID NO 81
<211> LENGTH: 21
<212> TYPE: DNA
<213> ORGANISM: Artificial
<220> FEATURE:
<223> OTHER INFORMATION: HMGA2 PRIMER

<400> SEQUENCE: 81
```

```
actcactcta ggcacatgca g                                              21

<210> SEQ ID NO 82
<211> LENGTH: 21
<212> TYPE: DNA
<213> ORGANISM: Artificial
<220> FEATURE:
<223> OTHER INFORMATION: HMGA2 PRIMER

<400> SEQUENCE: 82
tgaaatcaaa ccacaccata g                                              21

<210> SEQ ID NO 83
<211> LENGTH: 37
<212> TYPE: DNA
<213> ORGANISM: Artificial
<220> FEATURE:
<223> OTHER INFORMATION: HMGA2 PARTZYME A

<400> SEQUENCE: 83
ttagagagta gagggtggga caacgagagg aaacctt                             37

<210> SEQ ID NO 84
<211> LENGTH: 38
<212> TYPE: DNA
<213> ORGANISM: Artificial
<220> FEATURE:
<223> OTHER INFORMATION: HMGA2 PARTZYME B

<400> SEQUENCE: 84
tgcccaggga ggctagctct gaactccagt tactctcg                            38

<210> SEQ ID NO 85
<211> LENGTH: 21
<212> TYPE: DNA
<213> ORGANISM: Artificial
<220> FEATURE:
<223> OTHER INFORMATION: MET PRIMER

<400> SEQUENCE: 85
agacaaatag gagccagcct g                                              21

<210> SEQ ID NO 86
<211> LENGTH: 21
<212> TYPE: DNA
<213> ORGANISM: Artificial
<220> FEATURE:
<223> OTHER INFORMATION: MET PRIMER

<400> SEQUENCE: 86
cttgttgaag aagtcgttga c                                              21

<210> SEQ ID NO 87
<211> LENGTH: 37
<212> TYPE: DNA
<213> ORGANISM: Artificial
<220> FEATURE:
<223> OTHER INFORMATION: MET PARTZYME A

<400> SEQUENCE: 87
attcttttcg gggtgttcga caacgagagg aaacctt                             37

<210> SEQ ID NO 88
<211> LENGTH: 38
<212> TYPE: DNA
<213> ORGANISM: Artificial
```

```
<220> FEATURE:
<223> OTHER INFORMATION: MET PARTZYME B

<400> SEQUENCE: 88
tgcccaggga ggctagctca caaagcaagc cagattct                              38

<210> SEQ ID NO 89
<211> LENGTH: 21
<212> TYPE: DNA
<213> ORGANISM: Artificial
<220> FEATURE:
<223> OTHER INFORMATION: MYC PRIMER

<400> SEQUENCE: 89
atacatcctg tccgtccaag c                                               21

<210> SEQ ID NO 90
<211> LENGTH: 21
<212> TYPE: DNA
<213> ORGANISM: Artificial
<220> FEATURE:
<223> OTHER INFORMATION: MYC PRIMER

<400> SEQUENCE: 90
acaagagttc cgtagctgtt c                                               21

<210> SEQ ID NO 91
<211> LENGTH: 37
<212> TYPE: DNA
<213> ORGANISM: Artificial
<220> FEATURE:
<223> OTHER INFORMATION: MYC PARTZYME A

<400> SEQUENCE: 91
ctgaagagga cttgttgcga caacgagagg aaacctt                              37

<210> SEQ ID NO 92
<211> LENGTH: 38
<212> TYPE: DNA
<213> ORGANISM: Artificial
<220> FEATURE:
<223> OTHER INFORMATION: MYC PARTZYME B

<400> SEQUENCE: 92
tgcccaggga ggctagctga aacgacgaga acagttga                             38

<210> SEQ ID NO 93
<211> LENGTH: 21
<212> TYPE: DNA
<213> ORGANISM: Artificial
<220> FEATURE:
<223> OTHER INFORMATION: PIK3CA PRIMER

<400> SEQUENCE: 93 ttcttcccttt tctgcttctt g                                              21

<210> SEQ ID NO 94
<211> LENGTH: 21
<212> TYPE: DNA
<213> ORGANISM: Artificial
<220> FEATURE:
<223> OTHER INFORMATION: PIK3CA PRIMER

<400> SEQUENCE: 94
actttagaat gcctccgtga g                                               21
```

```
<210> SEQ ID NO 95
<211> LENGTH: 37
<212> TYPE: DNA
<213> ORGANISM: Artificial
<220> FEATURE:
<223> OTHER INFORMATION: PIK3CA PARTZYME A

<400> SEQUENCE: 95
tgaagaagtt gatggaggga caacgagagg aaacctt                              37

<210> SEQ ID NO 96
<211> LENGTH: 40
<212> TYPE: DNA
<213> ORGANISM: Artificial
<220> FEATURE:
<223> OTHER INFORMATION: PIK3CA PARTZYME B

<400> SEQUENCE: 96
tgcccaggga ggctagctgg tattttcttg cttctttaaa                           40

<210> SEQ ID NO 97
<211> LENGTH: 21
<212> TYPE: DNA
<213> ORGANISM: Artificial
<220> FEATURE:
<223> OTHER INFORMATION: VEGFA PRIMER

<400> SEQUENCE: 97
cactcacaca cacacaacca g                                              21

<210> SEQ ID NO 98
<211> LENGTH: 21
<212> TYPE: DNA
<213> ORGANISM: Artificial
<220> FEATURE:
<223> OTHER INFORMATION: VEGFA PRIMER

<400> SEQUENCE: 98
cacattgttg gaagaagcag c                                              21

<210> SEQ ID NO 99
<211> LENGTH: 37
<212> TYPE: DNA
<213> ORGANISM: Artificial
<220> FEATURE:
<223> OTHER INFORMATION: VEGFA PARTZYME A

<400> SEQUENCE: 99
gtggtttcaa tggtgtgaga caacgagagg aaacctt                             37

<210> SEQ ID NO 100
<211> LENGTH: 38
<212> TYPE: DNA
<213> ORGANISM: Artificial
<220> FEATURE:
<223> OTHER INFORMATION: VEGFA PARTZYME B

<400> SEQUENCE: 100
tgcccaggga ggctagctga cataggtcct tttaggct                            38

<210> SEQ ID NO 101
<211> LENGTH: 21
<212> TYPE: DNA
<213> ORGANISM: Artificial
<220> FEATURE:
<223> OTHER INFORMATION: YWHAZ PRIMER
```

<400> SEQUENCE: 101
aacattgtcc ctgctcttga g                                          21

<210> SEQ ID NO 102
<211> LENGTH: 23
<212> TYPE: DNA
<213> ORGANISM: Artificial
<220> FEATURE:
<223> OTHER INFORMATION: YWHAZ PRIMER

<400> SEQUENCE: 102
tcctctttct tcctcctcta ttc                                        23

<210> SEQ ID NO 103
<211> LENGTH: 39
<212> TYPE: DNA
<213> ORGANISM: Artificial
<220> FEATURE:
<223> OTHER INFORMATION: YWHAZ PARTZYME A

<400> SEQUENCE: 103
tgagctttgg gtataactta gacaacgaga ggaaacctt                       39

<210> SEQ ID NO 104
<211> LENGTH: 37
<212> TYPE: DNA
<213> ORGANISM: Artificial
<220> FEATURE:
<223> OTHER INFORMATION: YWHAZ PARTZYME B

<400> SEQUENCE: 104
tgcccaggga ggctagctcc ccatcattat ttagaga                         37

<210> SEQ ID NO 105
<211> LENGTH: 21
<212> TYPE: DNA
<213> ORGANISM: Artificial
<220> FEATURE:
<223> OTHER INFORMATION: ZNF217 PRIMER

<400> SEQUENCE: 105
ccaatgagtg ttacagagag c                                          21

<210> SEQ ID NO 106
<211> LENGTH: 21
<212> TYPE: DNA
<213> ORGANISM: Artificial
<220> FEATURE:
<223> OTHER INFORMATION: ZNF217 PRIMER

<400> SEQUENCE: 106
tccagcataa tacaaatcga c                                          21

<210> SEQ ID NO 107
<211> LENGTH: 38
<212> TYPE: DNA
<213> ORGANISM: Artificial
<220> FEATURE:
<223> OTHER INFORMATION: ZNF217 PARTZYME A

<400> SEQUENCE: 107
gggtatgtga taatagaggg acaacgagag gaaacctt                        38

<210> SEQ ID NO 108

```
<211> LENGTH: 38
<212> TYPE: DNA
<213> ORGANISM: Artificial
<220> FEATURE:
<223> OTHER INFORMATION: ZNF217 PARTZYME B

<400> SEQUENCE: 108
tgcccaggga ggctagctct ggaatttaaa cctgtatt                            38

<210> SEQ ID NO 109
<211> LENGTH: 21
<212> TYPE: DNA
<213> ORGANISM: Artificial
<220> FEATURE:
<223> OTHER INFORMATION: REL  PRIMER

<400> SEQUENCE: 109
ctgttacggg ttctgtgata g                                              21

<210> SEQ ID NO 110
<211> LENGTH: 21
<212> TYPE: DNA
<213> ORGANISM: Artificial
<220> FEATURE:
<223> OTHER INFORMATION: REL  PRIMER

<400> SEQUENCE: 110
ttgtgttgaa cgattgggaa g                                              21

<210> SEQ ID NO 111
<211> LENGTH: 37
<212> TYPE: DNA
<213> ORGANISM: Artificial
<220> FEATURE:
<223> OTHER INFORMATION: REL  PARTZYME A

<400> SEQUENCE: 111
aaacaatggc tacttgacga caacgagagg aaacctt                             37

<210> SEQ ID NO 112
<211> LENGTH: 38
<212> TYPE: DNA
<213> ORGANISM: Artificial
<220> FEATURE:
<223> OTHER INFORMATION: REL  PARTZYME B

<400> SEQUENCE: 112
tgcccaggga ggctagctgt gtacatcagc ttgtgaaa                            38

<210> SEQ ID NO 113
<211> LENGTH: 21
<212> TYPE: DNA
<213> ORGANISM: Artificial
<220> FEATURE:
<223> OTHER INFORMATION: CDKN2A PRIMER

<400> SEQUENCE: 113
cattcatgtg ggcatttctt g                                              21

<210> SEQ ID NO 114
<211> LENGTH: 21
<212> TYPE: DNA
<213> ORGANISM: Artificial
<220> FEATURE:
<223> OTHER INFORMATION: CDKN2A PRIMER

<400> SEQUENCE: 114
```
ttatttgagc tttggttctg c          21

<210> SEQ ID NO 115
<211> LENGTH: 37
<212> TYPE: DNA
<213> ORGANISM: Artificial
<220> FEATURE:
<223> OTHER INFORMATION: CDKN2A PARTZYME A

<400> SEQUENCE: 115
aactagggaa gctcagggga caacgagagg aaacctt          37

<210> SEQ ID NO 116
<211> LENGTH: 38
<212> TYPE: DNA
<213> ORGANISM: Artificial
<220> FEATURE:
<223> OTHER INFORMATION: CDKN2A PARTZYME B

<400> SEQUENCE: 116
tgcccaggga ggctagctgg ttactggctt ctcttgag          38

<210> SEQ ID NO 117
<211> LENGTH: 21
<212> TYPE: DNA
<213> ORGANISM: Artificial
<220> FEATURE:
<223> OTHER INFORMATION: CSMD1 PRIMER

<400> SEQUENCE: 117
cagagttgtg tcaaacctca c          21

<210> SEQ ID NO 118
<211> LENGTH: 21
<212> TYPE: DNA
<213> ORGANISM: Artificial
<220> FEATURE:
<223> OTHER INFORMATION: CSMD1 PRIMER

<400> SEQUENCE: 118
ttcaatacaa tggctatgct g          21

<210> SEQ ID NO 119
<211> LENGTH: 38
<212> TYPE: DNA
<213> ORGANISM: Artificial
<220> FEATURE:
<223> OTHER INFORMATION: CSMD1 PARTZYME A

<400> SEQUENCE: 119
aagtttgtat catacatggg acaacgagag gaaacctt          38

<210> SEQ ID NO 120
<211> LENGTH: 37
<212> TYPE: DNA
<213> ORGANISM: Artificial
<220> FEATURE:
<223> OTHER INFORMATION: CSMD1 PARTZYME B

<400> SEQUENCE: 120
tgcccaggga ggctagctgt tttcaaacga tgcttgt          37

<210> SEQ ID NO 121
<211> LENGTH: 21
<212> TYPE: DNA

<213> ORGANISM: Artificial
<220> FEATURE:
<223> OTHER INFORMATION: FHIT PRIMER

<400> SEQUENCE: 121
cctgtctgag ccgtttaggt c                                              21

<210> SEQ ID NO 122
<211> LENGTH: 21
<212> TYPE: DNA
<213> ORGANISM: Artificial
<220> FEATURE:
<223> OTHER INFORMATION: FHIT PRIMER

<400> SEQUENCE: 122
cagtttcttc atctcaccat c                                              21

<210> SEQ ID NO 123
<211> LENGTH: 37
<212> TYPE: DNA
<213> ORGANISM: Artificial
<220> FEATURE:
<223> OTHER INFORMATION: FHIT PARTZYME A

<400> SEQUENCE: 123
agttggagtg accgaggtga caacgagagg aaacctt                             37

<210> SEQ ID NO 124
<211> LENGTH: 38
<212> TYPE: DNA
<213> ORGANISM: Artificial
<220> FEATURE:
<223> OTHER INFORMATION: FHIT PARTZYME B

<400> SEQUENCE: 124
tgcccaggga ggctagctgg ggatcactgg ttgaagaa                            38

<210> SEQ ID NO 125
<211> LENGTH: 21
<212> TYPE: DNA
<213> ORGANISM: Artificial
<220> FEATURE:
<223> OTHER INFORMATION: PTEN PRIMER

<400> SEQUENCE: 125
atgtggaggc tatcaacaaa g                                              21

<210> SEQ ID NO 126
<211> LENGTH: 21
<212> TYPE: DNA
<213> ORGANISM: Artificial
<220> FEATURE:
<223> OTHER INFORMATION: PTEN PRIMER

<400> SEQUENCE: 126
ccacagcagg tattatgatt g                                              21

<210> SEQ ID NO 127
<211> LENGTH: 37
<212> TYPE: DNA
<213> ORGANISM: Artificial
<220> FEATURE:
<223> OTHER INFORMATION: PTEN PARTZYME A

<400> SEQUENCE: 127
atctcctgtg taatcaagga caacgagagg aaacctt                             37

<210> SEQ ID NO 128
<211> LENGTH: 38
<212> TYPE: DNA
<213> ORGANISM: Artificial
<220> FEATURE:
<223> OTHER INFORMATION: PTEN PARTZYME B

<400> SEQUENCE: 128
tgcccaggga ggctagctcc agtgctaaaa ttcagatg                             38

<210> SEQ ID NO 129
<211> LENGTH: 19
<212> TYPE: DNA
<213> ORGANISM: Artificial
<220> FEATURE:
<223> OTHER INFORMATION: PTPRD PRIMER

<400> SEQUENCE: 129
agcatcggga gggttacag                                                  19

<210> SEQ ID NO 130
<211> LENGTH: 21
<212> TYPE: DNA
<213> ORGANISM: Artificial
<220> FEATURE:
<223> OTHER INFORMATION: PTPRD PRIMER

<400> SEQUENCE: 130
agagaagtga gacaattcca g                                               21

<210> SEQ ID NO 131
<211> LENGTH: 39
<212> TYPE: DNA
<213> ORGANISM: Artificial
<220> FEATURE:
<223> OTHER INFORMATION: PTPRD PARTZYME A

<400> SEQUENCE: 131
gaaagctaga aaggtgtag gacaacgaga ggaaacctt                             39

<210> SEQ ID NO 132
<211> LENGTH: 38
<212> TYPE: DNA
<213> ORGANISM: Artificial
<220> FEATURE:
<223> OTHER INFORMATION: PTPRD PARTZYME B

<400> SEQUENCE: 132
tgcccaggga ggctagctgt gttctggaac accatgat                             38

<210> SEQ ID NO 133
<211> LENGTH: 20
<212> TYPE: DNA
<213> ORGANISM: Artificial
<220> FEATURE:
<223> OTHER INFORMATION: RB1 PRIMER

<400> SEQUENCE: 133
ccttctgtct gagcacccag                                                 20

<210> SEQ ID NO 134
<211> LENGTH: 19
<212> TYPE: DNA
<213> ORGANISM: Artificial
<220> FEATURE:

```
<223> OTHER INFORMATION: RB1 PRIMER

<400> SEQUENCE: 134
gtccaaatgc ctgtctctc                                                    19

<210> SEQ ID NO 135
<211> LENGTH: 37
<212> TYPE: DNA
<213> ORGANISM: Artificial
<220> FEATURE:
<223> OTHER INFORMATION: RB1 PARTZYME A

<400> SEQUENCE: 135
catctggacc cttttccaga caacgagagg aaacctt                                 37

<210> SEQ ID NO 136
<211> LENGTH: 38
<212> TYPE: DNA
<213> ORGANISM: Artificial
<220> FEATURE:
<223> OTHER INFORMATION: RB1 PARTZYME B

<400> SEQUENCE: 136
tgcccaggga ggctagctca caccctgcag aatgagta                                38

<210> SEQ ID NO 137
<211> LENGTH: 19
<212> TYPE: DNA
<213> ORGANISM: Artificial
<220> FEATURE:
<223> OTHER INFORMATION: RPP40 PRIMER

<400> SEQUENCE: 137
attgctgtcc tgagccaag                                                    19

<210> SEQ ID NO 138
<211> LENGTH: 22
<212> TYPE: DNA
<213> ORGANISM: Artificial
<220> FEATURE:
<223> OTHER INFORMATION: RPP40 PRIMER

<400> SEQUENCE: 138
cagagatgtt ccaataggag ac                                                22

<210> SEQ ID NO 139
<211> LENGTH: 38
<212> TYPE: DNA
<213> ORGANISM: Artificial
<220> FEATURE:
<223> OTHER INFORMATION: RPP40 PARTZYME A

<400> SEQUENCE: 139
cttatttgtg tacaatcact gacaacgaga ggcgtgat                                38

<210> SEQ ID NO 140
<211> LENGTH: 38
<212> TYPE: DNA
<213> ORGANISM: Artificial
<220> FEATURE:
<223> OTHER INFORMATION: RPP40 PARTZYME B

<400> SEQUENCE: 140
ctgggaggaa ggctagctgc ttcatacttc cagagaag                                38
```

-continued

```
<210> SEQ ID NO 141
<211> LENGTH: 22
<212> TYPE: DNA
<213> ORGANISM: Artificial
<220> FEATURE:
<223> OTHER INFORMATION: Sub2-FAM PROBE
<220> FEATURE:
<221> NAME/KEY: misc_feature
<222> LOCATION: (13)..(13)
<223> OTHER INFORMATION: n is uracil
<220> FEATURE:
<221> NAME/KEY: misc_feature
<222> LOCATION: (12)..(13)
<223> OTHER INFORMATION: RNA bases

<400> SEQUENCE: 141
aaggtttcct cgnccctggg ca                                                 22

<210> SEQ ID NO 142
<211> LENGTH: 21
<212> TYPE: DNA
<213> ORGANISM: Artificial
<220> FEATURE:
<223> OTHER INFORMATION: Sub6-HEX PROBE
<220> FEATURE:
<221> NAME/KEY: misc_feature
<222> LOCATION: (12)..(12)
<223> OTHER INFORMATION: n is uracil
<220> FEATURE:
<221> NAME/KEY: misc_feature
<222> LOCATION: (11)..(12)
<223> OTHER INFORMATION: RNA bases

<400> SEQUENCE: 142
atcacgcctc gntcctccca g                                                  21

<210> SEQ ID NO 143
<211> LENGTH: 21
<212> TYPE: DNA
<213> ORGANISM: Artificial
<220> FEATURE:
<223> OTHER INFORMATION: Reverse primer

<400> SEQUENCE: 143
ctctgcctaa tcatctcatg t                                                  21

<210> SEQ ID NO 144
<211> LENGTH: 19
<212> TYPE: DNA
<213> ORGANISM: Artificial
<220> FEATURE:
<223> OTHER INFORMATION: Partzyme A detecting region

<400> SEQUENCE: 144
aggtctttgt actaggagg                                                     19

<210> SEQ ID NO 145
<211> LENGTH: 20
<212> TYPE: DNA
<213> ORGANISM: Artificial
<220> FEATURE:
<223> OTHER INFORMATION: Partzyme B detecting region

<400> SEQUENCE: 145
ctgtaggcat aaattggtct                                                    20

<210> SEQ ID NO 146
<211> LENGTH: 21
<212> TYPE: DNA
```

```
<213> ORGANISM: Artificial
<220> FEATURE:
<223> OTHER INFORMATION: Reverse primer region

<400> SEQUENCE: 146
ctttcttgga taaacccgct c                                        21

<210> SEQ ID NO 147
<211> LENGTH: 19
<212> TYPE: DNA
<213> ORGANISM: Artificial
<220> FEATURE:
<223> OTHER INFORMATION: Partzyme A detecting region

<400> SEQUENCE: 147
atagtggtct gcggaaccg                                           19

<210> SEQ ID NO 148
<211> LENGTH: 20
<212> TYPE: DNA
<213> ORGANISM: Artificial
<220> FEATURE:
<223> OTHER INFORMATION: Partzyme B detecting region

<400> SEQUENCE: 148
gtgagtacac cggaattgcc                                          20

<210> SEQ ID NO 149
<211> LENGTH: 21
<212> TYPE: DNA
<213> ORGANISM: Artificial
<220> FEATURE:
<223> OTHER INFORMATION: Reverse primer region

<400> SEQUENCE: 149
gtatagccct accagcattc t                                        21

<210> SEQ ID NO 150
<211> LENGTH: 19
<212> TYPE: DNA
<213> ORGANISM: Artificial
<220> FEATURE:
<223> OTHER INFORMATION: Partzyme A detecting region

<400> SEQUENCE: 150
acaaataatc cacctatcc                                           19

<210> SEQ ID NO 151
<211> LENGTH: 23
<212> TYPE: DNA
<213> ORGANISM: Artificial
<220> FEATURE:
<223> OTHER INFORMATION: Partzyme B detecting region

<400> SEQUENCE: 151
cagtaggaga aatctataaa aga                                      23

<210> SEQ ID NO 152
<211> LENGTH: 16
<212> TYPE: DNA
<213> ORGANISM: Artificial
<220> FEATURE:
<223> OTHER INFORMATION: DNAzyme
<220> FEATURE:
<221> NAME/KEY: misc_feature
<222> LOCATION: (1)..(1)
<223> OTHER INFORMATION: n is a, c, g, or t
```

```
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (15)..(15)
<223> OTHER INFORMATION: n is a or g
<220> FEATURE:
<221> NAME/KEY: misc_feature
<222> LOCATION: (16)..(16)
<223> OTHER INFORMATION: n is a, c, g, or t

<400> SEQUENCE: 152
ntnnnagcnn nwcgnn                                                   16

<210> SEQ ID NO 153
<211> LENGTH: 17
<212> TYPE: DNA
<213> ORGANISM: Artificial
<220> FEATURE:
<223> OTHER INFORMATION: DNAzyme
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (11)..(13)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 153
nggmtmghnd nnnmgdn                                                  17

<210> SEQ ID NO 154
<211> LENGTH: 17
<212> TYPE: DNA
<213> ORGANISM: Artificial
<220> FEATURE:
<223> OTHER INFORMATION: DNAzyme
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 154
ntnnnagcnn nwcgaan                                                  17
```